US008546410B2

(12) United States Patent
Liu et al.

(10) Patent No.: US 8,546,410 B2
(45) Date of Patent: Oct. 1, 2013

(54) HETEROARYL-FUSED MACROCYCLIC PYRIMIDINE DERIVATIVES

(75) Inventors: Huaqing Liu, Buffalo Grove, IL (US); Irene Drizin, Wadsworth, IL (US); Marlon D. Cowart, Round Lake Beach, IL (US); Robert J. Altenbach, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 243 days.

(21) Appl. No.: 12/435,876

(22) Filed: May 5, 2009

(65) Prior Publication Data

US 2010/0004256 A1 Jan. 7, 2010

Related U.S. Application Data

(60) Provisional application No. 61/050,400, filed on May 5, 2008.

(51) Int. Cl.
*A61K 31/505* (2006.01)
*A01N 43/54* (2006.01)
*C07D 487/00* (2006.01)
*C07D 491/00* (2006.01)

(52) U.S. Cl.
USPC ............................ 514/267; 544/250; 544/251

(58) Field of Classification Search
USPC .................................. 514/267; 544/250, 251
See application file for complete search history.

(56) References Cited

U.S. PATENT DOCUMENTS

2010/0016344 A1  1/2010 Wakefield et al.

FOREIGN PATENT DOCUMENTS

| WO | WO2006050965 A1 | 5/2006 |
| WO | WO2007090852 A1 | 8/2007 |
| WO | WO2007090854 A1 | 8/2007 |
| WO | WO 2008/060767 * | 5/2008 |
| WO | WO2008060767 A2 | 5/2008 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Singh, et al., "Immune Therapy in Inflammatory Bowel Disease and Models of Colitis," British Journal of Surgery, 2001, vol. 88 (12), pp. 1558-1569.
Akdis, et al., "Histamine Receptors Are Hot in Immunopharmacology," European Journal of Pharmacology, 2006, vol. 533, pp. 69-76.
Banker, et al, "Modern Paharmaceutices, 3ed.," 1996, pp. 451 and 596, Marcel Dekker, New York.
Bell, et al., "Involvement of Histamine H4 and H1 Receptors in Scratching Induced by Histamine Receptor Agonists in Balb C Mice," British Journal of Pharmacology, 2004, vol. 142, pp. 374-380.

Bennett, et al., "A Peripheral Mononeuropathy in Rat that Produces Disorders of Pain Sensation like those Seen in Man," Pain, 1988, vol. 33 (1), pp. 87-107.
Buckland, et al., "Histamine Induces Cytoskeletal Changes in Human Eosinophils via the H(4) Receptor," British Journal of Pharmacology, 2003, vol. 140, pp. 1117-1127.
Bundgaard, H., "Design of Pro Drugs," 1985, pp. 1-6.
Caliskan, et al., "Unusual Manganese(III)-Mediated Oxidative Free Radical Additions of 1,3-Dicarbonyl Compounds to Benzonorbornadiene and 7-Heterobenzonorbornadienes: Mechanistic Studies," Journal of Organic Chemistry, 2007, vol. 72 (9), pp. 3353-3359.
Chaplan, et al., "Quantitative Assessment of Tactile Allodynia in the Rat Paw," Journal of Neuroscience Methods, 1994, vol. 53, pp. 55-63.
Cianchi, et al., "The role of Cyclooxygenase-2 in Mediating the Effects of Histamine on Cell Proliferation and Vascular Endothelial Growth Factor Production in Colorectal Cancer," Clinical Cancer Research, 2005, vol. 11 (19), pp. 6807-6815.
Coge, et al., "Structure and Expression of the Human Histamine H4-Receptor Gene," Biochemical and Biophysical Research Communications, 2001, vol. 284 (2), pp. 301-309.
Collins, et al., "Emerging Therapies for Neuropathic Pain," Expert Opinion on Emerging Drugs, 2005, vol. 10 (1), pp. 95-108.
Coruzzi, et al., Gastric Effects of the Histamine H4 Receptor Antagonists JNJ7777120 and VUF6002 35th Mtg of the European Histamine Research Society in Delphi, Greece.
Coruzzi, et al., "Anti-Inflammatory and Antinociceptive Effects of the Selective Histamine H4-Receptor Antagonists JNJ7777120 and VUF6002 in a Rat Model of Carrageenan-Induced Acute Inflammation," European Journal of Pharmacology, 2007, vol. 563 (1-3), pp. 240-244.
Cowart, et al., "Rotationally Constrained 2,4-Di Amino-5,6-di Substituted Pyrimidines: A New Class of Histamine H4 Receptor Antagonists with Improved Druglikeness and in Vivo Efficacy in Pain and Inflammation on Models,XP002543231," Journal of Medicinal Chemistry , 2008, vol. 51 (20), pp. 6547-6557.
Crabbe, et al., "Synthesis and Properties of 5-Bromocyclohepta[B]Furan-4-One," Journal of the Chemical Society Perkin Transactions, 1980, pp. 2081-2083.

(Continued)

*Primary Examiner* — Eric A Leeser
(74) *Attorney, Agent, or Firm* — Lisa V. Mueller; Michael Best & Friedrich LLP

(57) ABSTRACT

Heteroaryl-fused macrocyclic 2,4-diaminopyrimidine compounds of formula (I)

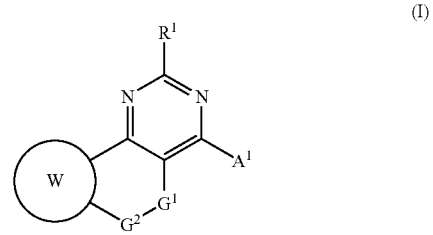

(I)

wherein W, $G^1$, $G^2$, $A_1$ and $R^1$ are defined in the description, compositions comprising such compounds, methods for making the compounds, and methods of treating and preventing the progression of diseases, conditions, and disorders using such compounds and compositions are described herein.

9 Claims, No Drawings

(56) References Cited

OTHER PUBLICATIONS

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

De Esch, et al., "The Histamine H4 Receptor as a New Therapeutic Target for Inflammation," Trends in Pharmacological Science, 2005, vol. 26 (9), pp. 462-469.

Dixon, W., "Efficient Analysis of Experimental Observations," Annual Review of Pharmacology and Toxicology, 1980, vol. 20, pp. 441-462.

Dray, et al., "Pharmacology of Chronic Pain," Trends in Pharmacological Sciences, 1994, vol. 15 (6), pp. 190-197.

Dunford, et al., "The Histamine H4 Receptor Mediates Allergic Airway Inflammation by Regulating the Activation of CD4+ T cells," The Journal of Immunology, 2006, vol. 176 (11), pp. 7062-7070.

Dworkin, R., "An Overview of Neuropathic Pain: Syndromes, Symptoms, Signs, and Several Mechanisms," Clinical Journal of Pain, 2002, vol. 18 (6), pp. 343-349.

Esbenshade, et al., "Pharmacological and Behavioral Properties of A-349821, a Selective and Potent Human Histamine H3 Receptor Antagonist," Biochemical Pharmacology, 2004, vol. 68 (5), pp. 933-945.

Fogel, et al., "Influence of H3/H4 Receptor Antagonist Thioperamide on Regional Haemodynamics in Rats with Trinitrobenzene Sulfonic Acid-Induced Colitis 35th Meeting of the European Histamine Research Society in Delphi, Greece," 2006, pp. 32.

Gantner, et al., Histamine H4 and H2 Receptors Control Histamine-Induced Interleukin-16 Release from Human CD8+ T Cells, The Journal of Pharmacology and Experimental Therapeutics, vol. 303, No. 1, pp. 300-307, 2002.

Grzybowska-Kowalczyk A., et al., "Distribution Pattern of Histamine H4 Receptor in Human Synovial Tissue from Patients with Rheumatoid Arthritis," Inflammation Research, 2007, vol. 56 (Suppl. 1), pp. S59-S60.

Gura, Systems for Identifying New Drugs Are Often Faulty, Cancer Models, Science, vol. 278, No. 5340, pp. 1041-1042.

Gutzmer, et al., "Histamine H4 Receptor Stimulation Suppresses IL-12p70 Production and Mediates Chemotaxis in Human Monocyte-derived Dendritic Cells," Journal of Immunology, 2005, vol. 174 (9), pp. 5224-5232.

Hartwig, et al., "Room-Temperature Palladium-Catalyzed Amination of Aryl Bromides and Chloride and Extended Scope of Aromatic C-N. Bond Formation with a Commercial Ligand," Journal of Organic Chemistry, 1999, vol. 64 (15), pp. 5575-5580.

Hartwig, et al., "Transition Metal Catalyzed Synthesis of Arylamines and Aryl Ethers from Aryl Halides and Triflates: Scope and Mechanism," Angewandte Chemie International Edition, 1998. 37, pp. 2046-2067.

Higuchi, et al., eds., Pro-drugs as Novels Delivery Systems, vol. 14, ACS Symposium Series, 1975, Table of Contents.

Honore, et al., "Interleukin-1 Alpha Beta Gene-Deficient Mice Show Reduced Nociceptive Sensitivity in Models of Inflammatory and Neuropathic Pain but not Post-Operative Pain," Behavioural Brain Research, 2006, vol. 167 (2), pp. 355-364.

Ikawa, et al., "Histamine H4 Receptor Expression in Human Synovial Cells Obtained from Patients Suffering from Rheumatoid Arthritis," Biological and Pharmaceutical Bulletin, 2005, vol. 28 (10), pp. 2016-2018.

International Search Report for Application No. PCT/US2009/042860, mailed on 16 Sep. 2009, 3 pages.

Jablonowska, et al., Distribution Pattern of Histamine H4 Receptor in Human Synovial Tissue from Patients with Rheumatoid Arthritis, 35th Meeting of the European Histamine Research Society in Delphi, Greece, Presentation 036.

Johnson, et al., Relationships Between Drug Activity in NCI Preclinical In Vitro and In Vivo models and Early Clinical Trials, British Journal of Cancer (2001) 64 (10): 1424-1431.

Joshi, et al., "Animal Models of Pain for Drug Discovery," Expert Opinion on Drug Discovery, 2006, vol. 1 (4), pp. 323-334.

Joshi, et al., "Involvement of the TTX-resistant Sodium Channel Nav 1.8 in Inflammatory and Neuropathic, but not Post-operative, Pain States," Pain, 2006, vol. 123 (1-2), pp. 75-82.

Kim, et al., "An Experimental Model for Peripheral Neuropathy Produced by Segmental Spinal Nerve Ligation in the Rat," Pain, 1992, vol. 50 (3), pp. 355-363.

Kiyomori, et al., "An Efficient Copper-Catalyzed Coupling of Aryl Halides with Imidazoles," Tetrahedron Letters, 1999, vol. 40, pp. 2657-2660.

Klapars, et al., "A General and Efficient Copper Catalyst for the Amidation of Aryl Halides and the N-Arylation of Nitrogen Heterocycles," Journal of the American Chemical Society, 2001, vol. 123, pp. 7727-7729.

Krueger, et al., "G Protein-Dependent Pharmacology of Histamine H3 Receptor Ligands: Evidence for Heterogeneous Active State Receptor Conformations," Journal of Pharmacology and Experimental Therapeutics, 2005, vol. 314 (1), pp. 271-281.

Kwong, et al., "Copper-Catalyzed Coupling of Alkylamines and Aryl Iodides: An Efficient System Even in an Air Atmosphere," Organic Letters, 2002, vol. 4, pp. 581-584.

Lazar-Molnar, E., "Signal-Transduction Pathways of Histamine Receptors" in: Histamine: Biology and Medical Aspects, Falus a., et al., eds., Spring Med Publishing Ltd., 2004, pp. 89-96.

Liu, et al., "Cloning and Pharmacological Characterization of a Fourth Histamine Receptor (H4) Expressed in Bone Marrow," Molecular Pharmacology, 2001, vol. 59, pp. 420-426.

Liu, et al., "Comparison of Human, Mouse, Rat, and Guinea Pig Histamine H4 Receptors Reveals Substantial Pharmacological Species Variation," Journal of Pharmacology and Experimental Therapeutics, 2001, vol. 299 (1), pp. 121-130.

Maslinska, et al., Toll-like Receptors (TLRs) and Histamine Receptor H4 in Articular Tissues of Patients with Rheumatoid Arthritis (RA), 34th Meeting of the European Histamine Research Society in Bled, Slovenia, 2005, Poster P-03.

Non-Final Office Action mailed Dec. 22, 2011 for U.S. Appl. No. 12/501,137.

Nguyen, et al., "Discovery of a Novel Member of the Histamine Receptor Family," Molecular Pharmacology, 2001, vol. 59 (3), pp. 427-433.

Oda, et al., "Molecular Cloning of Monkey Histamine H4 Receptor," Journal of Pharmacological Sciences, 2005, vol. 98 (3), pp. 319-322.

Parsons, et al., "Histamine and its Receptors," British Journal of Pharmacology, 2006, vol. 147 Suppl 1, pp. S127-S135.

Porreca, et al., "Antinociceptive Pharmacology of N-[[4-(4,5-Dihydro-1H-imidazol-2- yl)phenylmethyl]-242-[[(4- methoxy-2,6-dimethylphenyl)sulfonyl]methylaminojethoxyl-N-methylacetamide, Fumarate (LF22-0542), a Novel Nonpeptidic Bradykinin B1 Receptor Antagonist," Journal of Pharmacology and Experimental Therapeutics, 2006, vol. 318, pp. 195-205.

Robinson, et al., Medical Therapy of Inflammatory Bowel Disease for the $21^{st}$ Century, Eur. J. Suppl. 582, pp. 90-98, 1998.

Simone, et al., Oncology: Introduction, Cecil Textbook of Medicine, $20^{th}$ Edition, vol. 1. pp. 1004-1010, 1996.

Singh, et al, Immune Therapy in Inflammatory Bowel Disease and Models of Colitis, British Journal of Surgery, 88, pp. 1558-1569, 2001.

Silverman, "Prodrugs and Drug Delivery Systems," The Organic Chemistry of Drug Design and Drug Action pp. 352-400, 1992.

Smith, et al., Vogel's Textbook of Practical Organic Chemistry, 1989, Ed. 5, Longman Scientific & Technical.

Smith, et al., "Neuropathic Pain and the Electrophysiology and Pharmacology of Nerve Injury," Drug Development Research, 2001, vol. 54 (3), pp. 140-153.

Stark, H., "Recent Advances in Histamine H3/H4 Receptor Ligands," Expert Opinion in Therapeutic Patents, 2003, vol. 13 (6), pp. 851-865.

Sugahara, et al., "A Facile Copper-Catalyzed Ullmann Condensation: N-Arylation of Heterocyclic Compounds Containing an -NHCO- Moiety," Chemical & Pharmaceutical Bulletin, 1997, vol. 45, pp. 719-721.

Thurmond, et al., "A Potent and Selective Histamine H4 Receptor Antagonist with Anti-Inflammatory Properties," Journal of Pharmacology and Experimental Therapeutics, 2004, vol. 309, pp. 404-413.

Varga, et al., "Inhibitory Effects of Histamine H4 Receptor Antagonists on Experimental Colitis in the Rat," European Journal of Pharmacology, 2005, vol. 522, pp. 130-138.

Vinik, et al., "Diabetic Neuropathies," The Medical Clinics of North America, 2004, vol. 88 (4), pp. 947-999.

Vogel, H., Drug Discovery and Evaluation: Pharmacological Assays, 2nd Edition, Springer-Verlag Berlin Heidelberg, 2002, pp. 702-706.

Wolfe, et al., "Rational Development of Practical Catalysts for Aromatic Carbon-Nitrogen Bond Formation," Accounts of Chemical Research, 1998, vol. 13, pp. 805-818.

Wolfe, et al., "Simple, Efficient Catalyst System for the Palladium-Catalyzed Amination of Aryl Chlorides, Bromides, and Triflates," Journal of Organic Chemistry, 2000, vol. 65 (4), pp. 1158-1174.

Wolff, M., "Burger's Medicinal Chemistry and Drug Discovery," Principles and Practice, 1995, 975-977, 5th Ed, vol. 1, John Wiley & Sons.

Yamamoto, et al., "Palladium Catalyzed Conjugate 1,4-Addition of Organoboronic Acids to Alpha, Beta-Unsaturated Ketones," Chemistry Letters, 2006, vol. 35 (2), pp. 198-199.

Yang, et al., "Palladium-catalyzed Amination of Aryl Halides and Sulfonates," Journal of Organometallic Chemistry, 1999, vol. 576, pp. 125-146.

Zhu, et al., "Cloning, Expression, and Pharmacological Characterization of a Novel Human Histamine Receptor," Molecular Pharmacology, 2001, vol. 59 (3), pp. 434-441.

International Preliminary Report on Patentability and Written Opinion for Application No. PCT/US2009/042860, mailed on Nov. 9, 2010, 6 pages.

* cited by examiner

HETEROARYL-FUSED MACROCYCLIC PYRIMIDINE DERIVATIVES

CROSS-REFERENCE SECTION

This application claims priority to provisional application Ser. No. 61/050,400, filed May 5, 2008, which is incorporated herein by reference.

BACKGROUND OF THE INVENTION

1. Technical Field

The invention relates to heteroaryl-fused macrocyclic 2,4-diaminopyrimidine compounds, compositions comprising the compounds, methods for making the compounds, and methods of treating conditions and disorders using such compounds and compositions.

2. Description of Related Technology

Histamine modulates a number of physiological activities, acting through specific histamine receptors (reviewed in Parsons and Ganellin, British Journal of Pharmacology (2006) 147, S127-S135; Igaz and Hegyesi, in Histamine: Biology and Medical Aspects (2004), 89-96; Editor(s): A. Falus; Published S. Karger A G, Basel). Four histamine receptors have been identified as playing distinct physiological roles. These are the histamine $H_1$ receptor, the histamine $H_2$ receptor, the histamine $H_3$ receptor, and the histamine $H_4$ receptor. Compounds that modulate, or affect, the activity of these receptors may be used to treat diseases. For example, the well-known role of $H_1$ receptors in modulating allergic reaction has led to the clinical development of drugs that treat allergic rhinitis and other diseases by antagonizing the action of naturally-occurring, or endogenous, histamine in the body. Histamine $H_2$ receptor antagonists have been developed and proven clinically useful in treating diseases associated with excess stomach acidity. The histamine $H_3$ receptor is found predominantly on nerve terminals in the central nervous system (CNS) and the peripheral nervous system, i.e., periphery, and antagonists of this receptor have been documented in studies that benefit mammalian cognitive processes, improve wakefulness, suppress symptoms of allergic rhinitis, and suppress weight gain. The histamine $H_4$ receptor is the most recently identified histamine receptor and has been characterized as a distinct histamine receptor. The histamine $H_4$ receptor has been found in a number of mammalian tissues and has been determined to modulate a number of physiological processes, including immunological function.

By use of histamine $H_4$ ligands in animal disease models as well as in in vitro and ex vivo studies, the histamine $H_4$ receptor has been demonstrated to play an important role in various physiological and pathophysiological processes. Separately, in experiments with histamine $H_4$ deficient (knock out) animals and cells and tissues from such histamine $H_4$ deficient animals, the histamine $H_4$ receptor has been demonstrated to play an important role in various physiological and pathophysiological processes. Examples of diseases and disorders where histamine $H_4$ receptors have been found to play an important role include, for example, asthma, allergy, rheumatoid arthritis, and inflammation.

The activity of histamine $H_4$ receptors can be modified or regulated by the administration of histamine $H_4$ receptor ligands. The ligands can demonstrate antagonist, inverse agonist, or partial agonist activity.

Histamine $H_4$ ligands in different structural classes have been reviewed (Schwartz, Expert Opinion in Therapeutic Patents (2003) vol. 13, pp. 851-865). It would be beneficial to provide additional compounds demonstrating $H_4$ receptor-modulating activity that can be incorporated into pharmaceutical compositions useful for therapeutic methods.

BRIEF DESCRIPTION OF THE INVENTION

The application is directed to macrocyclic pyrimidine derivatives, particularly heteroaryl-fused macrocyclic 2,4-diaminopyrimidine derivatives, as well as compositions comprising and methods of using the same. Compounds of the invention can have the formula (I)

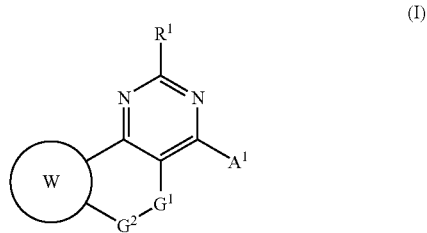

or a pharmaceutically acceptable, salt, ester, amide, or prodrug thereof, in which $R^1$ is selected from hydrogen, alkoxy, alkoxycarbonyl, alkyl, —(C=O)—NH-alkylene($NR^7R^8$), —(C=O)—($NR^7R^8$), carboxy, cyano, cyanoalkyl, cycloalkyl, fluoroalkyl, fluorocycloalkyl, hydroxyalkyl, $NH_2$, —NH(acyl), —NH(alkyl), —N(alkyl)$_2$, —NH(C=O) aryl, —NH-alkylene($NR^7R^8$), —NH(C=O)-alkylene ($NR^7R^8$), —$NR^7$(C=O)$NR^7R^8$, —NH-alkylene-heteroaryl, —NHOH, —$NHOCH_3$, —O-alkylene($NR^7R^8$), and piperazine; $G^1$ is selected from oxygen, sulfur, S(O), S(O)$_2$, $NR^7$ and alkylene; $G^2$ is selected from oxygen, sulfur, S(O), S(O)$_2$, $NR^7$, and alkylene; wherein each carbon of the alkylene and alkylene groups of $G^1$ and $G^2$ may be optionally substituted with one or more groups selected from acyl, acyloxy, alkenyl, alkoxy, alkoxyalkoxy, alkoxyalkyl, alkoxycarbonyl, alkyl, alkylsulfonyl, alkylthio, alkynyl, amido, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, fluorine, formyl, haloalkoxy, haloalkyl, halogen, hydroxy, hydroxyalkyl, mercapto, nitro, and oxo; provided that only one of $G^1$ or $G^2$ can be oxygen, sulfur, S(O), S(O)$_2$ or $NR^7$; W is an optionally substituted heteroaryl ring selected from the group consisting of

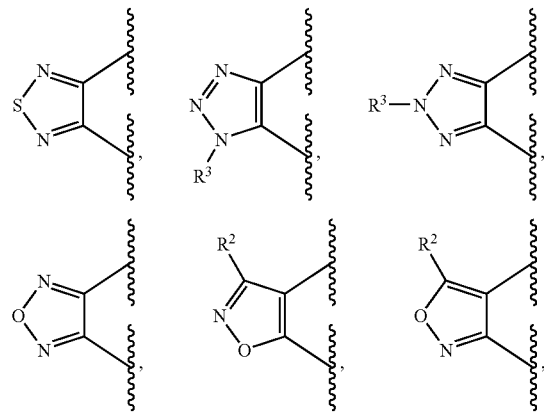

-continued

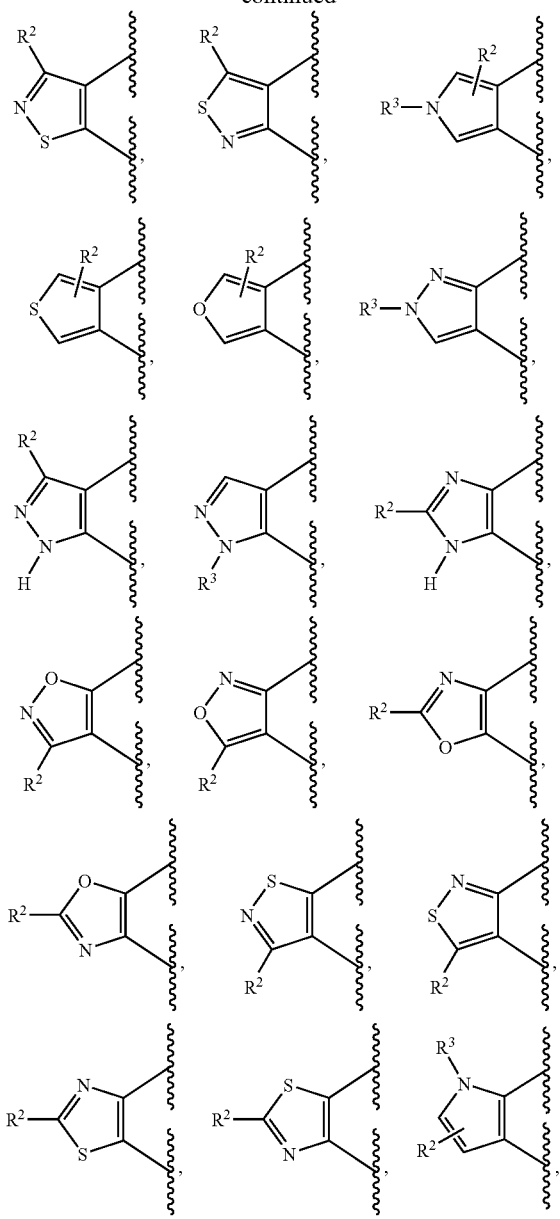

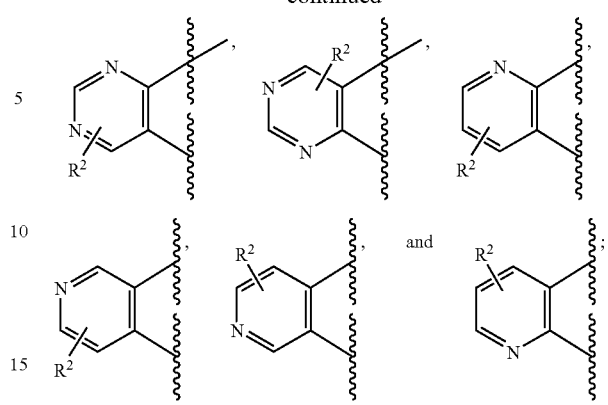

R² is hydrogen, acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, aryl, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, formyl, haloalkoxy, haloalkyl, halogen, hydroxy, hydroxyalkyl, mercapto, nitro, CONR⁷R⁸, NR⁷COalkyl, —NR⁷(C=O)Oalkyl, or O-aryl; R³ is hydrogen, alkyl, aryl, cyanoalkyl, cycloalkoxyalkyl, cycloalkyl, cycloalkylalkyl, fluoroalkyl, fluorocycloalkyl, or fluorocycloalkylalky; R⁴ is hydrogen, alkoxyalkyl, alkyl, cyanoalkyl, cycloalkoxyalkyl, cycloalkyl, cycloalkylalkyl, fluoroalkyl, fluorocycloalkyl, fluorocycloalkylalkyl, or hydroxyalkyl; R⁵ is alkoxyalkyl, fluoroalkyl, fluorocycloalkyl, fluorocycloalkylalkyl, or hydroxyalkyl;

R⁶ is hydrogen, acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluoroalkyl, fluorocycloalkyl, fluorocycloalkylalkyl, formyl, heteroaryl, heterocycle, hydroxy, or hydroxyalkyl;

R⁷ and R⁸ are each independently selected from acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluorocycloalkyl, fluorocycloalkylalkyl, heteroaryl, heterocycle, hydrogen, formyl, hydroxy, or hydroxyalkyl;

A¹ is a group of structure A² or A³; wherein A² is:

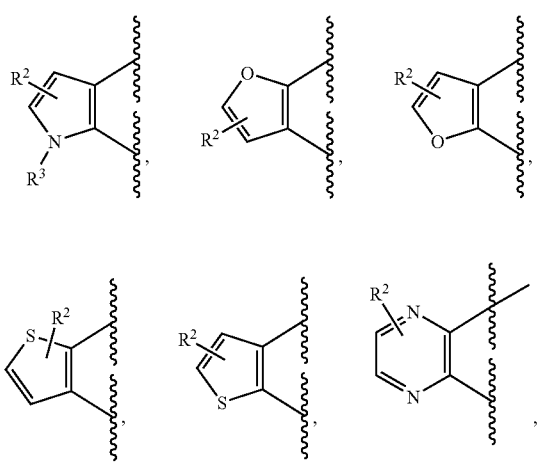

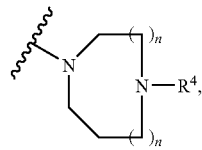   A

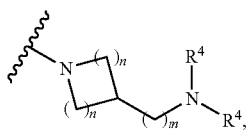   B

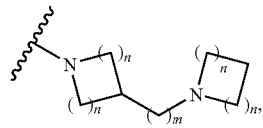   C

D
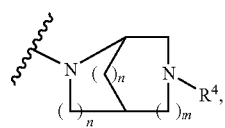
E
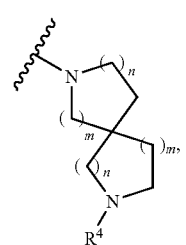
F
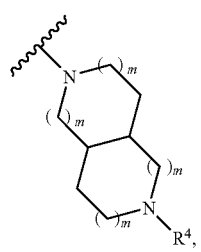
G
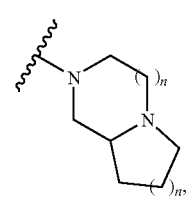
H
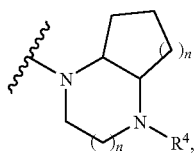
I
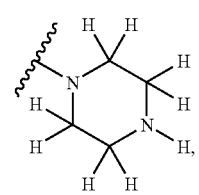
J
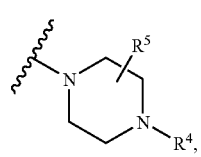
K
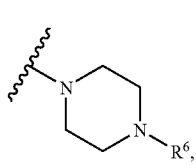
L
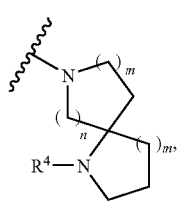
M
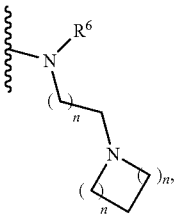
N
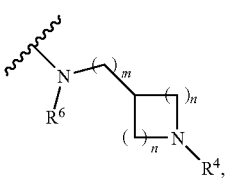
O
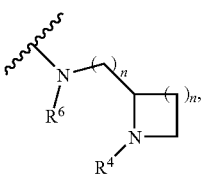
P
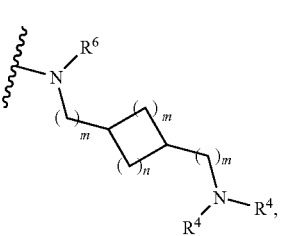
Q
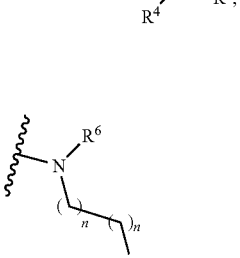
R
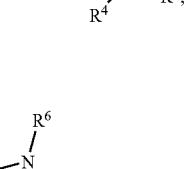

S
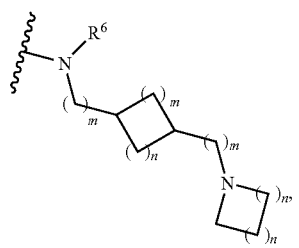
T
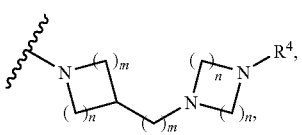
U
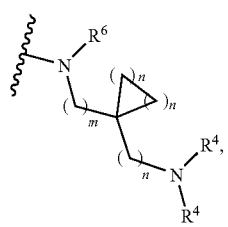
V
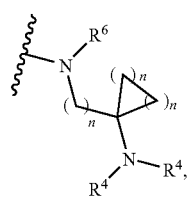
W
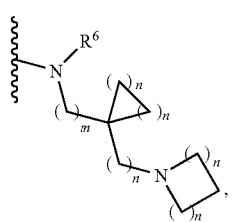
X
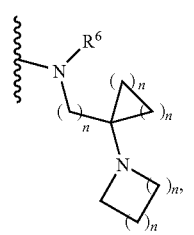
Y1
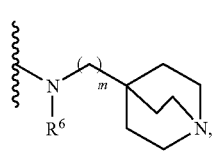
Y2
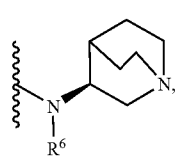
Y3
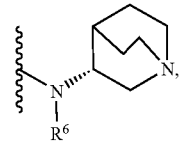
Y4
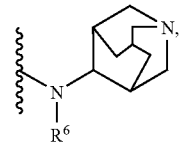
Y5
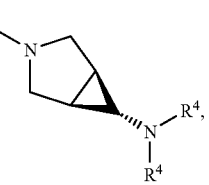
Y6
Y7
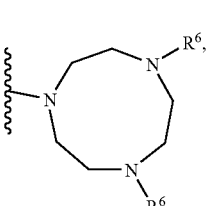
Y8
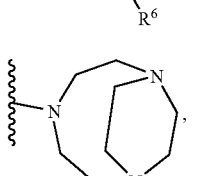
Y9
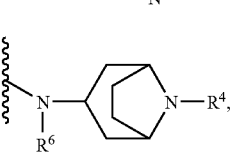
Y10
Y11
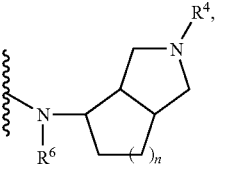

-continued
Y12
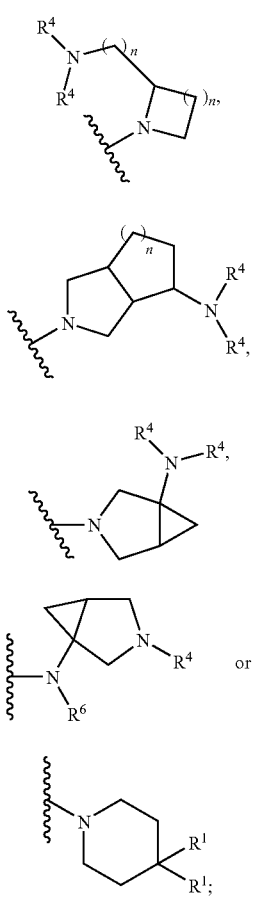
Y13
Y14
Y15 or
Y16
and A³ is
1M
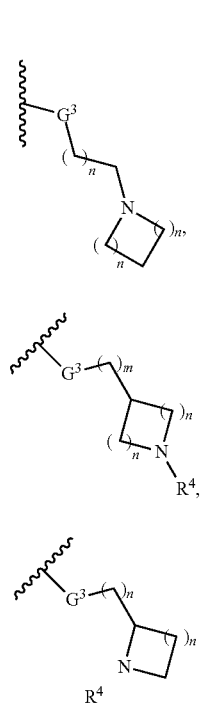
1N
1O
-continued
1P
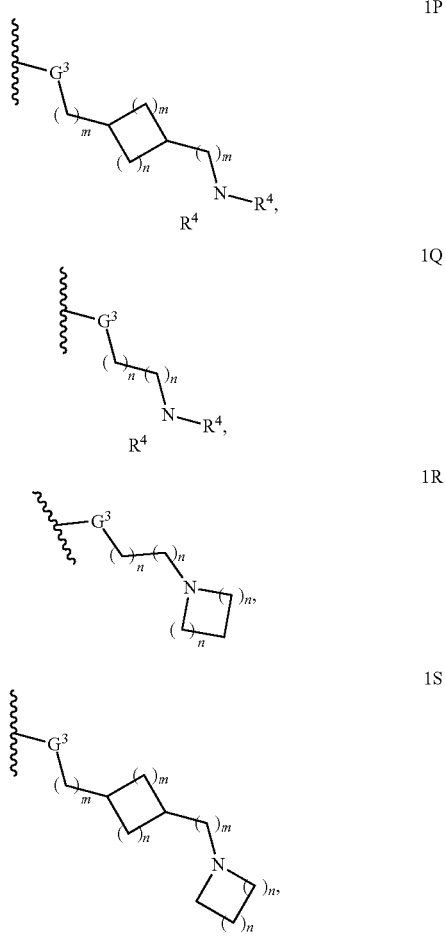
1Q
1R
1S
1U
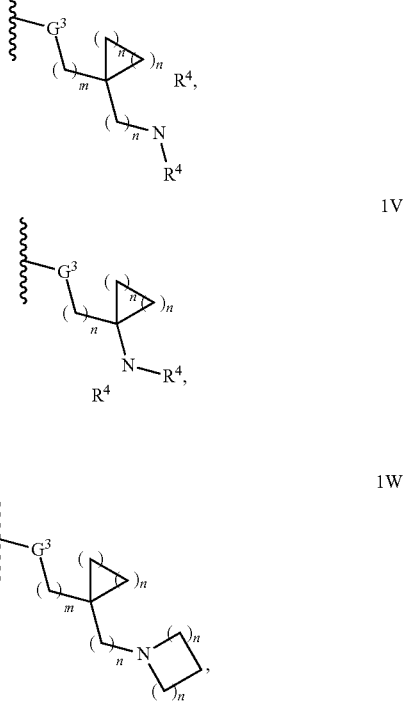
1V
1W

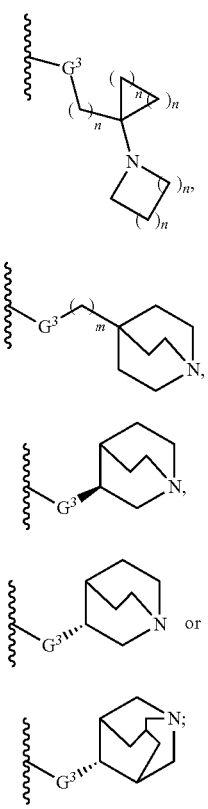

for which G³ can be O, S, S(O), or S(O)₂; n can be 1, 2, or 3; and m can be 0, 1, or 2; wherein each carbon atom of groups A¹ may be optionally substituted with one or more groups selected from acyl, acyloxy, alkenyl, alkoxy, alkoxyalkoxy, alkoxyalkyl, alkoxycarbonyl, alkyl, alkylsulfonyl, alkylthio, alkynyl, amido, carboxy, cyano, cyanoalkyl, cycloalkoxyalkyl, cycloalkyl, cycloalkylalkyl, fluorine, fluoroalkoxy, fluoroalkyl, fluorocycloalkyl, fluorocycloalkylalkyl, formyl, haloalkoxy, haloalkyl, hydroxy, hydroxyalkyl, mercapto, and nitro; with the proviso that when G¹ is CH₂ or CH₂CH₂ and G² is CH₂ and R¹ is NH₂, NHalkyl, or N(alkyl)₂, then A¹ is not a group of structure K.

Another aspect of the invention relates to pharmaceutical compositions comprising compounds of the invention.

Another aspect of the invention relates to a method of treating a mammal having a condition where modulation of histamine H₄ receptor activity is of therapeutic benefit. Such method can comprise administering to a subject having or susceptible to said disorder with a therapeutically effective amount of a compound of formula (I). The method also comprises administering a compound of formula (II), which is further described herein.

The compounds, compositions comprising the compounds, methods for making the compounds, and methods for using the compounds and compositions containing such compounds are further described herein.

DETAILED DESCRIPTION OF THE INVENTION

Definition of Terms

For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds, which can be isolated in a useful degree of purity from a reaction mixture.

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through a —C(=NH)— group, which also is defined as an imino group. Representative examples of alkoxyimino include, but are not limited to, (methoxy)imino, (ethoxy)imino and (tert-butoxy)imino.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —$NH_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, —$NR^7R^8$, ($NR^7R^8$)carbonyl, —$SO_2NR^7R^8$, —$NR^7(C=O)NR^7R^8$, —$NR^7(C=O)Oalkyl$, and $N(R^7)SO_2(R^8)$. Where the aryl group is a phenyl group, the number of substituents is 0, 1, 2, 3, 4, or 5. Where the aryl group is a bicyclic aryl, the number of substituents is 0, 1, 2, 3, 4, 5, 6, or 7. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —$C(=O)$— group.

The term "carboxy" as used herein means a —$CO_2H$ group.

The term "cyano" as used herein means a —CN group, attached to the parent molecular moiety through the carbon.

The term "cyanoalkyl" as used herein means a —CN group attached to an alkylene, appended to the parent molecular moiety through the alkylene group. Representative examples of "cyanoalkyl" include, but are not limited to, 3-cyanopropyl, and 4-cyanobutyl.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 10 carbons. Examples of cycloalkyl include cyclopropyl, cyclobutyl, cyclopentyl, cyclohexyl, cycloheptyl, and cyclooctyl. $C_3$-$C_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, carboxy, cyano, fluoroalkoxy, formyl, haloalkoxy, haloalkyl, halogen, hydroxy, hydroxyalkyl, mercapto, oxo, nitro, —$NR^7R^8$, ($NR^7R^8$)carbonyl, —$SO_2N(R^7)(R^8)$, and —$N(R^7)SO_2(R^8)$, wherein, $R^7$ and $R^8$ are defined herein.

The term "cycloalkoxyalkyl" as used herein means a cycloalkyl group, as defined herein, appended to the parent molecular moiety through an —O-alkyl- group, wherein alkyl is as defined herein. Representative examples of cycloalkoxylalkyl include, but are not limited to, cyclobutoxymethyl, cyclopentyloxymethyl, 2-(cyclopentyloxy)ethyl and cyclohexyloxymethyl.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. (C$_3$-C$_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through a alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" or "fluorine" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy and 2,2,2-trifluoroethoxy.

The term "fluorocycloalkyl" as used herein means a fluoro as defined herein, attached to a cycloalkyl moiety, attached to the parent molecular moiety through the cycloalkyl group. Representative examples of fluorocycloalkyl include, but are not limited to, 4-fluorocyclohexyl, 2,2-difluorocyclobutyl and the like.

The term "fluorocycloalkylalkyl" as used herein means a fluorocycloalkyl group as defined herein, attached to the parent molecular moiety through an alkyl group. Representative examples of fluorocycloalkylalkyl include, but are not limited to, (4-fluorocyclohexyl)methyl, (2,2-difluorocyclobutyl)methyl and the like.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The terms "heteroaryl" refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contain 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and one oxygen atom. The 5- or 6-membered heteroaryl is connected to the parent molecular moiety through any carbon atom or any nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, pyridazinonyl, pyridonyl, and pyrimidinonyl.

Heteroaryl groups of the invention, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —NR$^7$R$^8$, (NR$^7$R$^8$)carbonyl, —SO$_2$N(R$^7$)(R$^8$), and —N(R$^7$)SO$_2$(R$^8$). 5- or 6-membered heteroaryl rings are substituted with 0, 1, 2, 3, 4, or 5 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring contains zero, one, or two double bonds provided that the ring, when taken together with a substituent, does not tautomerize with a substituent to form an aromatic ring and one, two, three, or four heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, hexahydropyrrolo[3,4-b]pyrrol-1(2H)-yl, tetrahydro-1H-pyrrolo[3,4-b]pyridin-6(2H,7H,7aH)-yl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$^7$R$^8$, (NR$^7$R$^8$)carbonyl, —SO$_2$N(R$^7$)(R$^8$), —NR$^7$(C=O)NR$^7$R$^8$, —NR$^7$(C=O)Oalkyl, and —N(R$^7$)SO$_2$(R$^8$).

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, CH$_2$I$_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)—group.

The term "mercapto" as used herein means a —SH group.

The term "(NR$^7$R$^8$)" as used herein means both an R$^7$ and R$^8$ group, wherein R$^7$ and R$^8$ are each as defined for compounds of formula (I), are appended to the parent molecular moiety through a nitrogen atom. The "(NR$^7$R$^8$)" is appended to the parent molecular moiety through the nitrogen.

The term "(NR$^7$R$^8$)alkyl" as used herein means an —NR$^7$R$^8$ group, as defined herein, appended to the parent molecular moiety through an alkylene group, as defined herein. Representative examples of (NR$^7$R$^8$)alkyl include, but are not limited to, 2-(methylamino)ethyl, 2-(dimethylamino)ethyl, 2-(amino)ethyl, 2-(ethylmethylamino)ethyl, and the like.

The term "(NR$^7$R$^8$)carbonyl" as used herein means an —NR$^7$R$^8$ group, as defined herein, appended to the parent molecular moiety through a carbonyl group, as defined herein. Representative examples of (NR$^7$R$^8$)carbonyl include, but are not limited to, aminocarbonyl, (methylamino)carbonyl, (dimethylamino)carbonyl, (ethylmethylamino)carbonyl, and the like.

The term "(NR$^7$R$^8$)sulfonyl" as used herein means a —NR$^7$R$^8$ group, as defined herein, appended to the parent molecular moiety through a sulfonyl group, as defined herein. Representative examples of (NR$^7$R$^8$)sulfonyl include, but are not limited to, aminosulfonyl, (methylamino)sulfonyl, (dimethylamino)sulfonyl and (ethylmethylamino)sulfonyl.

The term "—N(R$^7$)SO$_2$(R$^8$)" as used herein means an amino group attached to the parent moiety to which is further appended with a R$^7$ group as defined herein, and a SO$_2$ group to which is appended an (R$^8$) group as defined herein. Representative examples of —N(R$^7$)SO$_2$(R$^8$) include, but are not limited to, N-methylmethanesulfonamide.

The term "—SO$_2$(NR$^7$R$^8$)" as used herein means a NR$^7$R$^8$ group attached to a SO$_2$ group, appended to the parent moiety through the sulfonyl group. Representative examples of —SO$_2$(NR$^7$R$^8$) include, but are not limited to (dimethylamino)sulfonyl and N-cyclohexyl-N-methylsulfonyl.

The term "nitro" as used herein means a —NO$_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (CBz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-C=O)$_2$O, a diaryl anhydride, for example as represented by (aryl-C=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —S(O)$_2$—group.

Antagonists are ligands that block receptor activation by an agonist. In the case of the histamine H$_4$ receptor, a histamine H$_4$ receptor antagonist blocks activation of the histamine H$_4$ receptor by a histamine H$_4$ receptor agonist such as the endogenous agonist ligand histamine. Inverse agonists are ligands that block receptor activation more generally: they block intrinsic activation of a receptor that occurs in the absence of an agonist activation by an agonist, and also block receptor activation by an agonist. Partial agonists are ligands that bind to receptors but only partially activate the receptor; in so doing, partial agonists compete with full agonists and block full activation of the receptor. In the case of the histamine H$_4$ receptor, the endogenous agonist histamine is a full agonist.

Compounds of the Invention

Compounds of the invention can have the formula (I) as described in the Summary of the Invention.

Preferred compounds are those in which G$^1$ is alkylene, wherein alkylene is —CH$_2$—; G$^2$ is alkylene, wherein alkylene is —CH$_2$—CH$_2$—; and R$^1$ is selected from the groups consisting of NH$_2$, —NH(acyl), —NH(alkyl), —N(alkyl)$_2$, —NH(C=O)aryl, —NH-alkylene(NR$^7$R$^8$), —NH(C=O)-alkylene(NR$^7$R$^8$), —NR$^7$(C=O)NR$^7$R$^8$, —NH-alkyleneheteroaryl, —NHOH, —NHOCH$_3$. Those compounds preferably have A$^1$ as a group of structure A$^2$, in which A$^2$ is selected from

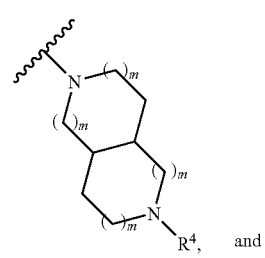

and

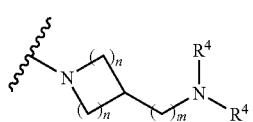

and where W can be selected from

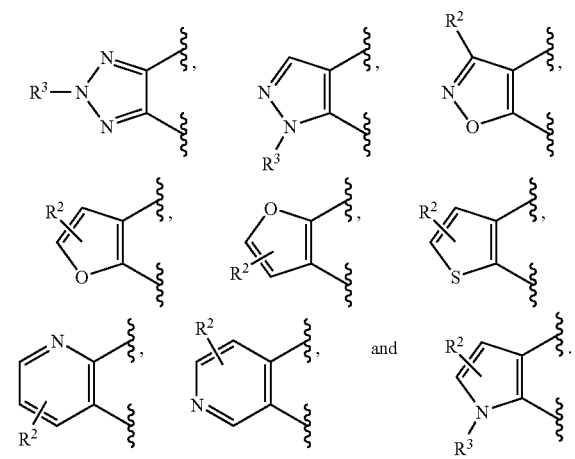

Exemplary compounds of the invention include, but are not limited to:

4-octahydro-6H-pyrrolo[3,4-b]pyridin-6-yl-6,7-dihydro-5H-thieno[2',3':6,7]cyclohepta[1,2-d]pyrimidin-2-amine;
4-[(3R)-3-aminopyrrolidin-1-yl]-6,7-dihydro-5H-thieno[2',3':6,7]cyclohepta[1,2-d]pyrimidin-2-amine;
4-[(3R)-3-(methylamino)pyrrolidin-1-yl]-6,7-dihydro-5H-thieno[2',3':6,7]cyclohepta[1,2-d]pyrimidin-2-amine;
4-octahydro-6H-pyrrolo[3,4-b]pyridin-6-yl-6,7-dihydro-5H-furo[2',3':6,7]cyclohepta[1,2-d]pyrimidin-2-amine;
9-methyl-4-octahydro-6H-pyrrolo[3,4-b]pyridin-6-yl-6,7-dihydro-5H-furo[2',3':6,7]cyclohepta[1,2-d]pyrimidin-2-amine;
4-[(3R)-3-aminopyrrolidin-1-yl]-9-methyl-6,7-dihydro-5H-furo[2',3':6,7]cyclohepta[1,2-d]pyrimidin-2-amine;
4-octahydro-6H-pyrrolo[3,4-b]pyridin-6-yl-6,7-dihydro-5H-furo[3',2':6,7]cyclohepta[1,2-d]pyrimidin-2-amine;
4-[(3R)-3-aminopyrrolidin-1-yl]-8-methyl-5,6,7,8-tetrahydropyrazolo[3',4':6,7]cyclohepta[1,2-d]pyrimidin-2-amine;
8-tert-butyl-4-octahydro-6H-pyrrolo[3,4-b]pyridin-6-yl-5,6,7,8-tetrahydropyrazolo[3',4':6,7]cyclohepta[1,2-d]pyrimidin-2-amine;
4-[(3R)-3-(methylamino)pyrrolidin-1-yl]-8-phenyl-5,6,7,8-tetrahydropyrazolo[3',4':6,7]cyclohepta[1,2-d]pyrimidin-2-amine;
9-bromo-4-octahydro-6H-pyrrolo[3,4-b]pyridin-6-yl-6,7-dihydro-5H-thieno[2',3':6,7]cyclohepta[1,2-d]pyrimidin-2-amine;
4-octahydro-6H-pyrrolo[3,4-b]pyridin-6-yl-9-phenyl-6,7-dihydro-5H-thieno[2',3':6,7]cyclohepta[1,2-d]pyrimidin-2-amine;
4-[(3R)-3-aminopyrrolidin-1-yl]-6,7-dihydro-5H-pyrido[3',2':6,7]cyclohepta[1,2-d]pyrimidin-2-amine;
4-[(3R)-3-aminopyrrolidin-1-yl]-10-methyl-6,7-dihydro-5H-isoxazolo[5',4':6,7]cyclohepta[1,2-d]pyrimidin-2-amine;
4-[(4aR,7aR)-octahydro-6H-pyrrolo[3,4-b]pyridin-6-yl]-6,7-dihydro-5H-thieno[2',3':6,7]cyclohepta[1,2-d]pyrimidin-2-amine; or a pharmaceutically acceptable salt thereof.

Other preferred compounds are those in which $G^1$ is alkylene, wherein alkylene is $-CH_2-$; $G^2$ is alkylene, wherein alkylene is $-CH_2-$; and $R^1$ is selected from the groups consisting of $NH_2$, $-NH(acyl)$, $-NH(alkyl)$, $-N(alkyl)_2$, $-NH(C=O)aryl$, $-NH-alkylene(NR^7R^8)$, $-NH(C=O)-alkylene(NR^7R^8)$, $-NR^7(C=O)NR^7R^8$, $-NH-alkylene-heteroaryl$, $-NHOH$, $-NHOCH_3$; in which $A^1$ is a group of structure $A^2$, and $A^2$ is selected from

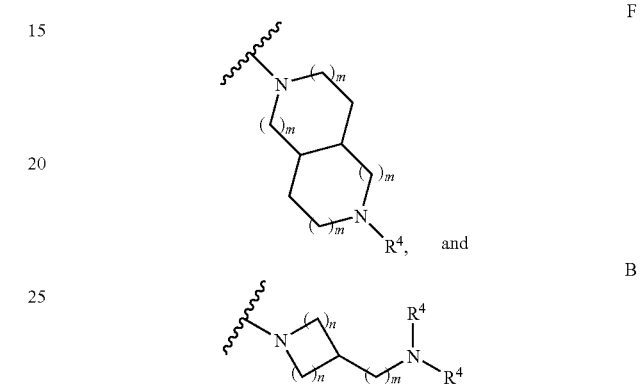

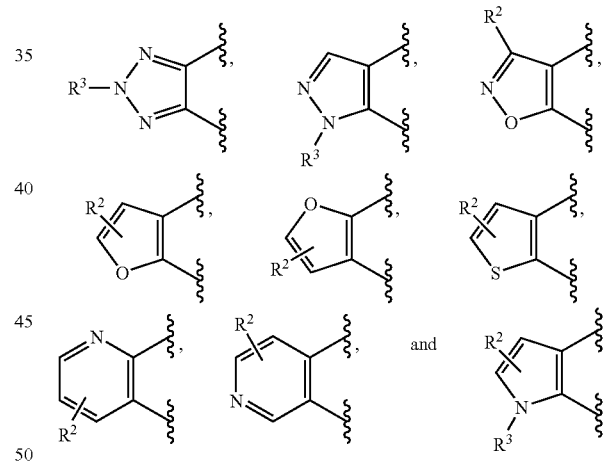

and W can be selected from

Compounds of formula (I) the invention can exist as pharmaceutical composition comprising a pharmaceutically acceptable carrier.

The practice of assigning names to chemical compounds from structures, and of assigning chemical structures from given chemical names is well known to those of ordinary skill in the art.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials that contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Fumiss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes and cyclohexanes may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Methods of the Invention

Compounds and compositions of the invention are useful for modulating the histamine $H_4$ receptor, particularly by histamine $H_4$ receptor antagonism, partial agonism, or inverse agonism. In particular, the compounds and compositions of the invention can be used for treating and preventing disorders modulated by the histamine $H_4$ receptor. Typically, such disorders can be ameliorated by modulating histamine $H_4$ receptors in a mammal, preferably by administering a compound or composition of the invention, either alone or in combination with another active agent, for example, as part of a therapeutic regimen.

Certain substituted heteroaromatic fused pyrimidine compounds, including but not limited to those specified as compounds of the invention, demonstrate the ability to affect histamine $H_4$ receptor activity, and particularly for histamine $H_4$ receptor antagonism. Such compounds can be useful for the treatment and prevention of a number of histamine $H_4$ receptor-mediated diseases or conditions. Compounds of the invention demonstrate such activity and have the formula (I), as previously defined herein.

There is also disclosed a method of treating a mammal having a condition where modulation of histamine $H_4$ receptor activity is of therapeutic benefit, said method comprising administering to a subject having or susceptible to said disorder with a therapeutically effective amount of a compound of the formula (I), or a pharmaceutically acceptable salt, ester, amide, or prodrug thereof, as previously in the Summary of the Invention and Detailed Description of the Invention herein.

There is also disclosed a method of treating a mammal having a condition where modulation of histamine $H_4$ receptor activity is of therapeutic benefit. The method comprises administering to a subject having or susceptible to said disorder a therapeutically effective amount of a compound of the formula (I), as previously defined.

The method is particularly beneficial when the condition or disorder is asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, or spinal cord injury pain.

In particular, it is particularly beneficial to administer compounds of formula (I) for the prevention and treatment of asthma.

It also is particularly beneficial to administer compounds of formula (I) for the prevention and treatment of inflammation.

It also is particularly beneficial to administer compounds of formula (I) for the prevention and treatment of pain. More particularly, it is beneficial to administer compounds of formula (I) for prevention and treatment of inflammatory pain. Compounds of formula (I) also demonstrate therapeutic benefit in treating and preventing non-inflammatory pain. In particular, compounds of formula (I) can be administered for treatment and prevention of neuropathic pain.

It is intended that this invention includes a method to treat pain comprising administering a histamine $H_4$ receptor ligand of formula (I) according to claim 1, or a salt, ester, amide, or prodrug thereof, in combination with a histamine $H_1$ antagonist; a histamine $H_2$ antagonist, histamine $H_3$ antagonist; a modulator of TNF-α, an anti-inflammatory corticocosteroids; a 5-lipoxygenase inhibitor; a leukotriene antagonist; a LTB4 antagonist; a non-steroidal anti-inflammatory drug; a COX-2 inhibitor; a β-adrenergic receptor agonist; an anti-nociceptive opiate agonist, an anti-nociceptive alpha adrenergic agonist, a TRPV1 antagonist, a nicotinic acetylcholine receptor agonist, a CB-1 agonist; a CB-2 agonist; a P2X7 antagonist; a metabotropic glutamate receptor antagonist; or an adrenergic agonist, or a combination thereof.

Particularly preferred are compounds of formula (I) for the method, include, but are not limited to, 4-octahydro-6H-pyrrolo[3,4-b]pyridin-6-yl-6,7-dihydro-5H-thieno[2',3':6,7]cyclohepta[1,2-d]pyrimidin-2-amine; 4-[(3R)-3-aminopyrrolidin-1-yl]-6,7-dihydro-5H-thieno[2',3':6,7]cyclohepta[1,2-d]pyrimidin-2-amine; 4-[(3R)-3-(methylamino)pyrrolidin-1-yl]-6,7-dihydro-5H-thieno[2',3':6,7]cyclohepta[1,2-d]pyrimidin-2-amine; or 4-octahydro-6H-pyrrolo[3,4-b]pyridin-6-yl-6,7-dihydro-5H-furo[2',3':6,7]cyclohepta[1,2-d]pyrimidin-2-amine.

The present application also comprises a method of treating a mammal having a condition where modulation of histamine H$_4$ receptor activity is of therapeutic benefit, said method comprising administering to a subject having or susceptible to said disorder with a therapeutically effective amount of a compound of the formula (II)

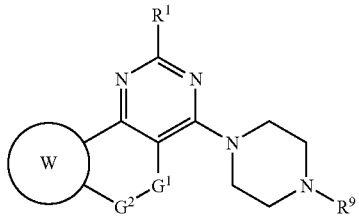
(II)

or a pharmaceutically acceptable, salt, ester, amide, or prodrug thereof, in which R$^1$ is selected from hydrogen, alkoxy, alkoxycarbonyl, alkyl, —(C=O)—NH-alkylene(NR$^7$R$^8$), —(C=O)—(NR$^7$R$^8$), carboxy, cyano, cyanoalkyl, cycloalkyl, fluoroalkyl, fluorocycloalkyl, hydroxyalkyl, NH$_2$, —NH(acyl), —NH(alkyl), —N(alkyl)$_2$, —NH(C=O) aryl, —NH-alkylene(NR$^7$R$^8$), —NH(C=O)-alkylene (NR$^7$R$^8$), —NR$^7$(C=O)NR$^7$R$^8$, —NH-alkylene-heteroaryl, —NHOH, —NHOCH$_3$, —O-alkylene(NR$^7$R$^8$), and piperazine; G$^1$ is selected from oxygen, sulfur, S(O), S(O)$_2$, NR$^7$ and alkylene; G$^2$ is selected from oxygen, sulfur, S(O), S(O)$_2$, NR$^7$, and alkylene; wherein each carbon of the alkylene and alkylene groups of G$^1$ and G$^2$ may be optionally substituted with one or more groups selected from acyl, acyloxy, alkenyl, alkoxy, alkoxyalkoxy, alkoxyalkyl, alkoxycarbonyl, alkyl, alkylsulfonyl, alkylthio, alkynyl, amido, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, fluorine, formyl, haloalkoxy, haloalkyl, halogen, hydroxy, hydroxyalkyl, mercapto, nitro, and oxo; provided that only one of G$^1$ or G$^2$ can be oxygen, sulfur, S(O), S(O)$_2$ or NR$^7$; W represents an optionally substituted heteroaryl ring selected from the group consisting of

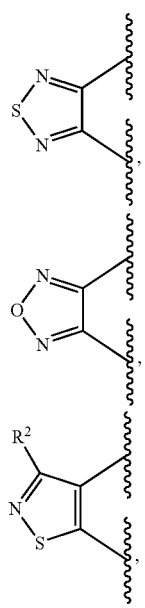

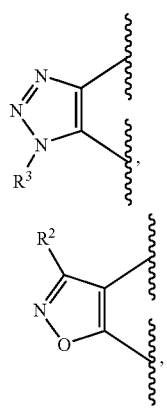

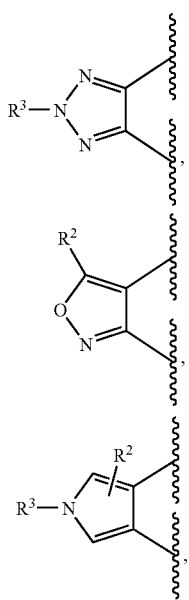

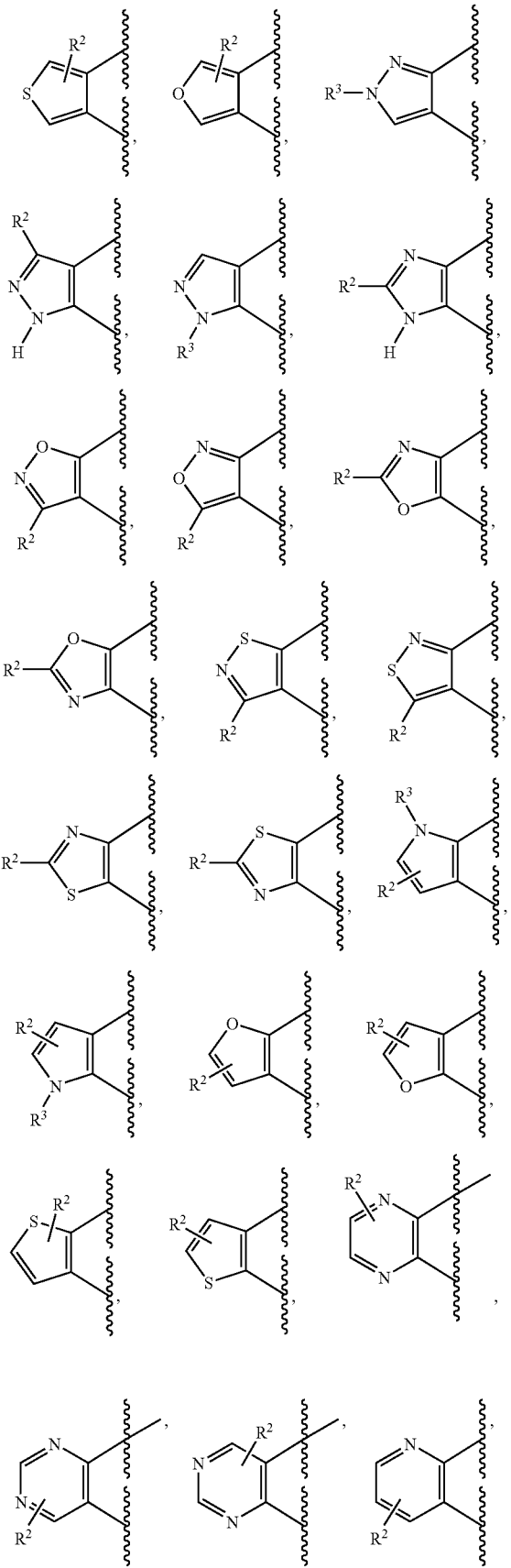

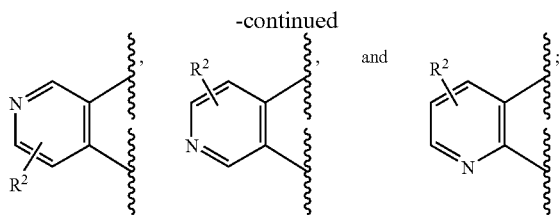

$R^2$ is selected from hydrogen, acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, aryl, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, formyl, haloalkoxy, haloalkyl, halogen, hydroxy, hydroxyalkyl, mercapto, nitro, $CONR^7R^8$, $NR^7COalkyl$, $-NR^7(C=O)Oalkyl$, or O-aryl; $R^3$ is selected from hydrogen, alkyl, aryl, cyanoalkyl, cycloalkoxyalkyl, cycloalkyl, cycloalkylalkyl, fluoroalkyl, fluorocycloalkyl, or fluorocycloalkylalky; $R^7$ and $R^8$ are each independently selected from acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluorocycloalkyl, fluorocycloalkylalkyl, heteroaryl, heterocycle, hydrogen, formyl, hydroxy, or hydroxyalkyl; and $R^9$ is selected from hydrogen, acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluoroalkyl, fluorocycloalkyl, fluorocycloalkylalkyl, formyl, heteroaryl, heterocycle, hydroxy, or hydroxyalkyl.

It is intended that the condition or disorder is asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, osteoarthritic pain, post-surgical pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, or spinal cord injury pain, or a combination thereof.

As an important consequence of the ability of the compounds of the invention to modulate the effects of histamine $H_4$ receptors in cells, the compounds described for the method of the invention can affect physiological processes in humans and animals. In this way, the compounds and compositions of formula (I) are useful for treating and preventing diseases and disorders modulated by histamine $H_4$ receptors. Typically, treatment or prevention of such diseases and disorders can be effected by modulating the histamine $H_4$ receptors in a mammal, by administering a compound or composition of the invention, either alone or in combination with another active agent as part of a therapeutic regimen.

Compounds of formula (I) can be administered to a subject having such a disorder or susceptible to such disorders in a therapeutically effective amount. The compounds are particularly useful for a method of treating a mammal having a condition where modulation of histamine $H_4$ receptor activity is of therapeutic benefit, wherein the method is accomplished by administering a therapeutically effective amount of a compound of formula (I) to a subject having, or susceptible to, such a disorder.

Compounds useful for the method of the invention, include but not limited to those specified in the examples, and possess an affinity for the histamine $H_4$ receptor. Such compounds therefore may be useful for the treatment and prevention of diseases or conditions related to histamine $H_4$ modulation. Examples of such diseases or conditions are, for example, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain. The ability of histamine $H_4$ receptor modulators, and consequently the compounds of the invention, to prevent or treat such disorders is demonstrated by evidence and examples found in references which follow.

Histamine $H_4$ receptor ligands have utility in treatment of a number of diseases and conditions, including asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

The histamine $H_4$ receptor, or gene message coding for the histamine $H_4$ receptor (detected as cDNA by reverse transcriptase polymerase chain amplification (RTPCR) of cellular messenger (mRNA)) has been detected in a number of cells and tissues critically affected in disease conditions. For example, the histamine $H_4$ receptor plays a critical role in inflammation, in autoimmune disorders such as rheumatoid arthritis, and in disorders of the immune system. For example, the histamine $H_4$ receptor has been detected in cells of the immune system and in organs of the immune system: neutrophils, eosinophils, basophils, dendritic cells, mast cells, bone marrow, thymus, spleen, brain. For examples, see Liu, et al.

Molecular Pharmacology (2001) vol. 59 pp. 420-426; de Esch, et al. Trends in Pharmacological Sciences Vol. 26 No. 9 pp. 462-469; Oda, et al. Journal of the Pharmocological Society (2005) vol. 98, pp. 319-322; Zhu, et al. Molecular Pharmacology, (2001), v. 59, pp. 434-441; Gutzmer, et al. Journal of Immunology (2005) vol. 174 pp. 5224-5232; Coge, et al., Biochemical and Biophysical Research Communications (2001) vol. 284, pp. 301-309.

Histamine $H_4$ receptor is found at high (compared to normal) levels in disease tissues in rheumatoid arthritis, see for example, Grzybowska-Kowalczyk, et al. Inflammation Research (2007), 56, Supplement 1, S1-S2; Maslinska, et al. $34^{th}$ Meeting of the European Histamine Research Society in Bled, Slovenia 2005 poster number 3; Jablonowska, et al. $35^{th}$ Meeting of the European Histamine Research Society in Delphi, Greece (May 10-13, 2006) presentation O36; Ikawa, et al. Biol. Pharm. Bull. (2005) vol. 28(10) pp. 2016-2018.

The role of histamine $H_4$ receptors in allergy, asthma, and allergic airway inflammation is shown by the finding that transgenic mice without histamine $H_4$ receptors are resistant to the development of disease in an animal model of asthma. The observation that a selective synthetic $H_4$ ligand elicits the same benefit in the asthma model also supports the benefits of $H_4$ ligands in treatment of disease. For example, see Dunford, et al. The Journal of Immunology (2006) vol. 176, pp. 7062-7070.

General reviews and papers on the role of histamine receptor in disease include Akdis and Simons European Journal of Pharmacology (2006) vol. 533 pp. 69-76; de Esch, et al. Trends in Pharmacological Sciences Vol. 26 No. 9 pp. 462-469; Thurmond, et al. Journal of Pharmacology and Experimental Therapeutics (2004) vol. 309 pp. 404-413; Buckland, et al. British Journal of Pharmacology (2003) 140, 1117-1127. The utility for histamine $H_4$ receptor ligands in cancer is supported by the finding that the $H_4$ receptor has been found expressed on mammary cell carcinoma tissues, as reported by Maslinska, et al. $34^{th}$ Meeting of the European Histamine Research Society in Bled, Slovenia (May 11-15, 2005) presentation. Histamine $H_4$ receptor activation was found to exert a proliferative effect in cancer tissues, Cianchi, et al. Clinical Cancer Research (2005) vol. 11(19) pp. 6807-6815. In gastritis and gastric lesions, histamine $H_4$ ligands were found to reduce the lesions induced by administration of indomethacin in vivo: Coruzzi, et al. Jablonowska, et al. $35^{th}$ Meeting of the European Histamine Research Society in Delphi, Greece (May 10-13, 2006) presentation O44. In colitis, histamine $H_4$ ligands were found to reduce the lesions induced by administration of trinitrobenzesulfonic acid in vivo: Varga, et al. European Journal of Pharmacology (2005) vol. 522 pp. 130-138; Fogel, et al. $35^{th}$ Meeting of the European Histamine Research Society in Delphi, Greece (May 10-13, 2006) presentation P32. In itch and pruritis, the benefit of histamine $H_4$ receptor ligands has been shown by Bell, et al. British Journal of Pharmacology (2004) vol. 142, pp. 374-380.

The invention also relates to a new use of the compounds of the invention to treat histamine $H_4$ receptor ligands to treat pain, including distinctly different types of pain, including inflammatory pain, chemically induced pain, pain resulting from surgery, pain resulting from burns, pain resulting from osteoarthritis, non-inflammatory pain, and neuropathic pain. Neuropathic pain is distinct from other types of pain (e.g. inflammatory pain) in that it can develop in response to previous or ongoing tissue, nerve injury, or diabetes, but it persists long after signs of the original injury or damage have disappeared. The usefulness of histamine $H_4$ receptor ligands in treating pain has been demonstrated (Coruzzi, et al., *Eur. J. Pharmacol.* 2007, 563, 240-244).

Neuropathic pain is associated with allodynia, hyperalgesia, or causalgia (Dworkin Clinical Journal of Pain (2002) vol. 18(6) pp. 343-9). Allodynia is the perception of pain following a stimulus that would not normally be painful. Hyperalgesia is an enhanced response to a mildly noxious stimulus. Causalgia is described as a chronic burning pain that shows persistence in the absence of obvious noxious stimuli.

Neuropathic pain is not well treated with current therapies and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell Expert Opinion on Emerging Drugs (2005) vol. 10(1), pp. 95-108; Vinik and Mehrabyan Medical Clinics of North America (2004), vol. 88(4), pp. 947-999; Dray, Urban, and Dickenson Trends in Pharmacological Sciences (1994) vol. 15(6) pp. 190-7; Dworkin Clinical Journal of Pain (2002) vol. 18(6) pp. 343-9. A number of animal models of neuropathic pain that can be used to assess the ability of the compounds of the invention to treat neuropathic pain exist and are further discussed inter alia. Representative compounds of the invention are effective in treatment of neuropathic pain. Representative compounds of the invention are also effective in treating other types of pain, non-inflammatory pain, post surgical pain, and inflammatory pain.

Neuropathic pain is a description that encompasses more specific names of pain that are sub-categories of neuropathic pain (Dworkin Clinical Journal of Pain (2002) vol. 18(6) pp. 343-9) including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

In addition to neuropathic pain, there are other types of pain that are not inflammatory or not due to ongoing inflammation, including osteoarthritis pain, cancer pain, and visceral pain. A general review of animal models of pain is found in Joshi and Honore, Expert Opinion in Drug Discovery (2004) 1, pp. 323-334.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 5 to about 500 micromoles/kg of body weight. For purposes of oral administration, more preferable doses can be in the range of from about 30 to about 500 micromoles/kg body weight. If desired, the effective daily dose can be divided into multiple doses for purposes of administration; consequently, single dose compositions may contain such amounts or submultiples thereof to make up the daily dose.

Methods for Preparing Compounds of the Invention

The compounds of the invention can be better understood in connection with the following synthetic schemes and methods that illustrate a means by which the compounds can be prepared.

Abbreviations which have been used in the descriptions of the schemes and the examples that follow are: Boc for t-butyloxycarbonyl; n-BuLi for n-butyllithium, DMAP for 4-(dimethylamino)pyridine, DMF for N,N-dimethylformamide; DMSO for dimethyl sulfoxide; EDTA for ethylenediaminetetraacetic acid; Et$_3$N for triethylamine; EtOAc for ethyl acetate; HPLC for high pressure liquid chromatography; IPA for isopropyl alcohol; MCPBA for 3-chloroperoxybenzoic acid; Me for methyl; MeOH for methanol; Ms for methanesulfonyl; Pd for palladium; PPA for polyphosphoric acid, tBu for tert-butyl; TEA for triethylamine; TFA for trifluoroacetic acid; THF for tetrahydrofuran; Tf represents trifluoromethane sulfonyl; Tris for trishydroxymethylaminomethane; and Ts for para-toluenesulfonyl; dba for dibenzylidine acetone, rt for "room temperature" or ambient temperature suitably ranging 17-30° C. As identifiers of compounds available from descriptions reported in the literature or available commercially, CAS numbers may be used; CAS numbers are identifier numbers assigned to compounds by Chemical Abstracts Service of the American Chemical Society, and are well known to those of ordinary skill in the art.

The compounds of this invention can be prepared by a variety of synthetic procedures. Representative procedures are shown in, but are not limited to, Schemes 1-12.

Scheme 1

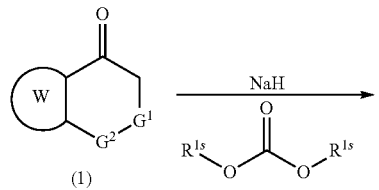

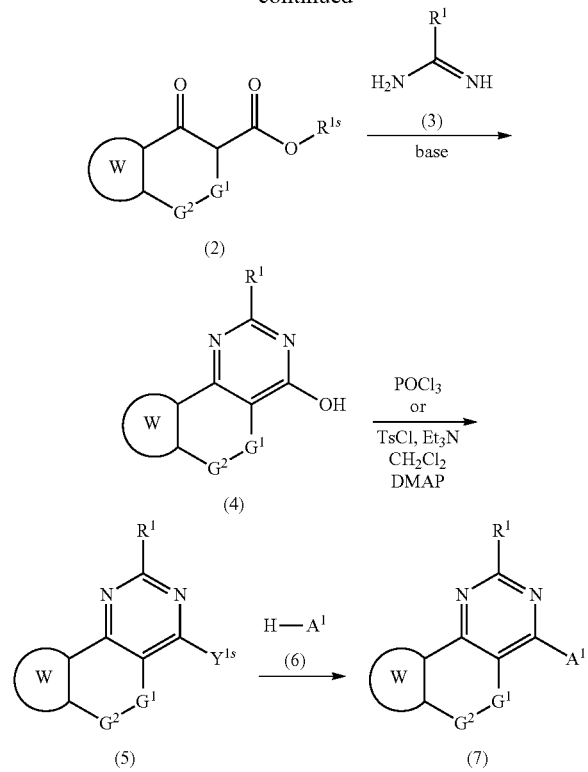

Compounds of formula (7), wherein $R^1$, W, $A^1$, $G^1$ and $G^2$ are defined in formula (I) may be prepared as outlined in Scheme 1. Ketones of formula (1), which are synthesized through the methods outlined herein, when treated with sodium hydride, followed by treatment with either a carbonate such as dimethyl carbonate, or a chloroformate such as ethyl chloroformate, will provide keto-ester containing compounds of formula (2), wherein $R^{1s}$ is lower alkyl. Compounds of formula (2) when treated with a compound of formula (3), such as guanidine nitrate, in the presence of a base such as potassium carbonate under heated conditions in a solvent such as N,N-dimethylformamide will provide compounds of formula (4). Compounds of formula (4) can exist as shown in the structure in Scheme 1 or in a tautomeric form. Compounds of formula (4) when treated with a chlorinating reagent such as but not limited to phosphous(V) oxychloride (POCl$_3$), with or without heating as needed, will provide compounds of formula (5), wherein $Y^{1s}$ is Cl. Alternatively, compounds of formula (4) may also be treated with reagents such as para-toluensulfonyl chloride, methylsulfonyl chloride or trifluoromethanesulfonyl chloride in the presence of a base such as triethylamine in a solvent such as pyridine or chloroform to provide compounds of formula (5) wherein $Y^{1s}$ is O—SO$_2$—R', wherein R' is lower alkyl, lower fluoroalkyl or aryl. Compounds of formula (5), wherein $Y^{1s}$ is Cl or —O—SO$_2$—R', when treated with compounds of formula (6), wherein (6) contains a primary or secondary nitrogen atom and H is a hydrogen atom on said nitrogen atom, under heated conditions in the presence or absence of a base such as triethylamine or diisopropyethylamine, in a solvent such as ethanol, 2-methoxyethanol, toluene or acetonitrile, will provide compounds of formula (7).

Compounds of formula (7) wherein $R^1$ is H and W, $A^1$, $G^1$ and $G^2$ are defined in formula (I) may be prepared by treating a compound of formula (2) with thiourea with heating in the presence of a base such as sodium methoxide in a solvent such as methanol, followed by reduction of the resulting product using a reagent such as Raney nickel to provide compounds of formula (4) wherein $R^1$ is H. Compounds of formula (4) wherein $R^1$ is H can be treated according to the method above to provide compounds of formula (7) wherein $R^1$ is H.

Compounds of formula (7), may be further treated according to conditions known to one skilled in the art to alter functional groups contained with in the compound, for example, the removal of a protecting group such as Boc or hydrolysis of an ester group that will generate compounds of the present invention or used within the scope of other schemes described herein.

Compounds of formula (6) that contain two different nitrogen atoms may selectively react with compounds of formula (5) to provide one isomer of formula (7). Such selectivity may be the result of substitution or protecting groups attached to one of the nitrogen atoms. Alternatively, compounds of formula (6) that contain two different N—H groups may react with compounds of formula (5) in a non-selective manner wherein a mixture of two different compounds of formula (7) are obtained from the reaction. Mixtures of compounds of formula (7) are generally separated by methods known to one skilled in the art, such as silica based column chromatography, selective recrystallization, or both.

(8), and aminoalcohols and aminothiols wherein the nitrogen atom is protected with synthetic protecting group such as a t-butoxycarbonyl group, which are obtained either from commercial sources or synthesized through the methods outlined herein, can be treated with a base such as sodium hydride, then treated with compounds of formula (5), wherein $Y^{1s}$ is Cl, p-toluenesulfonate or methanesulfonate, and then heated to provide compounds of formula (7). Alternative bases such as potassium tert-butoxide, potassium hydride, and potassium carbonate may also be employed. More generally, alcohols and thiols of formula (8) are described in the scientific literature and may be prepared by those or ordinary skill in the art of organic synthesis.

Compounds of formula (7), may be further reacted according to conditions known to those of ordinary skill in the art of organic synthesis to alter functional groups. For example, the removal of a protecting group such as Boc or hydrolysis of an ester group that will generate compounds of the present invention or be further transformed within the scope of other schemes described herein.

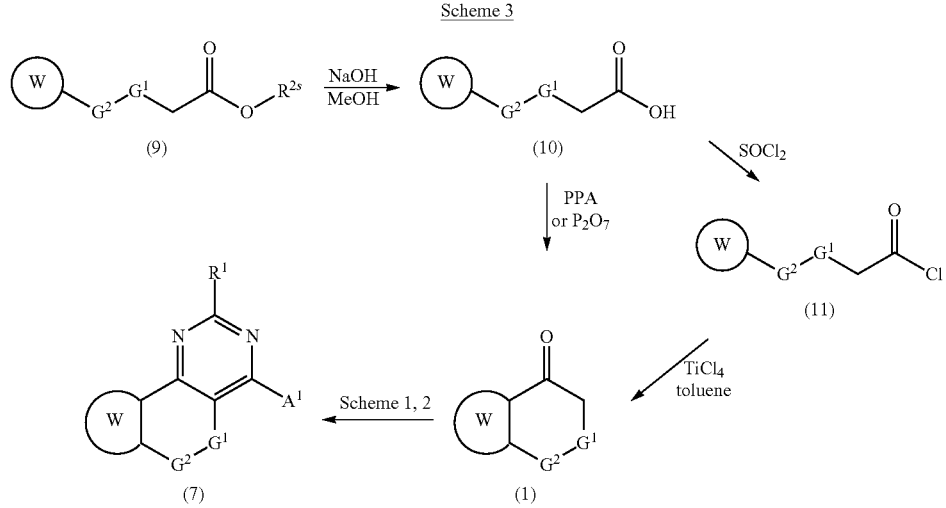

Scheme 3

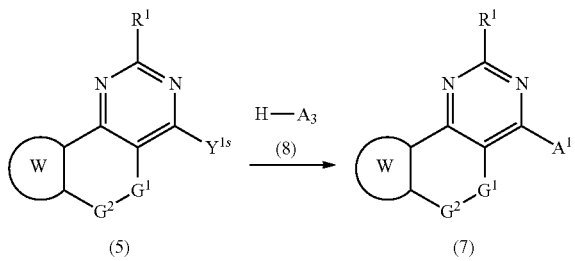

Scheme 2

Compounds of formula (7), wherein $R^1$, W, $A^1$, $G^1$ and $G^2$ are defined in formula (I) may be prepared as outlined in Scheme 2 from compounds of formula (5), the preparation of which is shown in Scheme 1. Alcohols and thiols of formula Compounds of formula (7), which are representative of compounds of the present invention wherein $R^1$, W, $A^1$, $G^1$ and $G^2$ are as defined in formula (I), may be prepared as outlined in Scheme 3. Compounds of formula (9), wherein $R^{2s}$ is lower alkyl or benzyl as obtained from commercial sources or prepared by those of ordinary skill in the art of organic synthesis, when treated with a base such as sodium hydroxide in a mixture of aqueous alcohol such as aqueous methanol or ethanol will provide compounds of formula (10). Compounds of formula (10) when heated in the presence of an acid such as polyphosphoric acid or heated in the presence of $P_2O_5$ (phosphorus pentoxide), will provide compounds of formula (1). Alternatively, compounds of formula (10) when treated with thionyl chloride under heated conditions will provide compounds of formula (11). Compounds of formula (10) can also be transformed to compounds of formula (11) by treatment with oxalyl chloride in the presence of a catalytic amount of 4-(dimethylamino)pyridine at room temperature in a solvent such as dichloromethane. Compounds of formula (11) when heated in the presence of a Lewis acid such as aluminum trichloride in a solvent such as toluene or carbon disulfide or tin (II) chloride in a solvent such as dichloromethane will provide compounds of formula (1). The compounds of formula (1) can be treated according to the methods outlined in Schemes 1 or 2 to provide compounds of formula (7), which are representative of compounds of the present invention.

Scheme 4

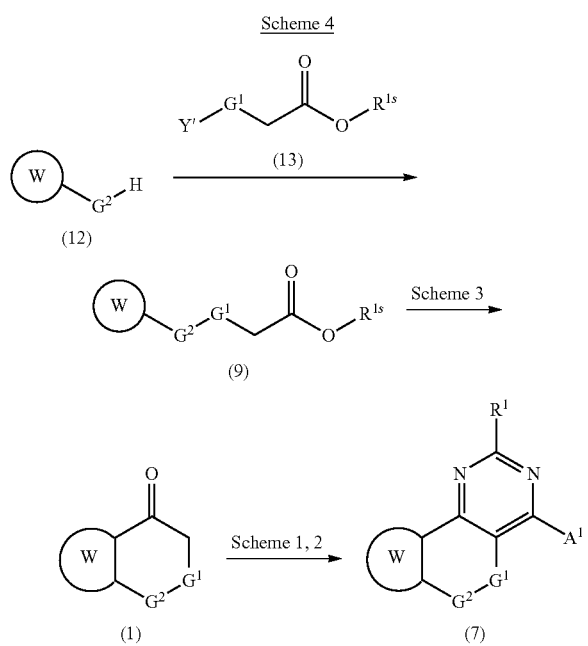

Compounds of formula (7), which are representative of compounds of the present invention wherein $R^1$, W and $A^1$ are defined in formula (I), $G^1$ is alkylene, and $G^2$ is O, S, may be prepared as outlined in Scheme 4. Compounds of formula (12), wherein $G^2$ is O, S, when treated with an ester of formula (13) wherein $R^{1s}$ is lower alkyl, $G^1$ is alkylene, and wherein Y' is chloro, bromo, iodo or methanesulfonate, in the presence of a base such as potassium carbonate, triethylamine or sodium hydride, in a solvent such as acetone, dichloromethane, tetrahydrofuran or N,N-dimethylformamide, will provide compounds of formula (9). Compounds of formula (9) can be cyclized according to the conditions described in Scheme 3 to provide compounds of formula (1). Compounds of formula (1) when processed as outlined in Schemes 1 or 2 will provide compounds of formula (7), which are representative of compounds of the present invention.

Scheme 5

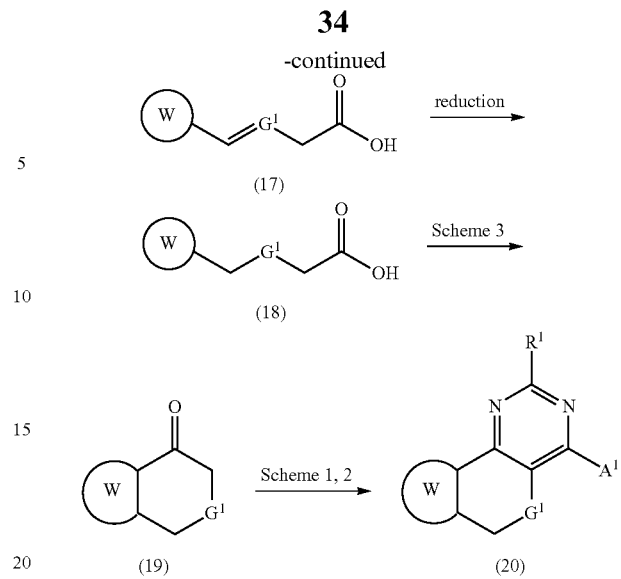

Compounds of formula (20) which are representative of compounds of the present invention wherein $R^1$, W and $A^1$ are as defined in formula (I), and $G^1$ is alkylene, may be prepared as outlined in Scheme 5. Compounds of formula (14) when treated with a compound of formula (15) that has been pretreated with a base such as sodium hydride in a solvent such as tetrahydrofuran or dimethyl sulfoxide, will provide compounds of formula (16). Compounds of formula (16) when treated with the base will provide compounds of formula (17). Compounds of formula (17) when treated with a catalyst such as but not limited to 5-10% palladium on carbon in a solvent such as but not limited to ethanol under an atmosphere of hydrogen will provide compounds of formula (18). Compounds of formula (18) can be cyclized according to the conditions described in Scheme 3 to provide compounds of formula (19). Compounds of formula (19) when subjected to conditions outlined in Schemes 1 or 2 will provide compounds of formula (20) that are representative of compounds of the present invention.

Scheme 6

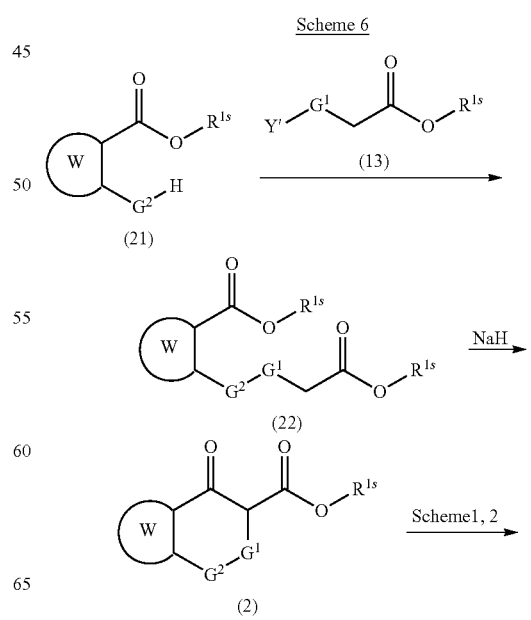

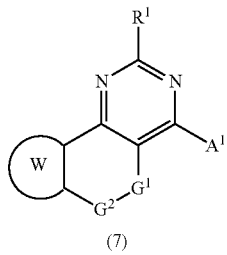

Compounds of formula (7), which are representative of compounds of the present invention wherein $R^1$, W and $A^1$ have been defined in formula (I), wherein $G^1$ is alkylene, and wherein $G^2$ is O or S, may be prepared as outlined in Scheme 6. Compounds of formula (21), wherein $R^{1s}$ is lower alkyl, $G^2$ is O or S when treated with a compound of formula (13) wherein $G^1$ is $C_{1-5}$ alkylene, $R^{1s}$ is lower alkyl, and wherein $Y'$ is a leaving group such as chloro, bromo, iodo or methanesulfonate, in the presence of a base such as potassium carbonate, triethylamine or sodium hydride, in a solvent such as acetone, dichloromethane, N,N-dimethylformamide or tetrahydrofuran, will provide compounds of formula (22). Compounds of formula (22) when treated with a base such as sodium hydride in a solvent such as tetrahydrofuran or N,N-dimethylformamide will provide compounds of formula (2). Compounds of formula (2) when treated as outlined in Scheme 1 or 2 will provide compounds of formula (7), which are representative of compounds of the present invention wherein $G^1$ is alkylene and $G^2$ is O or S.

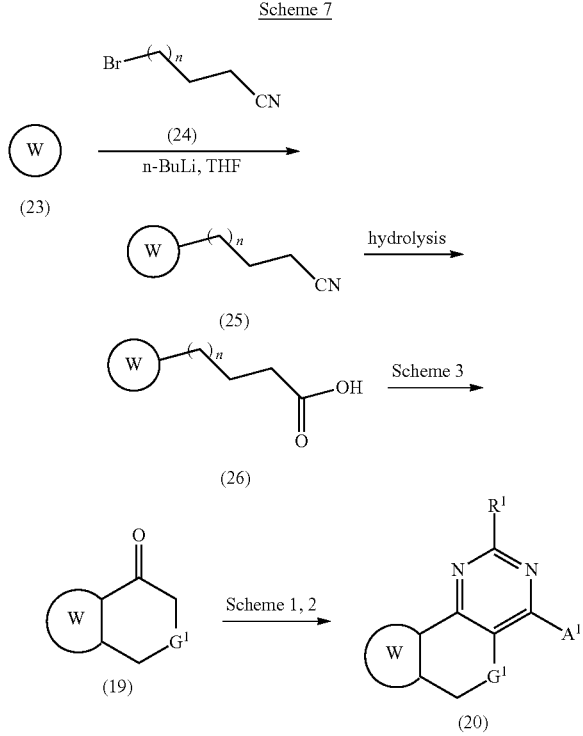

Compounds of formula (20) which are representative of compounds of the present invention wherein $R^1$, W and $A^1$ are as defined in formula (I), and $G^1$ is alkylene, may be prepared as outlined in Scheme 7. Compounds of formula (23) could be deprotonated with base such n-BuLi in a solvent such as tetrahydrofuran and treated with compounds of the formula (24) to provide compounds of formula (25). Compounds of formula (25) when hydrolyzed, will provide compounds of formula (26). Compounds of formula (26) can be cyclized according to the conditions described in Scheme 3 to provide compounds of formula (19). Compounds of formula (19) when subjected to conditions outlined in Schemes 1 or 2 will provide compounds of formula (20), which are representative of compounds of the present invention.

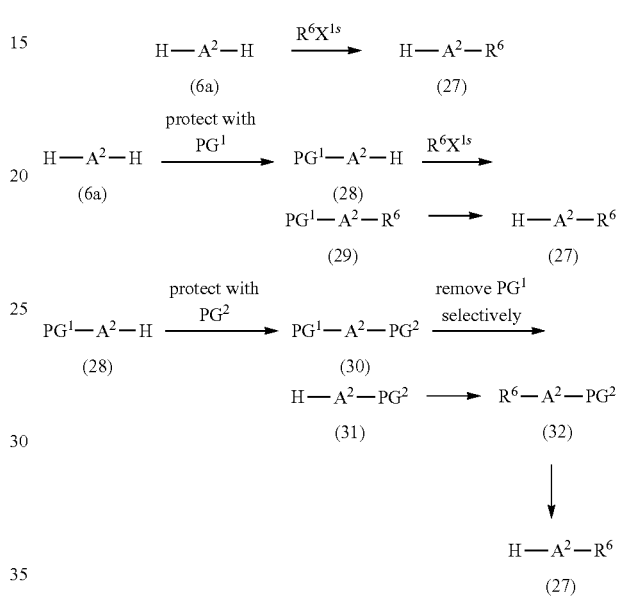

As outlined in Scheme 8, compounds of formula (6a) may contain two amine groups. The amine groups of compounds of formula (6a) may be either primary or secondary and can be used directly in Schemes 1 or Scheme 2 to provide compounds of formula (7). Alternatively, compounds of formula (6a), which contain two N—H groups, may be treated with an appropriate reagent such as $R^6$—$X^{1s}$, wherein $X^{1s}$ is a leaving group such as chlorine, bromine, iodine, mesylate or triflate, to provide compounds of formula (27) wherein one of the two N—H groups is substituted with $R^6$. Substituting compounds of formula (27) for compounds of formula (6) in the procedures outlined in Scheme 1 will provide compounds of formula (7) that are representative of the present invention.

Furthermore, compounds of formula (6a) that contain two amine groups may be treated with a reagent which will introduce a nitrogen protecting group ($PG^1$) on one of the amine groups. Some typical examples of common nitrogen protecting groups include but are not limited to benzyl, tert-butoxycarbonyl, benzyloxycarbonyl, or acetyl which are introduced by treating amines of formula (6a) with 1 equivalent of an appropriate reagent such as benzyl bromide, di-tert-butyl dicarbonate, benzyl chloroformate or acetic anhydride, respectively, to provide mono-protected diamines of formula (28). Mono-amine protected compounds of formula (28) can be further treated with an appropriate reagent such as $R^6$—$X^{1s}$, wherein $R^6$ is defined in formula (I) and $X^{1s}$ is a leaving group such as chlorine, bromine, iodine, mesylate or triflate, to provide compounds of formula (29). Compounds of formula (29) can be deprotected to provide compounds of formula (27) which can then be used to replace compounds of formula (6) in the procedures outlined in Scheme 1 to provide compounds of formula (7) which are representative of compounds of the present invention. Common conditions used for the deprotection of compounds of formula (29) to provide compounds of formula (27) include but are not limited to the following: catalytic hydrogenation conditions (e.g. in the presence of palladium on carbon in a solvent such as ethanol under an atmosphere of hydrogen); acidic conditions (e.g. treatment with aqueous hydrochloric acid), or basic hydrolysis conditions (e.g. treatment with aqueous sodium hydroxide and heat).

Alternatively, mono-protected diamines of formula (28) may be treated with an appropriate aldehyde or ketone under condition of reductive amination to provide diamines of formula (29). Conditions commonly used for reductive amination include treatment of an amine (28) with an aldehyde or ketone in the presence of sodium cyanoborohydride or sodium triacetoxyborohydride.

Mono-protected compounds of formula (28) can be treated with a second protecting group (PG$^2$) to provide di-protected compounds of formula (30). In di-protected compounds of formula (30), it is preferred that the choice of protecting groups is such that the protecting group PG$^1$ can be removed selectively without removing PG$^2$. Selective deprotection of PG$^1$ from compounds of formula (30) provide compounds of formula (31). Mono-protected compounds of formula (31) can be treated with an appropriate reagent such as R$^6$—X$^{1s}$, wherein R$^6$ is as defined in formula (I) and X$^{1s}$ is a leaving group such as chlorine, bromine, iodine, mesylate or triflate, to provide compounds of formula (32). Alternatively, mono-protected compounds of formula (31) when treated with an appropriate aldehyde or ketone under condition of reductive amination will provide compounds of formula (32). Compounds of formula (32) can be deprotected to provide compounds of formula (27).

Scheme 9

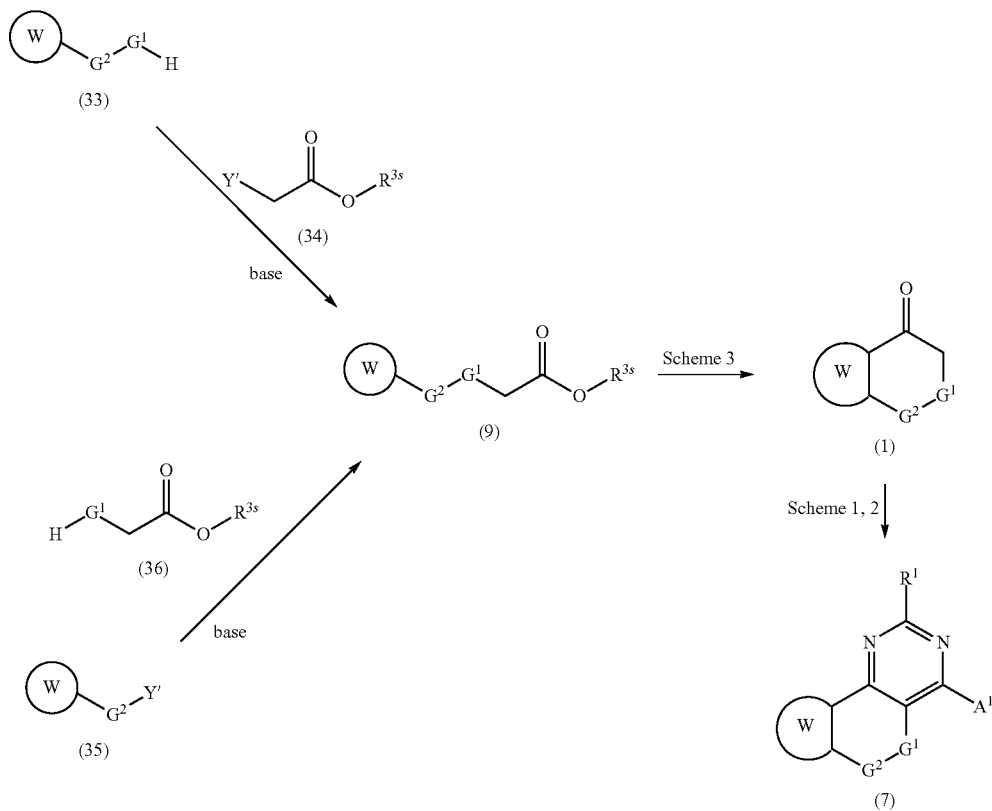

Compounds of formula (7), which are representative of compounds of the present invention wherein R$^1$, W and A$^1$ are defined in formula (I), G$^2$ is alkylene, and G$^1$ is O or S may be prepared as outlined in Scheme 9. Compounds of formula (33), wherein G$^1$ is O or S and G$^2$ is alkylene, can be treated with a base such as sodium hydride in a solvent such as N,N-dimethylformamide, followed by an ester of formula (34) wherein Y' is chloro, bromo, iodo or methanesulfonate, and wherein R$^{3s}$ can be H or alkyl, to provide compounds of formula (9) wherein R$^{3s}$ can be H or alkyl. Compounds of formula (35), wherein G$^2$ is alkylene, and Y' is leaving group such as chloro, bromo, iodo or methanesulfonate, can be treated with an ester of formula (36), wherein G$^1$ is S, and wherein R$^{3s}$ can be H or alkyl, in the presence of a base such as sodium hydride, sodium hydroxide or triethyl amine in a solvent such as N,N-dimethylformamide or methanol to provide compounds of formula (9) wherein R$^{3s}$ can be H or alkyl. Compounds of formula (9) can be cyclized according to the conditions described in Scheme 3 to provide compounds of formula (1). Compounds of formula (1) when processed as outlined in Schemes 1 or 2 will provide compounds of formula (7), which are representative of compounds of the present invention.

Scheme 10

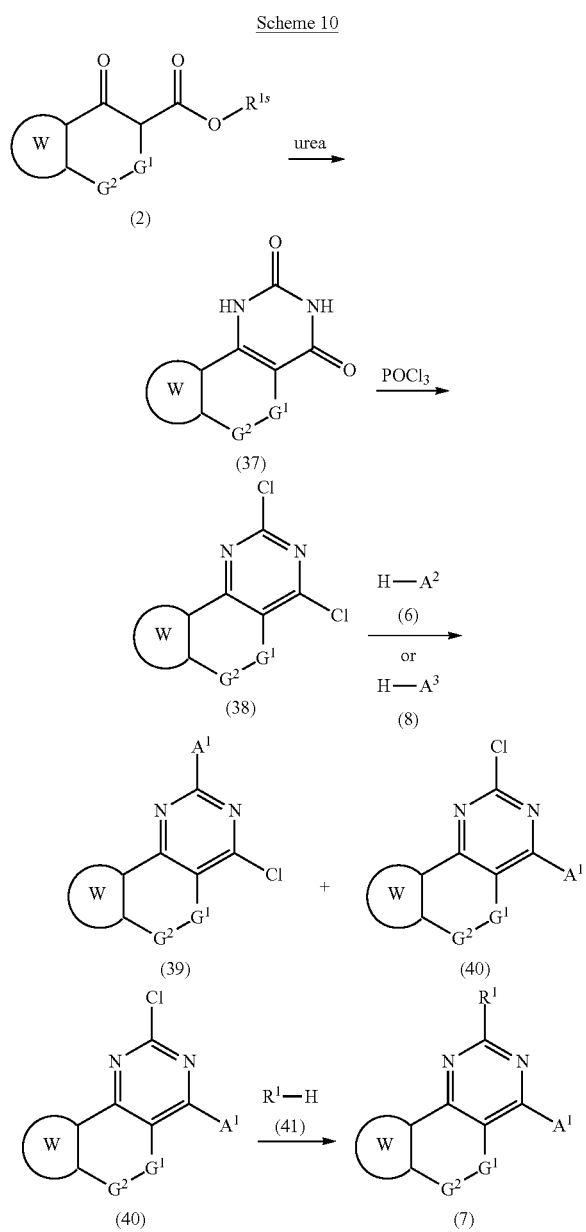

Compounds of formula (7), which are representative of compounds of the present invention wherein $R^1$, W, $G^1$, $G^2$ and $A^1$ are defined in formula (I), may be prepared as outlined in Scheme 10. Esters of formula (2), prepared as described in the above schemes, can be treated with an excess of urea and heated at 150-190° C. to provide compounds of formula (37). Compounds of formula (37) can exist as shown in the structure in Scheme 10 or in a tautomeric form. Compounds of formula (37) can be treated with phosphorous(V) oxychloride ($POCl_3$) with heating to provide compounds of formula (38). Compounds of formula (38) can be treated with compounds of formula (6), wherein (6) contains a primary or secondary nitrogen atom and H is a hydrogen atom on said nitrogen atom, under heated conditions in the presence or absence of a base such as triethylamine or diisopropyethylamine, in a solvent such as ethanol, 2-methoxyethanol, toluene or acetonitrile, to provide a mixture of compounds of formula (39) and formula (40). Alternatively, compounds of formula (8) can be treated with a base such as sodium hydride or potassium carbonate in a solvent such as tetrahydrofuran or N,N-dimethylformamide and then treated with a compound of formula (38) to provide a mixture of compounds of formula (39) and formula (40). Compounds of formula (39) and formula (40) can be separated by methods known to those skilled in the art, such as chromatography on silica gel or selective crystallization. Compounds of formula (40) can be reacted with a compound of formula (41), wherein $R^1$ is defined in formula (I), and compound (41) contains an alcohol or a primary or secondary nitrogen atom and H is a hydrogen atom on said oxygen or nitrogen atom, under heated conditions in the presence or absence of a base such as triethylamine, diisopropyethylamine or sodium hydride, in a solvent such as ethanol, 2-methoxyethanol, tetrahydrofuran, toluene, N,N-dimethylformamide or acetonitrile, to provide compounds of formula (7).

Compounds of formula (40) can also be treated with a catalyst such as [1,1'-bis(diphenylphosphino)ferrocene] dichloropalladium (II) complex with dichloromethane under an atmosphere of carbon monoxide in the presence of an alcohol such as methanol in the presence of a base such as triethyl amine while heating to provide compounds of formula (7) wherein $R^1$ is —(C=O)$OR^{1s}$, wherein $R^{1s}$ is lower alkyl. Compounds of formula (7) wherein $R^1$ is —(C=O)$OR^{1s}$ can be treated with an aqueous base such as 1 M sodium hydroxide in the presence of a solvent such as methanol to provide compounds of formula (7) wherein $R^1$ is —(C=O)OH. Compounds of formula (7) wherein $R^1$ is —(C=O)OH can be coupled with amines under conditions known to those of ordinary skill in the art to provide compounds If formula (7) wherein $R^1$ is selected from —(C=O)—($NR^7R^8$) and —(C=O)—NH— alkylene($NR^7R^8$).

Compounds of formula (40) can also be treated with a reagent such as zinc cyanide in the presence of a catalyst such as tetrakis(triphenylphosphine)palladium (0) in a solvent such as N,N-dimethylformamide with heating to provide compounds If formula (7) wherein $R^1$ is cyano.

Scheme 11

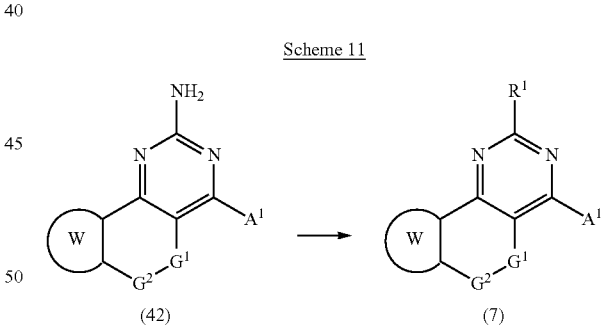

Compounds of formula (7), which are representative of compounds of the present invention wherein W, $G^1$, $G^2$ and $A^1$ are defined in formula (I), and wherein $R^1$ is limited to those compounds defined in formula (I) that are linked to the pyrimidine via nitrogen atom may be prepared as outlined in Scheme 11. 2-Aminopyrimidines of formula (42) can be prepared as described in the Schemes herein. 2-Aminopyrimidines of formula (42) can be reacted with reagents such as (alkyl-CO)$_2$O, $X^{2s}$-alkyl, alkyl-CO—$X^{2s}$, aryl-CO—$X^{2s}$, $X^{2s}$-alkylene($NR^7R^8$), $X^{2s}$—(C=O)-alkylene($NR^7R^8$) and $X^{2s}$-alkylene-heteroaryl, wherein $X^{2s}$ is a leaving group such as Cl, Br, methanesulfonate, p-toluenesulfonate or —O-succinimide optionally in the presence of a base such as Hunig's base or sodium hydride, pyridine or triethylamine, optionally in a solvent such as 2-methoxyethanol or N,N-dimethylformamide and optionally with heating to provide compounds of formula (7) wherein W, $G^1$, $G^2$ and $A^1$ are defined in formula (I) and $R^1$ is selected from —NH(acyl), —NH(alkyl), —N(alkyl)$_2$, —NH(C=O)aryl, —NH-alkylene(NR$^7$R$^8$), —NH(C=O)-alkylene(NR$^7$R$^8$), and —NH-alkylene-heteroaryl.

Scheme 12

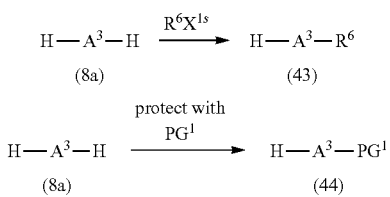

Compounds of formula (8a), wherein $A^3$ is defined in formula (I), are compounds wherein one of the H groups is a proton on an oxygen or sulfur atom and the other H group is a proton on a nitrogen atom of a primary or secondary amine. Compounds of formula (8a) can be directly reacted in Scheme 2 of the above in the presence of a strong base such as sodium hydride to provide compounds of formula (7). Alternatively, compounds of formula (8a) may be treated with an appropriate reagent such as $R^6$—$X^{1s}$, wherein $X^{1s}$ is a leaving group such as chlorine, bromine, iodine, mesylate or triflate, to provide compounds of formula (43) wherein the nitrogen atom of (43) is substituted with $R^6$. Alternatively, monoprotected diamines of formula (8a) may be treated with an appropriate aldehyde or ketone under condition of reductive amination to provide compounds of formula (43). Conditions commonly used for reductive amination include treatment of an amine (8a) with an aldehyde or ketone in the presence of sodium cyanoborohydride or sodium triacetoxyborohydride. Substituting compounds of formula (43) for compounds of formula (8) in the procedure outlined in Scheme 2 will provide compounds of formula (7) that are representative of the present invention. Compounds of formula (8a) may be treated with a reagent that will introduce a nitrogen protecting group (PG$^1$) on the nitrogen atom of (8a). Some typical examples of common nitrogen protecting groups include but are not limited to tert-butoxycarbonyl or benzyloxycarbonyl, which are introduced by treating compounds of formula (8a) with 1 equivalent of an appropriate reagent such as di-tert-butyl dicarbonate or benzyl chloroformate, respectively, to provide compounds of formula (44) wherein the protecting group (PG$^1$) is connected to the nitrogen atom. Substituting compounds of formula (44) for compounds of formula (8) in the procedure outlined in Scheme 2 will provide compounds of formula (7), wherein the $A^1$ group of formula (7) contains a protected nitrogen atom. This said protected nitrogen atom of compounds of formula (7) can be deprotected using conditions known to one skilled in the art such as catalytic hydrogenation (e.g. in the presence of palladium on carbon in a solvent such as ethanol under an atmosphere of hydrogen) and acidic conditions (e.g. treatment with aqueous hydrochloric acid or with trifluoroacetic acid) to provide compounds of formula (7) that are representative of the present invention.

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral, intravenous, subcutaneous, intramuscular, intraperitoneal, intra-arterial, or intradermal injection, or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals by oral administration, and by injection, including by intravenous, subcutaneous, intramuscular, intraperitoneal, intra-arterial, and intradermal injection. The pharmaceutical compositions of this invention can be administered to humans and other mammals topically (as by powders, lotions, ointments or drops applied to the skin), bucally, or by inhalation, as an oral or nasal spray. The pharmaceutical compositions of this invention can be administered to humans and other mammals intrarectally or intravaginally. The term "parenterally," as used herein, refers to modes of administration which include intravenous, intramuscular, intraperitoneal, intrasternal, subcutaneous and intraarticular.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents that delay absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, propionic, hydrobromic, glucuronic, methanesulfonic, ethanesulfonic, naphthalenesulfonic, lactic, fumaric, oxalic, and succinic acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound containing the carboxylic acid group with an alcohol such as methanol or ethanol in the presence of an acid such as hydrochloric acid.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl acid chloride. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

The compounds and processes of the invention will be better understood by reference to the following examples, which are intended as an illustration of and not a limitation upon the scope of the invention.

Unless otherwise described, reactions were carried out under ambient conditions (ranging 17-27° C.), under nitrogen. Unless otherwise described, column chromatography means flash chromatography carried out using silica gel, a technique well known to those of ordinary skill in the art of organic synthesis.

EXAMPLES

Example 1

4-octahydro-6H-pyrrolo[3,4-b]pyridin-6-yl-6,7-dihydro-5H-thieno[2',3':6,7]cyclohepta[1,2-d]pyrimidin-2-amine Example 1A methyl 4-oxo-5,6,7,8-tetrahydro-4H-cyclohepta[b]thiophene-5-carboxylate To a solution of 5,6,7,8-tetrahydro-cyclohepta[b]thiophen-4-one (0.84 g, 5 mmol), prepared by the method of M. P. Cagniant (Bull. Soc. Chim. France, 1956, 1152-1163), in dimethylcarbonate (6 mL) was added a 60% dispersion of sodium hydride in oil (0.4 g, 10 mmol) and a few drops of dry methanol. The reaction mixture was heated at reflux for 4 hours, then cooled, quenched with 2 N hydrochloric acid solution, and the desired product was extracted with ethyl acetate. The combined organic layers were dried over magnesium sulfate, concentrated and chromatographed on silica gel, eluting with 20% ethyl acetate:hexane to provide the title compound: $^1$H NMR (300 MHz, DMSO-$d_6$) δ 7.34 (d, J=5.42 Hz, 1H,), 7.28 (d, J=5.42 Hz, 1H), 4.04 (dd, J=10.8, 3.39 Hz, 1H), 3.66 (s, 3H), 3.80 (m, 4H), 3.14 (m, 2H); MS (DCI/NH$_3$) m/z 225 (M+H)$^+$, 242 (M+NH$_4$)$^+$.

Example 1B 2-amino-6,7-dihydro-5H-thieno[2',3':6,7]cyclohepta[1,2-d]pyrimidin-4-ol The product from Example 1A (1.2 g, 5.35 mmol) and guanidine nitrate (1.3 g, 10.7 mmol) were dissolved in N,N-dimethylformamide (5.5 mL), treated with potassium carbonate (1.48 g, 10.7 mmol) and stirred at 110° C. for 16 hours. The reaction mixture was cooled, diluted with water and neutralized to pH 6 with acetic acid. The solid was collected by filtration and purified by chromatography on silica gel, eluting with 10% methanol/dichloromethane/1% ammonium hydroxide to provide the title compound: $^1$H NMR (300 MHz, DMSO-$d_6$) δ 7.38 (d, J=5.43 Hz, 1H), 7.28 (d, J=5.43 Hz, 1H), 6.27 (br s, 2H), 2.89 (t, J=7.13 Hz, 2H), 2.43 (m, 2H), 1.95-2.05 (m, 2H); MS (DCI/NH$_3$) m/z 234 (M+H)$^+$.

Example 1C 2-amino-6,7-dihydro-5H-thieno[2',3':6,7]cyclohepta[1,2-d]pyrimidin-4-yl 4-methylbenzenesulfonate To a solution of product 1B (0.72 g, 3.1 mmol) in dichloromethane was added p-toluenesulfonyl chloride (1.18 g, 6.2 mmol) and triethylamine, followed by a catalytic amount of 4-(dimethylamino)pyridine. The reaction mixture was stirred at ambient temperature for 3 hours, then washed with water. The organic layers were combined, dried over magnesium sulfate and concentrated. The obtained residue was chromatographed on silica gel eluting with 20% ethyl acetate/hexane to provide the title compound: $^1$H NMR (300 MHz, DMSO-$d_6$) δ 8.02 (d, J=8.47 Hz, 2H), 7.49 (d, J=8.47 Hz, 2H), 7.44 (d, J=5.43 Hz, 1H), 7.35 (d, J=5.43 Hz, 1H), 6.77 (br s, 2H), 2.95 (t, J=6.78 Hz, 2H), 2.47 (m, 2H), 2.45 (s, 3H), 1.98 (m, 2H); MS (DCI/NH$_3$) m/z 399 (M+H)$^+$.

Example 1D 4-octahydro-6H-pyrrolo[3,4-b]pyridin-6-yl-6,7-dihydro-5H-thieno[2',3':6,7]cyclohepta[1,2-d]pyrimidin-2-amine dihydrochloride A solution of the product from Example 1C (0.6 g, 1.55 mmol), t-butyl octahydro-1H-pyrrolo[3,4-b]pyridine-1-carboxylate (CAS # 159877-36-8) (0.38 g, 1.7 mmol) and triethylamine (0.43 mL) in acetonitrile (1 mL) was heated to reflux for 16 hours. The mixture was concentrated and chromatographed on silica gel eluting with 5% methanol/dichloromethane mixture to yield the Boc-protected title compound. It was taken in methanol and treated with 4 N hydrochloric acid/dioxane at room temperature for 3 hours. The reaction mixture was concentrated and triturated with ether to yield the title product. $^1$H NMR (free base) (300 MHz, DMSO-$d_6$) δ 7.29 (d, J=5.43 Hz, 1H), 7.27 (d, J=5.43 Hz, 1H), 5.72 (s, 2H), 3.66-3.80 (m, 2H), 3.36 (m, 2H), 3.21 (m, 2H), 2.85 (m, 2H), 2.61-2.73 (m, 1H), 2.05-2.28 (m, 5H), 1.68 (m, 3H), 1.37 (m, 1H); MS (ESI+) m/z 342 (M+H)$^+$.

Example 2

4-[(3R)-3-aminopyrrolidin-1-yl]-6,7-dihydro-5H-thieno[2',3':6,7]cyclohepta[1,2-d]pyrimidin-2-amine A solution of the product from Example 1 (55 mg, 0.14 mmol), (R)-tert-butyl pyrrolidin-3-ylcarbamate (36 mg. 0.2 mmol) and 0.06 mL of Hunig's base in 1 mL of acetonitrile was heated at 160° C. in a microwave for 90 minutes. The reaction mixture was concentrated in vacuo and partitioned in water/dichloromethane. The organic layers were combined, dried over magnesium sulfate and concentrated. The obtained residue was chromatographed on silica gel, eluting with ethyl acetate to yield the Boc-protected title product. It was dissolved in methanol and treated with 4 N hydrochloric acid/dioxane at room temperature for 2 hours. The reaction mixture was concentrated and the residue was triturated with ether to yield the title product: $^1$H NMR (300 MHz, DMSO-$d_6$) δ 12.63 (s, 1H), 8.39 (br s, 2H), 7.67 (br s, 2H), 7.58 (d, J=5.43 Hz, 1H), 7.48 (d, J=5.43 Hz, 1H), 4.0 (m, 2H), 3.8 (m, 2H), 3.68 (m, 1H), 3.49 (m, 1H), 2.72-2.98 (m, 2H), 2.25-2.38 (m, 4H), 2.14 (m, 1H); MS (ESI+) m/z 302 (M+H)$^+$.

Example 3

4-[(3R)-3-(methylamino)pyrrolidin-1-yl]-6,7-dihydro-5H-thieno[2',3':6,7]cyclohepta[1,2-d]pyrimidin-2-amine A solution of the product from Example 1C (57 mg, 0.14 mmol), (R)-tert-butyl methylpyrrolidin-3-ylcarbamate (28 mg, 0.14 mmol) and 0.06 mL of Hunig's base in 1 mL of acetonitrile was treated as described in Example 2 to yield the title product: ¹H NMR (300 MHz, CDCl₃) δ 7.43 (d, J=5.09 Hz, 1H), 7.09 (d, J=5.09 Hz, 1H), 4.65 (br s, 2H), 3.77 (m, 2H), 3.65 (m, 1H), 3.43 (dd, J=11.02, 5.26 Hz, 1H), 3.32 (m, 1H), 2.82 (t, J=6.95 Hz, 2H), 2.5 (s, 3H), 2.42 (d, J=6.1 Hz, 2H), 2.28 (m, 2H), 2.13 (m, 1H), 1.82 (m, 1H); MS (ESI+) m/z 316 (M+H)⁺.

Example 4

4-octahydro-6H-pyrrolo[3,4-b]pyridin-6-yl-6,7-dihydro-5H-furo[2',3':6,7]cyclohepta[1,2-d]pyrimidin-2-amine Example 4A methyl 4-oxo-5,6,7,8-tetrahydro-4H-cyclohepta[b]furan-5-carboxylate 5,6,7,8-Tetrahydro-cyclohepta[b]furan-4-one (J. Chem. Soc., Perkin Trans. 1, 1980, 2081-2083) (0.1 g, 0.7 mmol) in dimethylcarbonate (2 mL) was treated with a 60% dispersion of sodium hydride (0.06 g, 0.15 mmol) as described in Example 1A to yield the title product. NMR in CDCl₃ indicates a 70:30 mixture of keto and enol forms: ¹H NMR (300 MHz, CDCl₃) δ 13.02 (s, 0.3H), 7.29 (d, J=2.03 Hz, 0.4H), 7.23 (d, J=2.03 Hz, 0.6H), 6.73 (d, J=2.03 Hz, 0.6H), 6.72 (d, J=2.03 Hz, 0.4H) 3.78 (s, 1.2H), 3.75 (s, 1.8H), 3.72 (dd, J=9.99, 3.9 Hz, 0.6H), 3.02 (m, 1.2H), 2.96 (t, J=6.6 Hz, 0.8H), 2.56 (t, 0.8H), 1.84-2.2 (m, 3.5H); MS (DCI/NH₃) m/z 209 (M+H)⁺.

Example 4B 2-amino-6,7-dihydro-5H-furo[2',3':6,7]cyclohepta[1,2-d]pyrimidin-4-ol A solution of the product from Example 4A (0.1 g, 0.5 mmol), guanidine nitrate (0.13 g, 1 mmol) and potassium phosphate (0.21 g, 1 mmol) in 2-methoxyethanol (2 mL) was heated in microwave at 160° C. for 1 hour. The reaction mixture was concentrated and the residue was chromatographed on silica gel, eluting with 10% methanol/dichloromethane/1% ammonium hydroxide to yield the title compound: ¹H NMR (300 MHz, DMSO-d₆) δ 10.67 (s, 1H), 7.53 (d, J=1.7 Hz, 1H), 6.79 (d, J=2.03 Hz, 1H), 6.2 (br s, 2H), 2.94 (t, J=6.61 Hz, 2H), 2.61 (m, 2H), 1.78 (m, 2H); MS (DCI) m/z 218 (M+H)⁺.

Example 4C 2-amino-6,7-dihydro-5H-furo[2',3':6,7]cyclohepta[1,2-d]pyrimidin-4-yl 4-methylbenzenesulfonate The product from Example 4B (0.06 g, 0.27 mmol) was treated with p-toluenesulfonyl chloride as described in Example 1C to yield the title product: ¹H NMR (300 MHz, CDCl₃) δ 7.94 (dt, J=8.48, 2.04 Hz, 2H), 7.35 (dd, J=8.48, 0.68 Hz, 2H), 7.31 (d, J=1.7 Hz, 1H), 6.93 (d, J=2.03 Hz, 1H), 4.78 (br s, 2H), 3.01 (t, J=6.61 Hz, 2H), 2.7 (m, 2H), 2.47 (s, 3H), 1.91 (m, 2H); MS (ESI+) m/z 372 (M+H)⁺.

Example 4D 4-octahydro-6H-pyrrolo[3,4-b]pyridin-6-yl-6,7-dihydro-5H-furo[2',3':6,7]cyclohepta[1,2-d]pyrimidin-2-amine dihydrochloride The product from Example 4C (56 mg, 0.15 mmol) was reacted with t-butyl octahydro-1H-pyrrolo[3,4-b]pyridine-1-carboxylate (CAS # 159877-36-8) (40 mg, 0.2 mmol) as described in Example 1D to yield the title compound: ¹H NMR (300 MHz, CD₃OD) δ 7.65 (d, J=2.03 Hz, 1H), 6.85 (d, J=2.03 Hz, 1H), 4.19 (dd, J=13.56, 5.09 Hz, 1H), 3.9 (m, 4H), 3.38 (m, 2H), 3.1 (m, 3H), 2.97 (m, 1H), 2.75 (m, 2H), 1.93 (m, 4H); MS (ESI+) m/z 326 (M+H)⁺.

Example 5

9-methyl-4-octahydro-6H-pyrrolo[3,4-b]pyridin-6-yl-6,7-dihydro-5H-furo[2',3':6,7]cyclohepta[1,2-d]pyrimidin-2-amine Example 5A ethyl (4E)-5-(5-methyl-2-furyl)pent-4-enoate To a suspension of triphenyl-(3-ethoxycarbonylpropyl)phosphonium bromide (2.27 g, 5 mmol) and 5-methylfurfural (0.55 g, 5 mmol) in 5 mL of dry tetrahydrofuran, a 1 M solution of sodium bis(trimethylsilyl)amide in tetrahydrofuran (5 mL) was added dropwise. The reaction mixture was stirred at room temperature for 2 hours and quenched with 2 N hydrochloric acid solution. The reaction mixture was extracted with ethyl acetate and the combined organic layers were dried over magnesium sulfate, concentrated and chromatographed eluting with 5% ethyl acetate/hexane to yield the title product: ¹H NMR (300 MHz, CDCl₃) δ 6.16 (d, J=3.05 Hz, 1H), 5.97 (dd, J=3.22, 0.85 Hz, 1H), 5.42 (dt, J=11.44, 7.11 Hz, 1H)), 4.14 (q, J=7.2 Hz, 2H), 2.76 (m, 2H), 2.47 (t, J=7.46 Hz, 2H), 2.31 (s, 3H), 1.25 (t, J=7.12 Hz, 3H); MS (DCI/NH₃)(M+H)⁺ m/z 209.

Example 5B ethyl 5-(5-methyl-2-furyl)pentanoate

A solution of compound from Example 5A (1.95 g, 9.4 mmol) in 100 mL of ethanol was hydrogenated for 2 hours in the presence of palladium on carbon (90 mg). The catalyst was filtered off and the filtrate was concentrated and chromatographed on silica gel eluting with 10% ethyl acetate/hexane to yield the title compound: ¹H NMR (300 MHz, CDCl₃) δ 5.64 (m, 2H), 4.12 (q, J=7.12 Hz, 2H), 2.58 (t, J=6.78 Hz, 2H), 2.31 (t, J=7.12 Hz, 2H), 2.24 (s, 3H), 1.66 (m, 4H), 1.25 (t, J=7.12 Hz, 3H); MS (DCI/NH₃) m/z 211 (M+H)⁺.

Example 5C 5-(5-methyl-2-furyl)pentanoic acid

A solution of compound from Example 5B (1.6 g, 7.6 mmol) in aqueous ethanol was treated with lithium hydroxide monohydrate (0.73 g, 17.6 mmol) for 2 hours at ambient temperature. The reaction mixture was concentrated and partitioned in water/ethyl acetate. The aqueous layer was acidified to pH 1 and extracted with ether to yield the title compound:
MS (DCI/NH₃) m/z 183 (M+H)⁺.

Example 5D 2-methyl-5,6,7,8-tetrahydro-4H-cyclohepta[b]furan-4-one

A solution of the product from Example 5C (1 g, 5.5 mmol) in dichloromethane (50 mL) was treated with oxalyl chloride (0.8 mL) in the presence of a catalytic amount of N,N-dimethylformamide. The reaction mixture was stirred at ambient temperature for 1 hour and concentrated in vacuo. The obtained acid chloride was dissolved in dichloromethane (15 mL) and added dropwise to dichloromethane (100 mL), and then cooled to 0° C. with the simultaneous addition of a solution of tin(II) chloride (1 mL) in dichloromethane (15 mL). Once the addition was completed, the reaction mixture was stirred at ambient temperature for 2 hours. The reaction mixture was partitioned in water/dichloromethane, the organic layer was separated, dried over magnesium sulfate and concentrated in vacuo. The obtained residue was chromatographed on silica gel, eluting with 10% ethyl acetate/hexane to yield the title compound. $^1$H NMR (300 MHz, CDCl$_3$) δ 6.28 (d, J=6.28 Hz, 1H), 2.96 (t, J=6.27 Hz, 2H), 2.7 (m, 2H), 2.23 (d, J=0.68 Hz, 3H), 1.86-2.04 (m, 4H); MS (DCI/NH$_3$) m/z 165 (M+H)$^+$.

Example 5E methyl 2-methyl-4-oxo-5,6,7,8-tetrahydro-4H-cyclohepta[b]furan-5-carboxylate A solution of compound 5D (0.65 g) in dimethylcarbonate (4 mL) was treated with 60% sodium hydride dispersion in oil (0.32 g, 8 mmol) as described in Example 1A to yield the title product. NMR in CDCl$_3$ indicates 40:60 mixture of keto and enol forms: $^1$H NMR (300 MHz, CDCl$_3$) δ 13.02 (s, 0.6H), 6.30 (br s, 1H), 3.78 (s, 2H), 3.75 (s, 1H), 3.68 (dd, J=9.16, 3.73 Hz, 0.35H), 2.96 (t, 0.7H), 2.89 (t, J=6.6 Hz, 1.3H), 2.56 (t, 1.3H), 2.25 (s, 2H), 2.26 (s, 1H), 1.84-2.2 (m, 2.7H); MS (DCI/NH$_3$) m/z 223 (M+H)$^+$.

Example 5F 2-amino-9-methyl-6,7-dihydro-5H-furo[2',3':6,7]cyclohepta[1,2-d]pyrimidin-4-ol The product from Example 5E (0.33 g, 1.5 mmol) in 2-methoxyethanol (5 mL) was treated with guanidine nitrate (0.36 g, 3 mmol) and potassium carbonate (0.4 g, 3 mmol) as described in Example 1B to yield the title product: $^1$H NMR (300 MHz, DMSO-d$_6$) δ 6.4 (s, 1H), 6.19 (br s, 2H), 2.89 (t, J=6.61 Hz, 2H), 2.58 (m, 2H), 2.23 (s, 3H), 1.75 (m, 2H); MS (DCI/NH$_3$) m/z 232 (M+H)$^+$.

Example 5G 2-amino-9-methyl-6,7-dihydro-5H-furo[2',3':6,7]cyclohepta[1,2-d]pyrimidin-4-yl 4-methylbenzenesulfonate The compound from Example 5F (0.165 g, 0.7 mmol) in dichloromethane was treated with p-toluenesulfonyl chloride (0.26 g, 1.4 mmol) as described in Example 1C to yield the title product: $^1$H NMR (300 MHz, CDCl$_3$) δ 7.94 (d, J=8.48 Hz, 2H), 7.35 (d, J=8.14 Hz, 2H), 6.51 (s, 1H), 4.76 (br s, 2H), 2.97 (t, J=6.44 Hz, 2H), 2.74 (m, 2H), 2.45 (s, 3H), 2.27 (s, 3H), 1.90 (m, 2H); MS (DCI/NH$_3$) m/z 386 (M+H)$^+$.

Example 5H 9-methyl-4-octahydro-6H-pyrrolo[3,4-b]pyridin-6-yl-6,7-dihydro-5H-furo[2',3':6,7]cyclohepta[1,2-d]pyrimidin-2-amine dihydrochloride The product from Example 5G (65 mg, 0.168 mmol) was treated with t-butyl octahydro-1H-pyrrolo[3,4-b]pyridine-1-carboxylate (CAS # 159877-36-8) (40 mg, 0.2 mmol) as described in Example 1D to yield the title compound: $^1$H NMR (300 MHz, DMSO-d$_6$) δ 12.17 (s, 1H), 9.53 (br s, 1H), 8.82 (br s, 1H), 6.78 (s, 1H), 4.02 (m, 1H), 3.65-3.88 (m, 4H), 3.23 (m, 2H), 3.0 (m, 2H), 2.88 (m, 2H), 2.15 (m, 2H), 2.31 (s, 3H), 2.01 (m, 2H), 1.75 (m, 3H); MS (ESI+) m/z 340 (M+H)$^+$.

Example 6

4-[(3R)-3-aminopyrrolidin-1-yl]-9-methyl-6,7-dihydro-5H-furo[2',3':6,7]cyclohepta[1,2-d]pyrimidin-2-amine The compound from Example 5G (65 mg, 0.168 mmol) was treated with (R)-tert-butyl pyrrolidin-3-ylcarbamate (36 mg, 0.2 mmol) as described in Example 2 to yield the title compound: $^1$H NMR (300 MHz, DMSO-d$_6$) δ 12.3 (s, 1H), 8.34 (s, 2H), 1.77 (br s, 2H), 6.84 (s, 1H), 3.91 (m, 3H), 3.73 (m, 2H), 3.01 (m, 2H), 2.71 (m, 2H), 2.31 (s, 3H), 2.22 (m, 1H), 2.03 (m, 3H); MS (ESI+) m/z 300 (M+H)$^+$.

Example 7

4-octahydro-6H-pyrrolo[3,4-b]pyridin-6-yl-6,7-dihydro-5H-furo[3',2':6,7]cyclohepta[1,2-d]pyrimidin-2-amine Example 7A ethyl (4E)-5-(3-furyl)pent-4-enoate 3-Furfural and triphenyl-(3-ethoxycarbonylpropyl)phosphonium bromide were processed as in 5A to yield the title compound: $^1$H NMR (300 MHz, CDCl$_3$) δ 7.46 (br s, 1H), 7.39 (t, J=1.36 Hz, 1H), 6.47 (d, J=2.03 Hz, 1H), 6.20 (d, J=11.53 Hz, 1H), 5.53 (dt, J=11.44, 6.99 Hz, 1H) 4.12 (q, J=7.12 Hz, 2H), 2.61 (t, J=6.78 Hz, 2H), 2.45 (td, J=7.63, 1.36 Hz, 2H), 1.25 (t, J=7.12 Hz, 3H); MS (DCI/NH$_3$) m/z 197 (M+H)$^+$.

Example 7B ethyl 5-(3-furyl)pentanoate

The product from Example 7A was processed as described in Example 5B to yield the title compound: $^1$H NMR (300 MHz, CDCl$_3$) δ 7.34 (m, 1H), 7.21 (m, 1H), 6.25 (d, J=1.02 Hz, 1H), 4.12 (q, J=7.12 Hz, 2H), 2.44 (t, J=7.46 Hz, 2H), 2.3 (t, J=7.12 Hz, 2H), 1.62 (m, 4H), 1.25 (t, J=7.12 Hz, 3H); MS (DCI/NH$_3$) m/z 199 (M+H)$^+$.

Example 7C 5-(3-furyl)pentanoic acid

The product from Example 7B was processed as described in 5C to yield the title compound: $^1$H NMR (300 MHz, CDCl$_3$) δ 7.34 (t, J=1.7 Hz, 1H), 7.21 (m, 1H), 6.25 (d, J=1.02 Hz, 1H), 2.44 (t, J=6.95 Hz, 2H), 2.38 (t, J=7.12 Hz, 2H), 1.55-1.75 (m, 4H); MS (DCI/NH$_3$) m/z 169 (M+H)$^+$.

Example 7D 4,5,6,7-tetrahydro-8H-cyclohepta[b]furan-8-one

The product from example 7C (0.81 g, 4.8 mmol) was processed as described for the Example 5D to yield the title compound: ¹H NMR (300 MHz, CDCl₃) δ 7.53 (d, J=1.7 Hz, 1H), 6.34 (d, J=1.7 Hz, 1H), 2.84 (t, J=6.10 Hz, 2H), 2.74 (m, 2H), 1.95 (m, 4H); MS (DCI/NH₃) m/z 151 (M+H)⁺.

Example 7E methyl 8-oxo-5,6,7,8-tetrahydro-4H-cyclohepta[b]furan-7-carboxylate

The product from the Example 7D (0.12 g) was processed as in Example 1A to yield the title compound: ¹H NMR (300 MHz, CDCl₃) 7.5 (d, J=1.7 Hz, 1H), 6.35 (d, J=1.7 Hz, 1H), 3.75 (s, 3H), 3.7 (dd, J=8.82, 3.73 Hz, 1H), 2.84 (m, 2H), 1.85-2.33 (m, 4H); (DCI/NH₃) m/z 209 (M+H)⁺.

Example 7F 2-amino-6,7-dihydro-5H-furo[3',2':6,7]cyclohepta[1,2-d]pyrimidin-4-ol The product from Example 7E (80 mg, 0.38 mmol) and guanidine nitrate were processed as described in Example 4B to yield the title compound: ¹H NMR (300 MHz, DMSO-d₆) δ 7.69 (d, J=1.7 Hz, 1H), 6.47 (d, J=2.03 Hz, 1H), 6.34 (br s, 2H) 2.74 (t, J=6.27 Hz, 2H), 2.58 (m, 2H), 1.75 (m, 2H); MS (ESI+) m/z 218 (M+H)⁺.

Example 7G 2-amino-6,7-dihydro-5H-furo[3',2':6,7]cyclohepta[1,2-d]pyrimidin-4-yl 4-methylbenzenesulfonate The product from Example 7F (30 mg, 0.138 mmol) was processed as described for Example 1C to yield the title product: ¹H NMR (300 MHz, DMSO-d₆) δ (7.98 (d, J=8.48 Hz, 2H), 7.78 (d, J=1.7 Hz, 1H), 7.48 (d, J=8.48 Hz, 2H), 6.79 (br s, 2H), 6.54 (d, J=2.03 Hz, 1H), 2.77 (t, J=6.27 Hz, 2H), 2.59 (m, 2H), 2.44 (s, 3H), 1.76 (m, 2H); MS (ESI+) m/z 372 (M+H)⁺.

Example 7H 4-octahydro-6H-pyrrolo[3,4-b]pyridin-6-yl-6,7-dihydro-5H-furo[3',2':6,7]cyclohepta[1,2-d]pyrimidin-2-amine The product from Example 7G was processed as described for Example 1D to yield the title compound: ¹H NMR (300 MHz, DMSO-d₆) δ 7.66 (d, J=1.69 Hz, 1H), 6.48 (d, J=1.69 Hz, 1H), 5.81 (br s, 2H), 3.71-3.80 (m, 2H), 3.41 (m, 2H), 3.21 (m, 2H), 2.85 (m, 2H), 2.61-2.73 (m, 5H), 2.35 (m, 1H), 1.63 (m, 3H), 1.31 (m, 1H); MS (ESI+) m/z 326 (M+H)⁺.

Example 8

8-methyl-4-(4-methylpiperazin-1-yl)-5,6,7,8-tetrahydropyrazolo[3',4':6,7]cyclohepta[1,2-d]pyrimidin-2-amine Example 8A methyl 1-methyl-4-oxo-1,4,5,6,7,8-hexahydrocyclohepta[c]pyrazole-5-carboxylate A solution of 1-methyl-5,6,7,8-tetrahydro-1H-cycloheptapyrazol-4-one (0.75 g, 4.6 mmol) in dimethylcarbonate (3 mL) is treated with 60% dispersion of sodium hydride in oil (0.4 g, 10 mmol) as described in Example 1A to yield the title compound: MS (DCI/NH₃) m/z 223 (M+H)⁺.

Example 8B 2-amino-8-methyl-5,6,7,8-tetrahydropyrazolo[3',4':6,7]cyclohepta[1,2-d]pyrimidin-4-ol The product from Example 8A (0.22 g, 1 mmol) and guanidine chloride (0.15 g, 1.5 mmol) were processed as described for Example 4B to yield the title compound: ¹H NMR (300 MHz, DMSO-d₆) δ 10.68 (s, 1H), 7.79 (s, 1H), 6.21 (br s, 2H), 3.72 (s, 3H), 2.89 (t, J=6.44 HZ, 2H), 2.59 (m, 2H), 1.81 (m, 2H); MS (DCI/NH₃) m/z 232 (M+H)⁺.

Example 8C 2-amino-8-methyl-5,6,7,8-tetrahydropyrazolo[3',4':6,7]cyclohepta[1,2-d]pyrimidin-4-yl 4-methylbenzenesulfonate The product from Example 8B (0.09 g, 0.4 mmol) was reacted with p-toluenesulfonyl chloride as described for Example 1C to yield the title compound: ¹H NMR (300 MHz, DMSO-d₆) δ 7.98 (d, J=8.14 Hz, 2H), 7.89 (s, 1H), 7.48 (d, J=8.14 Hz, 2H), 6.60 (br s, 2H), 3.73 (s, 3H), 2.82 (t, J=6.27 Hz, 2H), 2.58 (m, 2H), 2.43 (s, 3H), 1.82 (m, 2H); MS (ESI+) m/z 384 (M+H)⁺.

Example 8D 8-methyl-4-(4-methylpiperazin-1-yl)-5,6,7,8-tetrahydropyrazolo[3',4':6,7]cyclohepta[1,2-d]pyrimidin-2-amine A solution of the product from Example 8C (0.048 g, 0.12 mmol) and N-methylpiperazine (0.25 g, 0.25 mmol) in acetonitrile (1 mL) was heated in a microwave at 160° C. for 1 hour. The reaction mixture was partitioned in dichloromethane/water, the organic layer was separated, dried over magnesium sulfate and concentrated. The residue was chromatographed on silica gel, eluting with 5% methanol/dichloromethane/1% ammonium hydroxide to yield the title compound: ¹H NMR (300 MHz, DMSO-d₆) δ 7.84 (m, 1H), 5.96 (m, 2H), 3.76 (s, 3H), 3.07 (m, 4H), 2.93 (t, J=6.27 Hz, 2H), 2.59 (m, 2H), 2.43 (m, 4H), 2.22 (s, 3H), 1.90 (m, 2H); MS (ESI+) m/z 314 (M+H)⁺.

Example 9

4-[(3R)-3-aminopyrrolidin-1-yl]-8-methyl-5,6,7,8-tetrahydropyrazolo[3',4':6,7]cyclohepta[1,2-d]pyrimidin-2-amine The compound from Example 8C (65 mg, 0.168 mmol) was treated with (R)-tert-butyl pyrrolidin-3-ylcarbamate (36 mg, 0.2 mmol) as described in Example 2 to yield the title compound: ¹H NMR (300 MHz, DMSO-d₆) δ 7.80 (s, 1H), 5.5 (br s, 2H), 3.73 (m, 3H), 3.55 (m, 2H), 3.42 (m, 2H), 3.11

(m, 1 H), 2.89 (m, 2 H), 2.59 (m, 2 H), 1.95 (m, 3 H), 1.57 (m, 1 H); MS (ESI+) m/z 300 (M+H)+.

Example 10

8-tert-butyl-4-octahydro-6H-pyrrolo[3,4-b]pyridin-6-yl-5,6,7,8-tetrahydropyrazolo[3',4':6,7]cyclohepta[1,2-d]pyrimidin-2-amine Example 10A 1-tert-butyl-5,6,7,8-tetrahydrocyclohepta[c]pyrazol-4(1H)-one A solution of 1,3-cycloheptadione (2 g, mmol) was heated to reflux for 1 hour with dimethylforamide dimethylacetal (15 mL). The reaction mixture was concentrated and triturated with ether to yield 1.8 g of 2-dimethylaminomethylene-cycloheptane-1,3-dione. A solution of 2-dimethylaminomethylene-cycloheptane-1,3-dione (0.52 g, 2.9 mmol) and t-butylhydrazine hydrochloride (0.44 g, 3.5 mmol) in n-butanol (25 mL) and 0.3 mL of acetic acid was heated to reflux for 16 hours. The solvents were evaporated and the residue was chromatographed, eluting with 30% ethyl acetate/hexane to yield the title compound: $^1$H NMR (300 MHz, CDCl$_3$) δ 7.85 (s, 1 H), 3.17 (m, 2 H), 2.68 (m, 2 H), 1.98 (m, 2 H), 1.89 (m, 2H) 1.68 (s, 9 H); MS (DCI/NH$_3$) m/z 207 (M+H)+.

Example 10B methyl 1-tert-butyl-4-oxo-1,4,5,6,7,8-hexahydrocyclohepta[c]pyrazole-5-carboxylate A solution of product from Example 10A (0.3 g, 1.4 mmol) in dimethylcarbonate (4 mL) is treated with a 60% dispersion of sodium hydride in oil (0.11 g, 2.8 mmol) as described in Example 1A to yield the title compound. NMR in CDCl$_3$ indicates a 70:30 mixture of keto and enol forms: $^1$H NMR (300 MHz, CDCl$_3$) δ 7.87 (s, 0.4 H), 7.86 (s, 0.6 H), 3.79 (m, 0.6H), 3.76 (m, 1.2H), 3.70 (m, 1.2 H), 3.26 (m, 0.6 H), 3.08 (m, 1.1 H), 2.19 (m, 1 H), 2.00 (m, 2 H), 1.67 (s, 5.4 H), 1.66 (s, 3.6 H); MS (DCI/NH$_3$) m/z 265 (M+H)+.

Example 10C 2-amino-8-tert-butyl-5,6,7,8-tetrahydropyrazolo[3',4':6,7]cyclohepta[1,2-d]pyrimidin-4-ol The product from the Example 10B (0.28 g, 1.1 mmol) and guanidine nitrate (0.26 g, 2.2 mmol) were processed as described for Example 1B to yield the title compound: $^1$H NMR (300 MHz, DMSO-d$_6$) δ 7.83 (s, 1 H), 6.14 (br s, 2 H), 3.11 (t, J=6.10 Hz, 2 H), 2.57 (m, 2 H), 1.85 (m, 2 H), 1.59 (s, 9 H); MS (DCI/NH$_3$) m/z 274 (M+H)+.

Example 10D 2-amino-8-tert-butyl-5,6,7,8-tetrahydropyrazolo[3',4':6,7]cyclohepta[1,2-d]pyrimidin-4-yl 4-methylbenzenesulfonate The product from the Example 10C (0.05 g, 0.18 mmol) and p-toluenesulfonyl chloride (0.078 g, 0.36 mmol) were treated as described for Example 1C to yield the title compound: $^1$H NMR (300 MHz, CDCl$_3$) δ 8.11 (s, 1 H), 7.93 (d, J=8.48 Hz, 2 H), 7.39 (d, J=8.48 Hz, 2 H), 6.6 (br s, 2 H), 3.15 (t, J=6.44 Hz, 2 H), 2.76 (m, 2 H), 2.46 (s, 3H), 2.01 (m, 2 H), 1.70 (m, 9 H); MS (ESI+) m/z 429 (M+H)+.

Example 10E 8-tert-butyl-4-octahydro-6H-pyrrolo[3,4-b]pyridin-6-yl-5,6,7,8-tetrahydropyrazolo[3',4':6,7]cyclohepta[1,2-d]pyrimidin-2-amine The product from the Example 10D (0.038 g, 0.8 mmol) and t-butyl octahydro-1H-pyrrolo[3,4-b]pyridine-1-carboxylate (CAS # 159877-36-8) (0.38 g, 1.7 mmol) were processed as described for the Example 1D to yield the title compound. $^1$H NMR (300 MHz, CDCl$_3$) δ 7.87 (s, 1 H), 4.6 (br s, 2 H), 3.75-3.93 (m, 2 H), 3.33-3.50 (m, 3 H), 3.09-3.22 (m, 1 H), 2.98-3.08 (m, 1 H), 2.75-2.92 (m, 1 H), 2.55-2.73 (m, 2 H), 2.36-2.50 (m, 1H), 2.22-2.33 (m, 1 H), 2.09-2.22 (m, 2 H), 1.73-1.85 (m, 2 H), 1.64-1.69 (m, 9 H).

Example 11

4-[(3R)-3-(methylamino)pyrrolidin-1-yl]-8-phenyl-5,6,7,8-tetrahydropyrazolo[3',4':6,7]cyclohepta[1,2-d]pyrimidin-2-amine Example 11A 1-phenyl-5,6,7,8-tetrahydrocyclohepta[c]pyrazol-4(1H)-one A solution of 2-dimethylaminomethylene-cycloheptane-1,3-dione (0.18 g, 1 mmol), obtained as described for Example 10A, phenyl hydrazine (0.11 g, 1 mmol) in n-butanol (10 mL), and 0.1 mL of acetic acid was heated to reflux for 16 hours. The solvents were evaporated and the residue was chromatographed, eluting with 30% ethyl acetate/hexane to yield the title compound: $^1$H NMR (300 MHz, CDCl$_3$) δ 8.10 (s, 1 H), 7.33-7.68 (m, 5 H), 2.92 (m, 2 H), 2.78 (m, 2 H), 1.97 (m, 4 H); MS (DCI/NH$_3$) m/z 227 (M+H)+.

Example 11B methyl 4-oxo-1-phenyl-1,4,5,6,7,8-hexahydrocyclohepta[c]pyrazole-5-carboxylate The product from the Example 11A (0.36 g, 1.6 mmol) in dimethylcarbonate (4 mL) was treated with a 60% dispersion of sodium hydride in oil (0.13 g, 1.6 mmol) as described for Example 1A to yield the title compound: $^1$H NMR (300 MHz, CDCl$_3$) δ 13.13 (m, 1 H), 8.13 (m, 1 H), 7.48 (m, 5 H), 3.83 (m, 3 H), 2.90 (m, 2 H), 2.64 (m, 2 H), 1.93 (m, 2 H); MS (DCI/NH$_3$) (M+H)+ m/z 285.

Example 11C 2-amino-8-phenyl-5,6,7,8-tetrahydropyrazolo[3',4':6,7]cyclohepta[1,2-d]pyrimidin-4-ol The product from the Example 11B (0.32 g, 1.1 mmol) was treated with guanidine nitrate (0.27 g, 2.2 mmol) as described for Example 1B to yield the title compound: $^1$H NMR (300

MHz, DMSO-d$_6$) δ 7.83 (s, 1 H), 7.38 (m, 5 H), 6.44 (br s, 2 H), 3.25 (t, J=6.10 Hz, 2H), 2.62 (m, 2 H), 1.93 (m, 2 H); MS (DCI/NH$_3$) m/z 294 (M+H)$^+$.

Example 11D

4-[(4-methylphenyl)sulfonyl]-8-phenyl-5,6,7,8-tetrahydropyrazolo[3',4':6,7]cyclohepta[1,2-d]pyrimidin-2-amine The product from the Example 11C (0.11 g, 0.4 mmol) was treated with p-toluenesulfonyl chloride as described for Example 1C to yield the title compound: $^1$H NMR (300 MHz, CDCl$_3$) δ 8.35 (s, 1 H), 7.96 (d, J=8.48 Hz, 2 H), 7.48 (m, 5 H), 7.37 (d, J=8.48 Hz, 2 H), 4.79 (s, 2 H), 2.93 (t, J=6.27 Hz, 2 H), 2.85 (m, 2 H), 2.47 (s, 3 H), 1.94 (m, 2 H);
MS (ESI+) m/z 448 (M+H)$^+$.

Example 11E tert-butyl (3R)-1-(2-amino-8-phenyl-5,6,7,8-tetrahydropyrazolo[3',4':6,7]cyclohepta[1,2-d]pyrimidin-4-yl)pyrrolidin-3-yl(methyl)carbamate A solution of the product from the Example 11D (20 mg, 0.45 mmol) and (R)-methyl-pyrrolidin-3-yl-carbamic acid tert-butyl ester (12 mg, 0.6 mmol) was heated in a microwave at 160° C. for 1.5 hours. The reaction mixture was concentrated and chromatographed on silica gel, eluting with 5% methanol/dichloromethane to yield the title compound: $^1$H NMR (300 MHz, CDCl$_3$) δ 8.26 (s, 1 H), 7.47 (m, 5 H), 4.63 (m, 2 H), 3.58 (m, 3 H), 2.90 (m, 4 H), 2.70 (m, 2 H), 2.06 (m, 4 H), 1.48 (m, 9 H); MS (ESI+) m/z 476 (M+H)$^+$.

Example 11F

4-[(3R)-3-(methylamino)pyrrolidin-1-yl]-8-phenyl-5,6,7,8-tetrahydropyrazolo[3',4':6,7]cyclohepta[1,2-d]pyrimidin-2-amine trifluoroacetate The product from Example 11E (5 mg) was dissolved in dichloromethane (0.5 ml) and treated with trifluoroacetic acid (0.5 mL) for 1 hour at ambient temperature. The reaction mixture was concentrated and triturated with ether to yield the title compound: $^1$H NMR (300 MHz, DMSO-d$_6$) δ 8.66 (s, 1 H), 8.16 (s, 1 H), 7.59 (m, 5 H), 3.84 (m, 2 H), 2.91 (t, J=6.78 Hz, 2 H), 2.67 (m, 4H), 2.45 (s, 3H), 2.27 (m, 2 H), 2.14 (m, 3 H); MS (ESI+) m/z 376 (M+H)$^+$.

Example 12

9-bromo-4-octahydro-6H-pyrrolo[3,4-b]pyridin-6-yl-6,7-dihydro-5H-thieno[2',3':6,7]cyclohepta[1,2-d]pyrimidin-2-amine Example 12A 2-bromo-5,6,7,8-tetrahydro-4H-cyclohepta[b]thiophen-4-one To a solution of 5,6,7,8-tetrahydro-cyclohepta[b]thiophen-4-one (0.5 g, 3 mmol) in 50% aqueous acetic acid (5 mL), cooled to −5° C., was added dropwise a solution of bromine (0.15 mL) in acetic acid (3 mL). The reaction mixture was stirred at −5° C. for 1 hour and quenched into aqueous sodium acetate. The resulting precipitate was filtered off to give the title compound: $^1$H NMR (300 MHz, CDCl$_3$) δ ppm 7.36 (s, 1 H), 3.01 (m, 2 H), 2.71 (m, 2H), 1.94 (m, 4 H); MS (DCI/NH$_3$) m/z 245 (M+H)$^+$.

Example 12B methyl 2-bromo-4-oxo-5,6,7,8-tetrahydro-4H-cyclohepta[b]thiophene-5-carboxylate The product from the Example 12A (0.36 g, 1.6 mmol) in dimethylcarbonate (4 mL) was treated with a 60% dispersion of sodium hydride in oil (0.12 g, 3.2 mmol) as described for Example 1A to yield the title compound. NMR in CDCl3 indicated a mixture of keto and enol forms of the product: $^1$H NMR (300 MHz, CDCl$_3$) δ 7.38 (s, 0.4H), 7.25 (s, 0.6H), 3.81 (s, 1 H), 3.77 (s, 2 H), 3.77 (m, 1 H), 3.00 (m, 2 H), 2.88 (t, J=6.78 Hz, 1 H), 2.43 (m, 2 H), 2.15 (m, 3 H), 1.93 (m, 1 H); MS (DCI/NH$_3$) m/z 303 (M+H)$^+$.

Example 12C 2-amino-9-bromo-6,7-dihydro-5H-thieno[2',3':6,7]cyclohepta[1,2-d]pyrimidin-4-ol The product from the Example 12B (0.21 g, 0.7 mmol) and guanidine nitrate (0.16 g, 0.14 mmol) were processed as described in the Example 1B. The reaction mixture was concentrated and chromatographed on silica gel eluting with 10% ethanol/dichloromethane to yield the title compound: $^1$H NMR (300 MHz, DMSO-d$_6$) δ 7.44 (s, 1 H), 6.29 (s, 2 H), 2.87 (t, J=6.78 Hz, 3 H), 2.46 (m, 2 H), 1.98 (m, 2 H); MS (ESI+) m/z 314 (M+H)$^+$.

Example 12D 9-bromo-4-[(4-methylphenyl)sulfonyl]-6,7-dihydro-5H-thieno[2',3':6,7]cyclohepta[1,2-d]pyrimidin-2-amine The product from the Example 12C (0.05 g, 0.16 mmol) was treated with p-toluenesulfonyl chloride (90.06 g, 0.32 mmol) as described for the Example 1C to yield the title compound: $^1$H NMR (300 MHz, CDCl$_3$) δ 7.96 (d, J=8.14 Hz, 2 H), 7.47 (s, 1 H), 7.37 (d, J=8.14 Hz, 2 H), 4.81 (m, 2 H), 2.89 (t, J=6.95 Hz, 2 H), 2.66 (m, 2 H), 2.47 (s, 3 H), 2.12 (m, 2 H); MS (ESI+) m/z 468 (M+H)$^+$.

Example 12E 9-bromo-4-octahydro-6H-pyrrolo[3,4-b]pyridin-6-yl-6,7-dihydro-5H-thieno[2',3':6,7]cyclohepta[1,2-d]pyrimidin-2-amine The product from the Example 12D (0.07 g, 0.15 mmol) and t-butyl octahydro-1H-pyrrolo[3,4-b]pyridine-1-carboxylate (CAS # 159877-36-8) (0.043 g, 0.19 mmol) were processed as described for the Example 1D to yield the title compound: $^1$H NMR (300 MHz, CD$_3$OD) δ 7.30 (m, 1 H), 4.19 (m, 1 H), 3.97 (m, 3 H), 3.42 (m, 2 H), 3.06 (m, 2 H), 2.78 (m, 3 H), 2.50 (m, 2 H), 2.32 (m, 1 H), 1.93 (m, 4 H); MS (ESI+) m/z 422 (M+H)$^+$.

Example 13

4-octahydro-6H-pyrrolo[3,4-b]pyridin-6-yl-9-phenyl-6,7-dihydro-5H-thieno[2',3':6,7]cyclohepta[1,2-d]pyrimidin-2-amine

Example 13A

2-phenyl-5,6,7,8-tetrahydro-4H-cyclohepta[b]thiophen-4-one

A solution of product from the Example 12A (0.36 g, 1.5 mmol), phenylboronic acid (0.23 g, 18 mmol), sodium carbonate (0.38 g, 3.6 mmol) and dichlorobis(triphenylphosphine)palladium (II) (32 mg) in i-propanol:water (3:1) (15 mL) was heated to reflux for 3 hours. The reaction mixture was concentrated, partitioned in dilute saturated aqueous sodium bicarbonate solution/dichloromethane. The organic layers were combined, dried over magnesium sulfate and evaporated. The obtained residue was chromatographed eluting with 30% ethyl acetate/hexane to yield the title compound: $^1$H NMR (300 MHz, CDCl$_3$) δ 7.63 (m, 1 H), 7.56 (m, 2 H), 7.38 (m, 2 H), 7.30 (m, 1 H), 3.12 (m, 2 H), 2.77 (m, 2 H), 1.97 (m, 4 H); MS (DCI/NH$_3$) m/z 243 (M+H)$^+$.

Example 13B methyl 4-oxo-2-phenyl-5,6,7,8-tetrahydro-4H-cyclohepta[b]thiophene-5-carboxylate The product from the Example 13A (0.27 g, 1.1 mmol) in dimethylcarbonate (2 mL) was treated with a 60% dispersion of sodium hydride in oil (0.1 g, 2.2 mmol) as described for Example 1A to yield the title compound. NMR in CDCl$_3$ indicates it is a mixture of keto and enol forms of the product: $^1$H NMR (300 MHz, CDCl$_3$) δ7.61 (s, 1H), 7.55 (m, 2 H), 7.38 (m, 2 H), 7.3 (m, 1 H), 3.77-3.81 (m, 2 H), 2.43-2.53 (m, 1 H), 2.15-2.31 (m, 2 H), 1.92-2.14 (m, 3 H); MS (DCI/NH$_3$) m/z 301 (M+H)$^+$.

Example 13C

2-amino-9-phenyl-6,7-dihydro-5H-thieno[2',3':6,7]cyclohepta[1,2-d]pyrimidin-4-ol The product from the Example 13B (0.25 g, 0.8 mmol) and guanidine nitrate (0.19 g, 0.16 mmol) were processed as described in the Example 1B to yield the title compound: $^1$H NMR (300 MHz, DMSO-d$_6$) δ 7.74 (s, 1 H), 7.57 (m, 2 H), 7.43 (t, J=7.46 Hz, 2 H), 7.30 (m, 1 H), 6.33 (br s, 2 H), 2.94 (t, J=6.95 Hz, 2 H), 2.47 (m, 2H), 2.04 (m, 2H); MS (DCI/NH$_3$) m/z 310 (M+H)$^+$.

Example 13D

4-[(4-methylphenyl)sulfonyl]-9-phenyl-6,7-dihydro-5H-thieno[2',3':6,7]cyclohepta[1,2-d]pyrimidin-2-amine The product from the Example 13C (0.14 g, 0.45 mmol) was treated with p-toluenesulfonyl chloride (0.2 g, 1 mmol) as described in Example 1C to yield the title compound: $^1$H NMR (300 MHz, CDCl$_3$) δ7.98 (d, J=7.12 Hz, 2 H), 7.62 (d, J=8.82 Hz, 2 H), 7.38 (m, 5 H), 7.2 (s, 1H), 3.01 (t, J=6.44 Hz, 2 H), 2.69 (m, 2 H), 2.49 (s, 3 H), 2.19 (m, 2 H); MS (ESI+) m/z 464 (M+H)$^+$.

Example 13E

4-octahydro-6H-pyrrolo[3,4-b]pyridin-6-yl-9-phenyl-6,7-dihydro-5H-thieno[2',3':6,7]cyclohepta[1,2-d]pyrimidin-2-amine dihydrochloride The product from the Example 13D (0.06 g, 0.13 mmol) and t-butyl octahydro-1H-pyrrolo[3,4-b]pyridine-1-carboxylate (CAS # 159877-36-8) (0.034 g, 0.15 mmol) were processed as described for the Example 1D to yield the title compound: $^1$H NMR (free base) (DMSO-d$_6$) δ 7.63 (m, 3 H), 7.43 (m, 2 H), 7.28 (m, 1 H), 5.80 (m, 2 H), 3.76 (m, 2 H), 3.39 (m, 1 H), 3.22 (m, 3 H), 2.87 (m, 2 H), 2.68 (m, 1 H), 2.21 (m, 5 H), 1.64 (m, 3 H), 1.37 (m, 1H); MS (ESI+) m/z 418 (M+H)$^+$.

Example 14

4-(4-methylpiperazin-1-yl)-6,7-dihydro-5H-pyrido[3',2':6,7]cyclohepta[1,2-d]pyrimidin-2-amine

Example 14A

5,6,7,8-tetrahydro-9H-cyclohepta[b]pyridin-9-one

To a solution of oxalyl chloride (1 mL) in dichloromethane, cooled to −78° C. was added dropwise a solution of dimethyl sulfoxide (1.5 mL) in dichloromethane. The mixture was stirred for 10 minutes and a solution of 6,7,8,9-tetrahydro-5H-cyclohepta[b]pyridin-9-ol (Chem. Pharm. Bull. 43, 3, 1995), (1.42 g, 8.7 mmol) in dichloromethane was added to it. After 30 minutes, triethylamine (6 mL) was added to the reaction mixture and it was stirred at ambient temperature for 1 hour and partitioned in dichloromethane/water. The organic layer was dried over magnesium sulfate and concentrated. The residue was chromatographed on silica gel, eluting with ethyl acetate to yield the title compound: $^1$H NMR (300 MHz, CDCl$_3$) δ 8.64 (dd, J=4.58, 1.53 Hz, 1 H), 7.58 (dd, J=7.63, 1.53 Hz, 1 H), 7.33 (dd, J=7.80, 4.75 Hz, 1 H), 2.92 (m, 2 H), 2.80 (m, 2 H), 1.90 (s, 4 H); MS (DCI/NH$_3$) m/z 162 (M+H)$^+$.

Example 14B methyl 9-oxo-6,7,8,9-tetrahydro-5H-cyclohepta[b]pyridine-8-carboxylate

The product from the Example 14A (0.5 g, 3.1 mmol) in dimethylcarbonate (4 mL) was treated with a 60% dispersion of sodium hydride in oil (0.24 g) as described for Example 1A to yield the title compound: $^1$H NMR (300 MHz, CDCl$_3$) δ 8.65 (dd, J=4.75, 1.70 Hz, 1H), 7.56 (dd, J=7.46, 1.70 Hz, 1 H), 7.28 (d, J=4.75 Hz, 1 H), 3.86 (s, 3 H), 2.63 (t, J=6.78 Hz, 2 H), 2.12 (m, 4 H).

Example 14C

2-amino-6,7-dihydro-5H-pyrido[3',2':6,7]cyclohepta[1,2-d]pyrimidin-4-ol

A solution of the product from the Example 14B (0.22 g, 1 mmol), guanidine chloride (0.19 g, 2 mmol), and potassium carbonate (0.28 g, 2 mmol) in 1,2-dimethoxyethane (2 mL) was heated in microwave at 155° C. for 1 hour. The reaction mixture was cooled, diluted with water and acidified with acetic acid to pH 6. The resulting precipitate was filtered off and washed with water to yield the title compound: $^1$H NMR (300 MHz, CDCl$_3$) δ 8.65 (dd, J=4.75, 1.70 Hz, 1 H), 7.56

(dd, J=7.46, 1.70 Hz, 1 H), 7.28 (d, J=4.75 Hz, 1 H), 3.86 (s, 3H), 2.63 (t, J=6.78 Hz, 2 H), 2.12 (m, 4 H).

Example 14D

4-[(4-methylphenyl)sulfonyl]-6,7-dihydro-5H-pyrido[3',2':6,7]cyclohepta[1,2-d]pyrimidin-2-amine The product from the Example 14C (0.11 g, 0.5 mmol) was treated with p-toluenesulfonyl chloride (0.2 g, 1 mmol) as described for the Example 1C to yield the title compound: $^1$H NMR (300 MHz, DMSO-d$_6$) δ 8.57 (dd, J=4.75, 1.70 Hz, 1 H), 8.04 (d, J=8.14 Hz, 2 H), 7.75 (dd, J=7.63, 1.53 Hz, 1 H), 7.51 (d, J=8.14 Hz, 2 H), 7.42 (dd, J=7.46, 4.75 Hz, 1 H), 6.97 (br s, 2 H), 2.45 (s, 3 H), 2.43 (m, 2 H), 2.21 (t, J=6.78 Hz, 2 H), 2.00 (m, 2 H); MS (DCI/NH$_3$) m/z 367 (M+H)$^+$.

Example 14E 4-(4-methylpiperazin-1-yl)-6,7-dihydro-5H-pyrido[3',2':6,7]cyclohepta[1,2-d]pyrimidin-2-amine The product from the Example 14D (0.05 g, 0.13 mmol) and N-methylpiperazine (0.2 g, 0.2 mmol) in acetonitrile (1 mL) were processed as described for Example 8D to yield the title compound: $^1$H NMR (300 MHz, DMSO-d$_6$) δ 8.55 (dd, J=4.75, 1.70 Hz, 1 H), 7.70 (dd, J=7.46, 1.70 Hz, 1 H), 7.35 (dd, J=7.80, 4.75 Hz, 1 H), 6.16 (s, 2 H), 3.28 (m, 4 H), 2.55 (t, J=6.10 Hz, 2 H), 2.45 (m, 4 H), 2.20 (m, 4 H); MS (DCI/NH$_3$) m/z 312 (M+H)$^+$.

Example 15

4-[(3R)-3-aminopyrrolidin-1-yl]-6,7-dihydro-5H-pyrido[3',2':6,7]cyclohepta[1,2-d]pyrimidin-2-amine The compound from the Example 14D (0.05 g, 0.13 mmol) and (R)-tert-butyl pyrrolidin-3-ylcarbamate (0.036 mg, 0.2 mmol) were processed as described in Example 2 to yield the title compound: $^1$H NMR (300 MHz, DMSO-d$_6$) δ 8.54 (dd, J=4.75, 1.70 Hz, 1 H), 7.68 (d, J=6.10 Hz, 1 H), 7.33 (dd, J=7.63, 4.58 Hz, 1 H), 5.84 (s, 2 H), 3.68 (dd, J=10.34, 6.27 Hz, 1 H), 3.50 (m, 2 H), 3.23 (m, 1 H), 2.55 (t, J=6.10 Hz, 2 H), 2.24 (m, 2 H), 2.09 (m, 2 H), 1.96 (m, 1 H), 1.64 (m, 1 H); MS (ESI+) m/z 297 (M+H)$^+$.

Example 16

10-methyl-4-(4-methylpiperazin-1-yl)-6,7-dihydro-5H-isoxazolo[5',4':6,7]cyclohepta[1,2-d]pyrimidin-2-amine

Example 16A 3-methyl-3a,5,6,7,8,8a-hexahydro-4H-cyclohepta[d]isoxazol-4-one

To a solution of 80% technical grade 2-cycloheptenone (3.48 mL, 25 mmol) and triethylamine (1 mL) in toluene were added phenylisocyanate (5.95 g, 50 mmol) and nitroethane (2.24 g, 30 mmol) in four portions over 1 hour. The reaction mixture was stirred at ambient temperature for 4 hours, the precipitate was filtered off and the filtrate was concentrated. The obtained residue was chromatographed, eluting with 20% ethyl acetate/hexane to yield the title compound: $^1$H NMR (300 MHz, CDCl$_3$) δ 4.81 (m, 1 H), 4.06 (d, J=11.87 Hz, 1 H), 2.47 (m, 2 H), 2.02 (m, 3 H), 1.93 (m, 2 H), 1.81 (m, 2 H), 1.67 (m, 2 H); MS (DCI/NH$_3$) m/z 168 (M+H)$^+$.

Example 16B 3-methyl-5,6,7,8-tetrahydro-4H-cyclohepta[d]isoxazol-4-one

A solution of the product from the Example 16A (2.2 g, 13.2 mmol) and 2,3-dichloro-5,6-dicyano-p-benzoquinone (2 g, 8.8 mmol) in toluene was heated to reflux for 3 hours. The hot reaction mixture was filtered off and the filtrate was concentrated and chromatographed, eluting with 30% ethyl acetate/hexane to yield the title compound: $^1$H NMR (300 MHz, CDCl$_3$) δ 3.10 (t, 2 H), 2.75 (m, 2 H), 2.43 (s, 3 H), 2.00 (m, 4 H); MS (DCI/NH$_3$) m/z 166 (M+H)$^+$.

Example 16C methyl 3-methyl-4-oxo-5,6,7,8-tetrahydro-4H-cyclohepta[d]isoxazole-5-carboxylate The product from Example 16B (0.55 g, 3.3 mmol) in dimethylcarbonate (4 mL) was treated with a 60% dispersion of sodium hydride in oil (0.26 g, 6.6 mmol) as described for Example 1A to yield the title compound as an oil. NMR in CDCl$_3$ indicates a mixture of keto and enol forms (85:15): $^1$H NMR (300 MHz, CDCl$_3$)(keto form) δ 3.77 (s, 3 H), 3.71 (m, 1H), 3.10 (m, 2 H), 2.43 (s, 3 H), 2.10 (m, 4 H); MS (DCI/NH$_3$) m/z 224 (M+H)$^+$.

Example 16D 2-amino-10-methyl-6,7-dihydro-5H-isoxazolo[5',4':6,7]cyclohepta[1,2-d]pyrimidin-4-ol The product from the Example 16C (0.22 g, 1 mmol) and guanidine hydrochloride (0.19 g, 2 mmol) were processed as described for Example 14C to yield the title compound: $^1$H NMR (300 MHz, DMSO-d$_6$) δ 6.30 (m, 2 H), 3.03 (t, J=6.95 Hz, 2 H), 2.57 (m, 2 H), 2.48 (s, 3H), 1.81 (m, 2 H); MS (DCI/NH$_3$) m/z 233 (M+H)$^+$.

Example 16E 2-amino-10-methyl-6,7-dihydro-5H-isoxazolo[5',4':6,7]cyclohepta[1,2-d]pyrimidin-4-yl methanesulfonate To the solution of product from Example 16D (0.11 g, 0.5 mmol) in dichloromethane was added methanesulfonyl chloride (0.11 g, 1 mmol) followed by the addition of triethylamine (0.3 ml). The reaction mixture was stirred at room temperature for 16 hours, then diluted with methylene chloride and washed with a solution of sodium bicarbonate, and water. The organic layer was dried and concentrated in vacuo. The obtained residue was chromatographed eluting with 20% ethyl acetate/hexane to yield the title compound: $^1$H NMR (300 MHz, DMSO-d$_6$) δ 6.96 (br s, 2 H), 3.72 (s, 3 H), 3.12 (t, J=6.61 Hz, 2 H), 2.66 (m, 2 H), 2.53 (s, 3 H), 1.89 (m, 2 H); MS (ESI+) m/z 311 (M+H)$^+$.

Example 16F 10-methyl-4-(4-methylpiperazin-1-yl)-6,7-dihydro-5H-isoxazolo[5',4':6,7]cyclohepta[1,2-d]pyrimidin-2-amine A solution of the product from the Example 16C (0.05 g, 0.16 mmol) in acetonitrile (4 mL) was heated at reflux with 1-methylpipearzine (0.1 mL) for 16 hours. The reaction mixture was concentrated and the obtained residue was chromatographed on silica gel, eluting with 10% ethanol/dichloromethane to yield the title compound: $^1$H NMR (300 MHz, DMSO-d$_6$) δ 6.13 (br s, 2 H), 3.28 (s, 3 H), 3.08 (m, 6 H), 2.58 (m, 2 H), 2.43 (m, 4 H), 2.23 (s, 3 H), 1.90 (m, 2 H); MS (ESI+) m/z 315 (M+H)$^+$.

Example 17

4-[(3R)-3-aminopyrrolidin-1-yl]-10-methyl-6,7-dihydro-5H-isoxazolo[5',4':6,7]cyclohepta[1,2-d]pyrimidin-2-amine Example 17A N-(4-hydroxy-10-methyl-6,7-dihydro-5H-isoxazolo[5',4':6,7]cyclohepta[1,2-d]pyrimidin-2-yl)-2,2-dimethylpropanamide The product from the Example 16D (0.12 g, mmol) in pyridine (5 mL) was treated with trimethylacetylchloride (0.2 mL) at ambient temeperature for 2 hours. The reaction mixture was concentrated and the residue was partitioned in dilute aqueous sodium bicarbonate/dichloromethane. The organic layer was concentrated in vacuo and triturated with ethyl acetate to yield the title compound: $^1$H NMR (300 MHz, DMSO-d$_6$) δ ppm 3.09 (t, J=6.95 Hz, 2 H), 2.66 (m, 2 H), 2.55 (s, 3 H), 1.85 (dd, J=5.76, 4.41 Hz, 2 H), 1.28 (s, 9 H); MS (ESI+) m/z 317 (M+H)$^+$.

Example 17B

N-(4-chloro-10-methyl-6,7-dihydro-5H-isoxazolo[5',4':6,7]cyclohepta[1,2-d]pyrimidin-2-yl)-2,2-dimethylpropanamide The product from the Example 17A was treated with phosphorous(V) oxychloride (5 mL) at reflux for 2 hours. The reaction mixture was concentrated to yield the title compound: $^1$H NMR (300 MHz, DMSO-d$_6$) δ ppm 10.17 (s, 1 H), 3.18 (t, J=6.95 Hz, 2 H), 2.96 (m, 2H), 2.62 (s, 3 H), 1.95 (m, 2 H), 1.25 (s, 9 H); MS (ESI+) m/z 335 (M+H)$^+$.

Example 17C

4-[(3R)-3-aminopyrrolidin-1-yl]-10-methyl-6,7-dihydro-5H-isoxazolo[5',4':6,7]cyclohepta[1,2-d]pyrimidin-2-amine The compound from the Example 17B (0.06 g, 0.18 mmol) in dichloromethane (2 mL) was heated to reflux with (R)-tert-butyl pyrrolidin-3-ylcarbamate (0.036 mg, 0.2 mmol) and triethylamine (0.02 mL) for 16 hours. The reaction mixture was concentrated and the residue was chromatographed eluting with 5% ethanol/dichloromethane to yield the Boc-protected title compound. It was dissolved in dioxane (5 mL) and treated with a 15% solution of potassium hydroxide for 4 hours at reflux. The reaction mixture was concentrated and partitioned in water/dichloromethane. The organic layer was concentrated and redissolved in dichloromethane and treated with trifluoroacetic acid (1 mL) at room temperature for 2 hours. The reaction mixture was concentrated, partitioned in 1 N sodium hydroxide/dichloromethane. The organic layer was dried over magnesium sulfate and concentrated. The residue was triturated with hexane/ethyl acetate to yield the title compound: $^1$H NMR (300 MHz, DMSO-d$_6$) δ ppm 5.79 (br s, 2 H), 3.57 (m, 2 H), 3.44 (m, 3H), 3.11 (dd, J=10.34, 5.26 Hz, 1 H), 2.99 (t, J=6.95 Hz, 3 H), 2.46 (s, 3 H), 2.00 (m, 2 H), 1.91 (m, 1 H), 1.71 (m, 1 H), 1.58 (m, 1 H); MS (ESI+) m/z 301 (M+H)$^+$.

Example 18

4-[(4aR,7aR)-octahydro-6H-pyrrolo[3,4-b]pyridin-6-yl]-6,7-dihydro-5H-thieno[2',3':6,7]cyclohepta[1,2-d]pyrimidin-2-amine A solution of the product from Example 1C (0.125 g, 0.32 mmol), (4aR,7aR)— t-butyl octahydro-1H-pyrrolo[3,4-b]pyridine-1-carboxylate (CAS # 159877-36-8) (0.08 g, 0.35 mmol) and triethylamine (0.1 mL) in acetonitrile (1 mL) was heated to reflux for 16 hours. The mixture was concentrated and chromatographed on silica gel eluting with 5% methanol/dichloromethane to yield the Boc-protected title compound. It was taken in methanol and treated with 4 N hydrochloric acid/dioxane at room temperature for 3 hours. The reaction mixture was concentrated and triturated with ether to yield the title product: $^1$H NMR (free base) (300 MHz, DMSO-d$_6$) δ 7.29 (d, J=5.43 Hz, 1H), 7.27 (d, J=5.43 Hz, 1H), 5.72 (s, 2H), 3.66-3.80 (m, 2H), 3.36 (m, 2H), 3.21 (m, 2H), 2.85 (m, 2H), 2.61-2.73 (m, 1H), 2.05-2.28 (m, 5H), 1.68 (m, 3H), 1.37 (m, 1H); MS (ESI$^+$) m/z 342 (M+H)$^+$.

Example 19

4-(4-methylpiperazin-1-yl)-5,6-dihydrofuro[2,3-h]quinazolin-2-amine

Example 19A 4-(methylthio)-5,6-dihydrofuro[2,3-h]quinazolin-2-amine

A solution of 6,7-dihydro-4(5H)-benzofuranone (0.10 g, 0.73 mmol), carbon disulfide (0.048 mL, 0.80 mmol), and iodomethane (0.10 mL, 1.6 mmol) in tetrahydrofuran (1.8 mL) was treated with a 60% dispersion of sodium hydride in mineral oil (0.070 g, 1.8 mmol), stirred over night at ambient temperature and partitioned between saturated ammonium chloride and ethyl acetate. The organic layer was washed with brine, dried (magnesium sulfate), filtered and concentrated. The residue was treated with guanidine nitrate (0.36 g, 2.9 mmol), treated with 1.46 mL (2.2 mol) of 1.5 M sodium ethoxide in ethanol, heated to 80° C. overnight, cooled, diluted with water and extracted with dichloromethane (3×). The combined dichloromethane layers were dried (magnesium sulfate), filtered, concentrated and chromatographed using ethyl acetate in dichloromethane to provide the title compound: $^1$H NMR (300 MHz, CDCl$_3$) δ 2.52 (s, 3H), 2.88-3.02 (m, 4H), 5.07 (br s, 2H), 6.87 (d, J=1.7 Hz, 1H), 7.37 (d, J=2.0 Hz, 1H); MS (DCI/NH$_3$) m/z 234 (M+H)$^+$.

Example 19B 4-(4-methylpiperazin-1-yl)-5,6-dihydrofuro [2,3-h]quinazolin-2-amine The product from Example 19A (26 mg, 0.11 mmol) was dissolved in dichloromethane (2 mL), treated with 70% 3-chloroperoxybenzoic acid (83 mg, 0.34 mmol), stirred at room temperature for 1 hour, treated with sodium sulfite solution, treated with sodium bicarbonate solution, and extracted with dichloromethane (2×). The combined dichloromethane layers were dried (magnesium sulfate), filtered, concentrated and chromatographed using ethyl acetate in dichloromethane to provide the sulfone intermediate, 4-(methylsulfonyl)-5,6-dihydrofuro[2,3-h]quinazolin-2-amine. This sulfone intermediate was treated with excess 1-methylpiperazine (110 mg, 1.1 mmol) in 2-methoxyethanol (1 mL) heated to 110° C. over night. The reaction mixture was cooled and partitioned between 1 M sodium hydroxide and dichloromethane. The layers were separated and the aqueous layer was extracted with dichloromethane (2×). The combined dichloromethane layers were dried (magnesium sulfate), filtered, concentrated and chromatographed (2, 3.5 and 5% (9:1 methanol:concentrated ammonium hydroxide) in dichloromethane) to provide the title compound: $^1$H NMR (300 MHz, CDCl$_3$) δ 2.36 (s, 3H), 2.55 (t, J=4.7 Hz, 4H), 2.81 (m, 2H), 2.93 (m, 2H), 3.33 (t, J=4.7 Hz, 4H), 4.80 (br s, 2H), 7.13 (d, J=5.1 Hz, 1H), 7.53 (d, J=5.1 Hz, 1H); MS (DCI/NH$_3$) m/z 286 (M+H)$^+$.

Example 20

6-(4-methylpiperazin-1-yl)-2-phenyl-4,5-dihydro-2H-[1,2,3]triazolo[4,5-h]quinazolin-8-amine The procedure from Example 19, substituting 2-phenyl-2,5,6,7-tetrahydro-4-h-1,2,3-benzotriazol-4-one for 6,7-dihydro-4(5H)-benzofuranone, provided the title compound: $^1$H NMR (300 MHz, CDCl$_3$) δ 2.54 (s, 3H), 2.75-2.94 (m, 6H), 3.00-3.09 (m, 2H), 3.51-3.62 (m, 4H), 4.96 (br s, 2H), 7.31-7.38 (m, 1H), 7.43-7.52 (m, 2H), 8.14-8.20 (m, 2H).

Example 21

4-(4-methylpiperazin-1-yl)-5,6-dihydrothieno[2,3-h]quinazolin-2-amine

The procedure from Example 19, substituting 4-keto-4,5,6,7-tetrahydrothianaphthene for 6,7-dihydro-4(5H)-benzofuranone, provided the title compound: $^1$H NMR (300 MHz, CDCl$_3$) δ 2.42 (s, 3H), 2.60-2.67 (m, 4H), 2.86-2.89 (m, 4H), 3.39-3.45 (m, 4H), 4.94 (br s, 2H), 6.87-6.91 (m, 1H), 7.36 (d, J=2.0 Hz, 1H); MS (DCI/NH$_3$) m/z 302 (M+H)$^+$.

Example 22

7-methyl-4-(4-methylpiperazin-1-yl)-6,7-dihydro-5H-pyrrolo[2,3-h]quinazolin-2-amine The title product was prepared using the procedure outlined in the Example 19A and 19B substituting 1-methyl-6,7-dihydro-1H-indol-4(5H)-one (CAS# 51471-08-0) for 6,7-dihydro-4(5H)-benzofuranone: MS (DCI/NH$_3$) m/z 299 (M+H)$^+$.

Example 23

4-(4-methylpiperazin-1-yl)-5,6-dihydropyrido[3,4-h]quinazolin-2-amine

The title product was prepared using the procedure outlined in the Example 19A and 19B substituting 7,8-dihydroisoquinolin-5(6H)-one (CAS# 21917-86-2) for 6,7-dihydro-4(5H)-benzofuranone: $^1$H NMR (300 MHz, CD$_3$OD) δ 2.34 (s, 3 H) 2.56-2.62 (m, 4 H) 2.70-2.78 (m, 2 H) 2.81-2.88 (m, 2 H) 3.36-3.42 (m, 4 H) 7.93 (d, J=5.09 Hz, 1 H) 8.45 (s, 1 H) 8.49 (d, J=5.09 Hz, 1 H); MS (DCI/NH$_3$) m/z 302 (M+H)$^+$.

Determination of Biological Activity

There are many methods available to show the effectiveness of compounds as histamine H$_4$ receptor ligands. Histamine H$_4$ receptors from mammalian species have been cloned. Methods to clone, express, and assess the potency and functional activity of such cloned genes are well known to those skilled in the art of molecular biology. Examples of methods of cloning and expressing histamine H$_4$ receptors, and of assessing the potency and functional activity are described in Nguyen, et al. Molecular Pharmacology (2001) vol. 59 pp. 427-433; Zhu, et al. Molecular Pharmacology (2001) vol. 59 pp. 434-441; Coge, et al., Biochemical and Biophysical Research Communications (2001) vol. 284, pp. 301-309; Liu, et al. Molecular Pharmacology (2001) vol. 59 pp. 420-426; Liu, et al. Journal of Pharmacology and Experimental Therapeutics (2001) v. 299, pp. 121-130; and Thurmond, et al. Journal of Pharmacology and Experimental Therapeutics (2004) v. 309, pp. 404-413. In the present case, to determine the potency and effectiveness of representative compounds of this invention as histamine-H$_4$ receptor ligands (H$_4$ receptor ligands), the following tests were conducted according to previously described methods (see Esbenshade, et al., Biochemical Pharmacology (2004), vol. 68, pp. 933-945, and in Krueger, et al., Journal of Pharmacology and Experimental Therapeutics (2005) v. 314, pp. 271-281): histamine H$_4$ receptors were cloned and stably expressed in HEK-293 (human embryonic kidney) cells coexpressing a Gαqi5. Before testing, cells are loaded with a Ca$^{+2}$ sensitive fluorescent dye, in this case Fluo-4. In the case of partial agonist or agonist ligands, addition of compound to the cells leads to the increase in intracellular Ca$^{+2}$ which is detected by FLIPR (Fluorescence Imaging Plate Reader; Molecular Devices, Sunnyvale, Calif.) technology. In a similar manner, compounds that are antagonists or inverse agonists, block the increase in fluorescence induced by the full histamine H$_4$ agonist histamine, and partial agonists reduce the amount of fluorescence induced by the full histamine H$_4$ agonist histamine. The fluorescence intensities measured before addition of the test compound are subtracted from the fluorescence intensities at later time points. Peak response values determined at each concentration of ligand are expressed as a percentage of the response obtained with the full agonist histamine. Concentration versus response data are analyzed to obtain compound potency as K$_b$ values for antagonists and inverse agonists and as EC$_{50}$ values for partial agonists.

TABLE 1

In vitro histamine H$_4$ potency of compounds in FLIPR

| Example # | Potency (nM) |
| --- | --- |
| 1 | 17 |
| 2 | 6.6 |
| 3 | 3.7 |
| 4 | 14 |
| 5 | 34 |
| 6 | 252 |
| 7 | 20 |
| 8 | 107 |
| 9 | 105 |
| 10 | 187 |
| 11 | 46 |
| 12 | 35 |
| 13 | 700 |
| 14 | 37 |
| 15 | 35 |

TABLE 1-continued

In vitro histamine $H_4$ potency of compounds in FLIPR

| Example # | Potency (nM) |
|---|---|
| 16 | 2350 |
| 17 | 1860 |
| 18 | 6 |

Generally, representative compounds of the invention demonstrated potencies in the above FLIPR assay from about 4 nM to about 10,000 nM. Preferred compounds of the invention have potencies at histamine-$H_4$ receptors from about 4 nM to about 200 nM. More preferred compounds of the invention have potencies at histamine $H_4$ receptors from about 4 nM to about 40 nM.

The potency of compounds of the invention in displacing $^3$H-histamine in competition binding assays is assessed by methods described in Esbenshade, et al., Biochemical Pharmacology (2004), vol. 68, pp. 933-945. In this assay, membranes were prepared from HEK-293 cells transiently transfected with the pCINeo expression vector harboring the histamine $H_4$ receptor by homogenization of the cells on ice in TE buffer (50 mM Tris-HCl buffer, pH 7.4, containing 5 mM EDTA), 1 mM benzamidine, 2 μg/ml aprotinin, 1 μg/ml leupeptin, and 1 μg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer. Competition radioligand binding assays were performed with increasing concentrations of test compound in the presence of [$^3$H]-histamine incubated at 25° C. for 1 hour in a total volume of 0.5 ml of 50 mM Tris, 5 mM EDTA, pH 7.4. All binding reactions were terminated by filtration under vacuum onto polyethylenimine (0.3%) presoaked Unifilters (PerkinElmer Life Sciences) or Whatman GF/B filters (Whatman, Clifton, N.J.) followed by three brief washes with 4 ml of ice-cold TE buffer. Bound radiolabel was determined by liquid scintillation counting. For all of the radioligand competition binding assays, $IC_{50}$ values and Hill slopes were determined by Hill transformation of the data and $K_i$ values were determined by the Cheng-Prusoff equation. The following table of representative histamine $H_4$ receptor ligands is provided, along with potency values:

| Compound Name (Example number) | Potency (nM) |
|---|---|
| 1 | 6.0 |
| 2 | 10 |
| 3 | 8.8 |
| 4 | 12 |
| 7 | 165 |
| 9 | 426 |
| 10 | 44 |
| 18 | 1.8 |
| 20 | 1300 |
| 21 | 80 |

Generally, representative compounds of the invention demonstrate potencies from about 4 nM to about 10,000 nM. Preferred compounds of the invention have potencies at histamine-$H_4$ receptors from about 4 nM to about 200 nM. More preferred compounds of the invention have potencies at histamine $H_4$ receptors from about 4 nM to about 40 nM.

In addition to the utility of in vitro methods for characterizing the potency of compounds at the $H_4$ receptor, there are animal disease models available which demonstrate the utility of compounds. There are a number of methods to test the activity of compounds in different pain models that are well known to those skilled in the art. A description of the formalin test in rats, as neuropathic pain models in rats, and general descriptions of methods of testing and descriptions of pain models are found in the book 'Drug Discovery and Evaluation, $2^{nd}$ edition' (H. Gerhard Vogel, editor; Springer-Verlag, New York, 2002; pp. 702-706).

The usefulness of histamine $H_4$ receptor ligands in treating pain has been demonstrated (Coruzzi, et al., *Eur. J. Pharmacol.* 2007, 563, 240-244). This invention discloses the novel utility of the compounds of the invention to treat pain, including multiple types of pain, including inflammatory pain, non-inflammatory pain, and neuropathic pain. Neuropathic pain is distinct from other types of pain (e.g. inflammatory pain) in that it can develop in response to previous or ongoing tissue injury, nerve injury, or diabetes, but it persists long after signs of the original injury or damage have disappeared. Neuropathic pain is not currently well treated, and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell, Expert Opinion on Emerging Drugs (2005) vol. 10(1), pp. 95-108; Vinik and Mehrabyan, Medical Clinics of North America (2004), vol. 88(4), pp. 947-999; Dray, Urban, and Dickenson, Trends in Pharmacological Sciences (1994) vol. 15(6) pp. 190-7; Dworkin, Clinical Journal of Pain (2002) vol. 18(6) pp. 343-9. There do exist a number of animal models of neuropathic pain that can be used to assess the ability of the compounds of the invention to treat neuropathic pain, as discussed herein.

Animal models of neuropathic pain are predictive of efficacy of treatment of neuropathic pain in humans. These models are used to assess the efficacy of compounds of the invention in treating neuropathic pain. Examples of models well known to those skilled in the art include the Chung model (Kim and Chung, Pain (1992) vol. 50 pp. 355-363) and the Bennett model (Bennett and Xie, Pain (1988) vol. 30 pp. 87-107).

Determination of Analgesic Effect Against Neuropathic Pain

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation was evaluated using testing with von Frey filaments. As described previously by S. R. Chaplan, et al. ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annu. Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of ≤4 g of pressure. By comparison, for the control paw without allodynia (in this case the right side paw), the typical withdrawal pressure is around 15 g. Representative compounds of the invention, administered intraperitoneally 30 minutes before testing, are able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses is determined by comparing response in the surgery-affected paw versus the response in the control paw. This is expressed as the MPE (maximum percent effect), or 100 times the withdrawal threshold of the allodynic (left side) divided by the withdrawal threshold of the control (right side).

Determination of Analgesic Effect Against Inflammatory Pain

To assess the effectiveness of representative compounds of the invention against acute model inflammatory pain, animals were tested in an acute model of carrageenan-induced thermal hyperalgesia (see for example, Honore, et al. Behavioural Brain Research 167 (2006) 355-364; Porreca, et al Journal of Pharmacology and Experimental Therapeutics (2006) vol. 318 pp. 195-205). Carrageenan was injected into the test paw of the animal, and after 90 minutes, the test drug was administered by intraperitoneal dosing; the effect on thermal hyperalgesia was assessed in a hotbox assay which done 30 minutes after the intraperitoneal dosing of the test drug, and the MPE (maximal percent effect) reported by comparison to the control paw (not injected with carrageenan), according to 100 times the withdrawal latency of the carrageenan injected paw (in seconds) divided by the withdrawal latency of the control (not injected with carrageenan) paw.

Compounds of the invention are histamine $H_4$ receptor ligands that modulate function of the histamine $H_4$ receptor by altering the activity of the receptor. These compounds may be antagonists that block the action of receptor activation induced by histamine $H_4$ receptor agonists such as histamine; they may be histamine $H_4$ receptor inverse agonists that inhibit the basal activity of the receptor and block the action of receptor activation induced by histamine $H_4$ receptor agonists such as histamine, and they may be partial agonists that partially block the action of receptor activation induced by histamine $H_4$ receptor agonists such as histamine and prevent full activation of histamine $H_4$ receptors.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

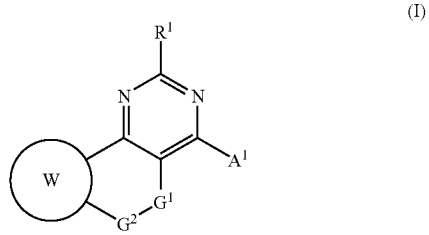

or a pharmaceutically acceptable, salt, ester, or amide thereof, wherein:

$R^1$ is hydrogen, alkoxy, alkoxycarbonyl, alkyl, —(C=O)—NH-alkylene($NR^7R^8$), —(C=O)—($NR^7R^8$), carboxy, cyano, cyanoalkyl, cycloalkyl, fluoroalkyl, fluorocycloalkyl, hydroxyalkyl, $NH_2$, —NH(acyl), —NH(alkyl), —N(alkyl)$_2$, —NH(C=O)aryl, —NH-alkylene($NR^7R^8$), —NH(C=O)-alkylene($NR^7R^8$), —$NR^7$(C=O)$NR^7R^8$, —NH-alkylene-heteroaryl, —NHOH, —NHOCH$_3$, —O-alkylene($NR^7R^8$), or piperazine;

$G^1$ is oxygen, sulfur, S(O), S(O)$_2$, $NR^7$ or alkylene;

$G^2$ is oxygen, sulfur, S(O), S(O)$_2$, $NR^7$, or alkylene;

wherein each carbon of the alkylene and alkylene groups of $G^1$ and $G^2$ may be optionally substituted with one or more groups selected from the group consisting of acyl, acyloxy, alkenyl, alkoxy, alkoxyalkoxy, alkoxyalkyl, alkoxycarbonyl, alkyl, alkylsulfonyl, alkylthio, alkynyl, amido, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, fluorine, formyl, haloalkoxy, haloalkyl, halogen, hydroxy, hydroxyalkyl, mercapto, nitro, and oxo;

provided that only one of $G^1$ or $G^2$ can be oxygen, sulfur, S(O), S(O)$_2$ or $NR^7$;

W represents an optionally substituted heteroaryl ring selected from the group consisting of

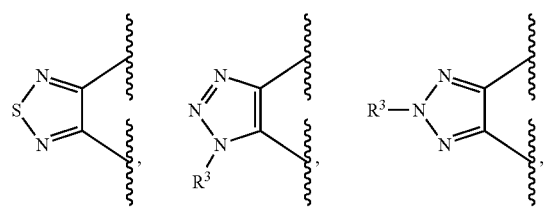

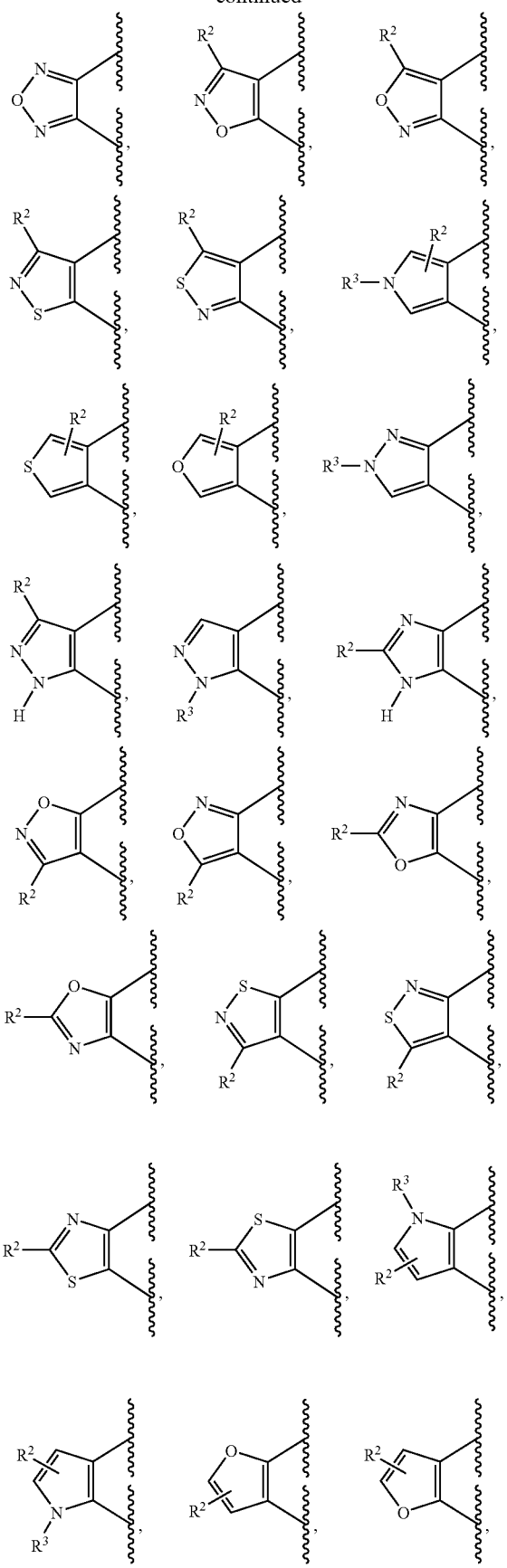

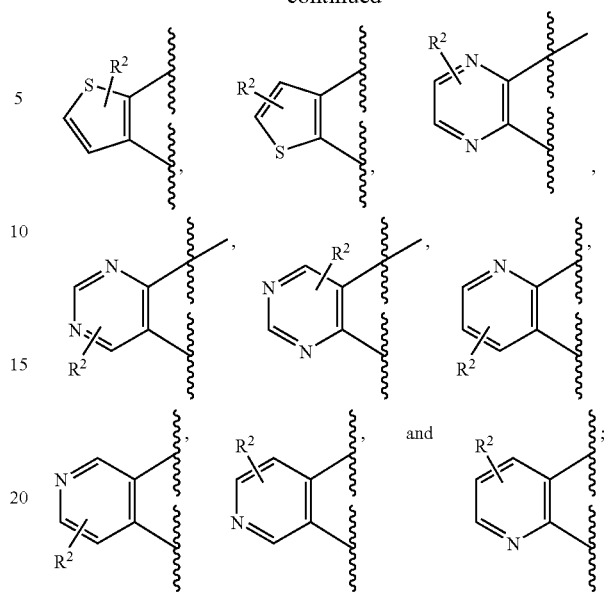

R[2] is hydrogen, acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, aryl, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, formyl, haloalkoxy, haloalkyl, halogen, hydroxy, hydroxyalkyl, mercapto, nitro, CONR[7]R[8], NR[7]COalkyl, —NR[7](C=O)Oalkyl, or O-aryl;

R[3] is hydrogen, alkyl, aryl, cyanoalkyl, cycloalkoxyalkyl, cycloalkyl, cycloalkylalkyl, fluoroalkyl, fluorocycloalkyl, or fluorocycloalkylalky;

R[4] is hydrogen, alkoxyalkyl, alkyl, cyanoalkyl, cycloalkoxyalkyl, cycloalkyl, cycloalkylalkyl, fluoroalkyl, fluorocycloalkyl, fluorocycloalkylalkyl, or hydroxyalkyl;

R[5] is alkoxyalkyl, fluoroalkyl, fluorocycloalkyl, fluorocycloalkylalkyl, or hydroxyalkyl;

R[6] is hydrogen, acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluoroalkyl, fluorocycloalkyl, fluorocycloalkylalkyl, formyl, heteroaryl, heterocycle, hydroxy, or hydroxyalkyl;

R[7] and R[8] are each independently acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluorocycloalkyl, fluorocycloalkylalkyl, heteroaryl, heterocycle, hydrogen, formyl, hydroxy, or hydroxyalkyl;

A[1] is a group of structure A[2]; wherein A[2] is:

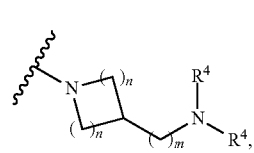

B

| 73 -continued | | 74 -continued | |
|---|---|---|---|
| 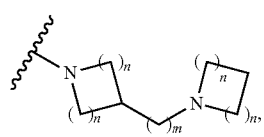 | C | 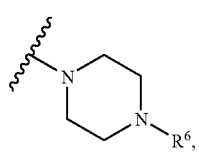 | K |
| 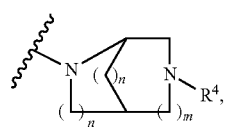 | D | 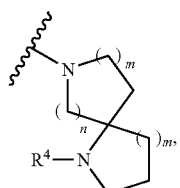 | L |
| 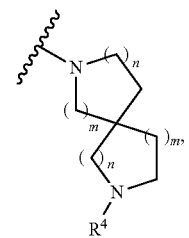 | E | 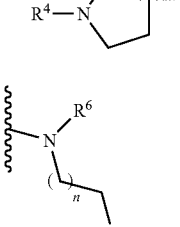 | M |
| 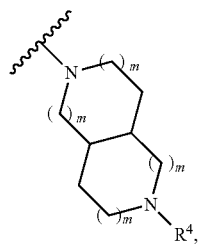 | F |  | N |
| 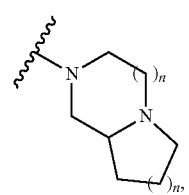 | G | 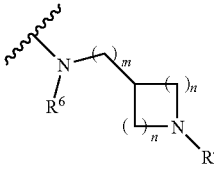 | O |
| 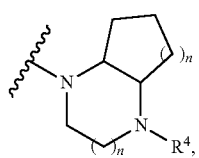 | H |  | P |
| 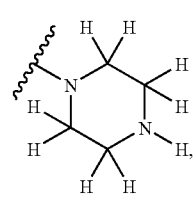 | I |  | Q |
| 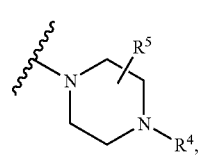 | J |  | R |

75
-continued
S 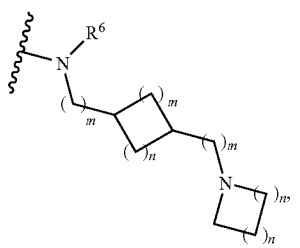
T 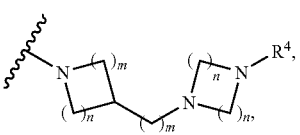
U 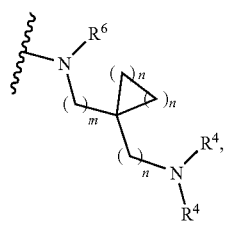
V 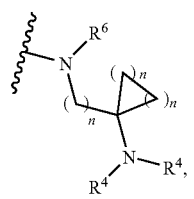
W 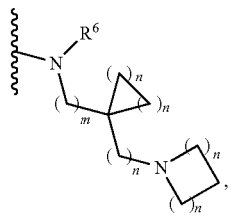
X 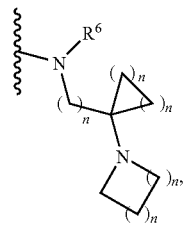
Y1 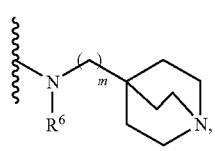
Y2 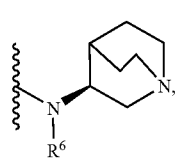
76
-continued
Y3 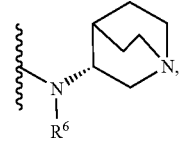
Y4 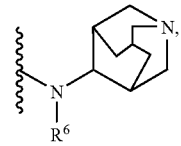
Y5 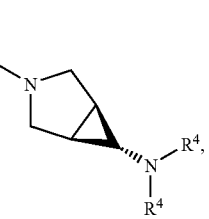
Y6 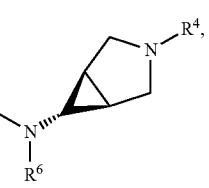
Y9 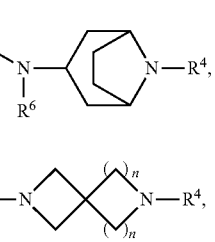
Y10 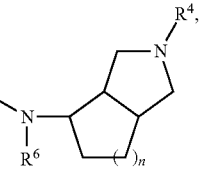
Y11 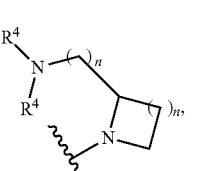
Y12 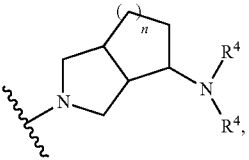
Y13 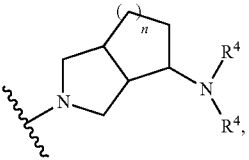

-continued

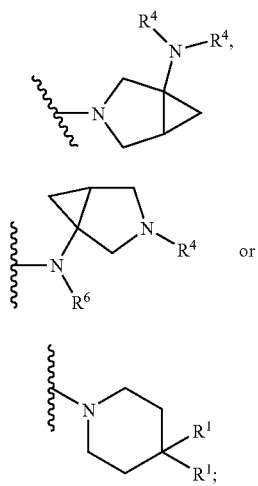

wherein n is 1, 2, or 3; and m is 0, 1, or 2;

wherein each carbon atom of groups A¹ may be optionally substituted with one or more groups selected from acyl, acyloxy, alkenyl, alkoxy, alkoxyalkoxy, alkoxyalkyl, alkoxycarbonyl, alkyl, alkylsulfonyl, alkylthio, alkynyl, amido, carboxy, cyano, cyanoalkyl, cycloalkoxyalkyl, cycloalkyl, cycloalkylalkyl, fluorine, fluoroalkoxy, fluoroalkyl, fluorocycloalkyl, fluorocycloalkylalkyl, formyl, haloalkoxy, haloalkyl, hydroxy, hydroxyalkyl, mercapto, and nitro;

provided that when G¹ is CH₂ or CH₂CH₂ and G² is CH₂ and R¹ is NH₂, NHalkyl, or N(alkyl)₂, then A¹ is not a group of structure K.

2. The compound according to claim 1 wherein

G¹ is —CH₂—;

G² is —CH₂—CH₂—; and

R¹ is NH₂, —NH(acyl), —NH(alkyl), —N(alkyl)₂, —NH(C=O)aryl, —NH-alkylene(NR⁷R⁸), —NH(C=O)-alkylene(NR⁷R⁸), —NR⁷(C=O)NR⁷R⁸, —NH-alkylene-heteroaryl, —NHOH, or —NHOCH₃.

3. The compound according to claim 2, wherein A² is

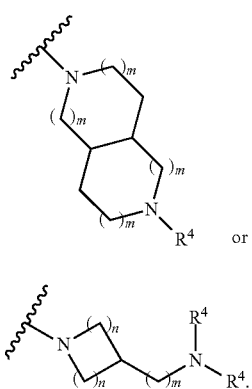

4. The compound according to claim 3, wherein W is selected from

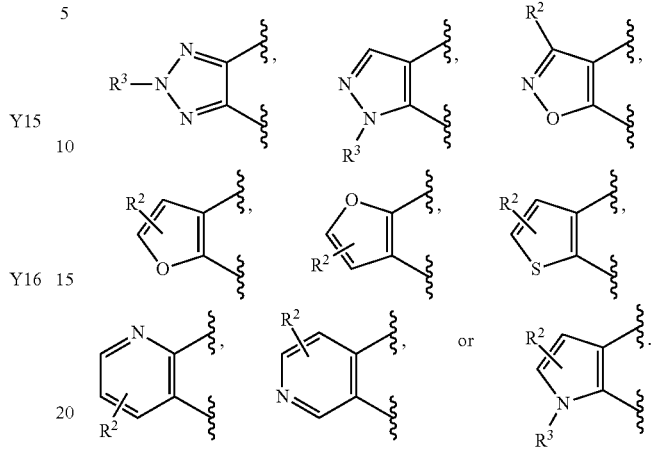

5. The compound according to claim 4 wherein the compound is 4-octahydro-6H-pyrrolo[3,4-b]pyridin-6-yl-6,7-dihydro-5H-thieno[2',3':6,7]cyclohepta[1,2-d]pyrimidin-2-amine;

4-[(3R)-3-aminopyrrolidin-1-yl]-6,7-dihydro-5H-thieno[2',3':6,7]cyclohepta[1,2-d]pyrimidin-2-amine;

4-[(3R)-3-(methylamino)pyrrolidin-1-yl]-6,7-dihydro-5H-thieno[2',3':6,7]cyclohepta[1,2-d]pyrimidin-2-amine;

4-octahydro-6H-pyrrolo[3,4-b]pyridin-6-yl-6,7-dihydro-5H-furo[2',3':6,7]cyclohepta[1,2-d]pyrimidin-2-amine;

9-methyl-4-octahydro-6H-pyrrolo[3,4-b]pyridin-6-yl-6,7-dihydro-5H-furo[2',3':6,7]cyclohepta[1,2-d]pyrimidin-2-amine;

4-[(3R)-3-aminopyrrolidin-1-yl]-9-methyl-6,7-dihydro-5H-furo[2',3':6,7]cyclohepta[1,2-d]pyrimidin-2-amine;

4-octahydro-6H-pyrrolo[3,4-b]pyridin-6-yl-6,7-dihydro-5H-furo[3',2':6,7]cyclohepta[1,2-d]pyrimidin-2-amine;

4-[(3R)-3-aminopyrrolidin-1-yl]-8-methyl-5,6,7,8-tetrahydropyrazolo[3',4':6,7]cyclohepta[1,2-d]pyrimidin-2-amine;

8-tert-butyl-4-octahydro-6H-pyrrolo[3,4-b]pyridin-6-yl-5,6,7,8-tetrahydropyrazolo[3',4':6,7]cyclohepta[1,2-d]pyrimidin-2-amine;

4-[(3R)-3-(methylamino)pyrrolidin-1-yl]-8-phenyl-5,6,7,8-tetrahydropyrazolo[3',4':6,7]cyclohepta[1,2-d]pyrimidin-2-amine;

9-bromo-4-octahydro-6H-pyrrolo[3,4-b]pyridin-6-yl-6,7-dihydro-5H-thieno[2',3':6,7]cyclohepta[1,2-d]pyrimidin-2-amine;

4-octahydro-6H-pyrrolo[3,4-b]pyridin-6-yl-9-phenyl-6,7-dihydro-5H-thieno[2',3':6,7]cyclohepta[1,2-d]pyrimidin-2-amine;

4-[(3R)-3-aminopyrrolidin-1-yl]-6,7-dihydro-5H-pyrido[3',2':6,7]cyclohepta[1,2-d]pyrimidin-2-amine;

4-[(3R)-3-aminopyrrolidin-1-yl]-10-methyl-6,7-dihydro-5H-isoxazolo[5',4':6,7]cyclohepta[1,2-d]pyrimidin-2-amine; or 4-[(4aR,7aR)-octahydro-6H-pyrrolo[3,4-b]pyridin-6-yl]-6,7-dihydro-5H-thieno[2',3':6,7]cyclohepta[1,2-d]pyrimidin-2-amine; or a pharmaceutically acceptable salt thereof.

6. The compound according to claim 1 wherein
G$^1$ is —CH$_2$—;
G$^2$ is —CH$_2$—; and
R$^1$ is NH$_2$, —NH(acyl), —NH(alkyl), —N(alkyl)$_2$, —NH(C=O)aryl, —NH-alkylene(NR$^7$R$^8$), —NH(C=O)-alkylene(NR$^7$R$^8$), —NR$^7$(C=O)NR$^7$R$^8$, —NH-alkylene-heteroaryl, —NHOH, or —NHOCH$_3$.

7. The compound according to claim 6, wherein A$^2$ is

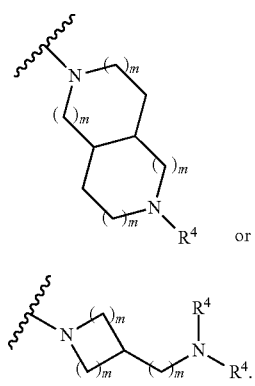

8. The compound according to claim 7, wherein W is a group of the formula:

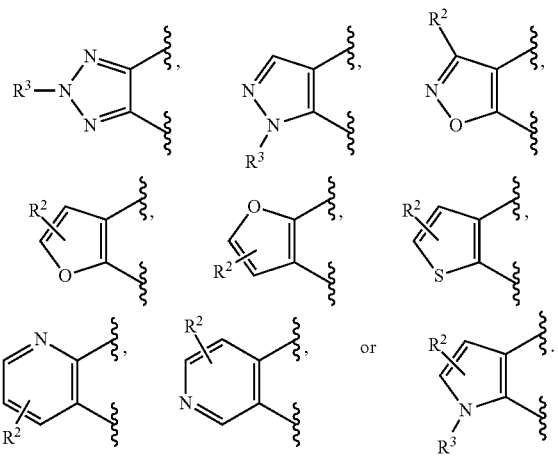

9. A pharmaceutical composition comprising a compound of formula (I) according to claim 1 and a pharmaceutically acceptable carrier.

* * * * *